United States Patent
Xu et al.

(10) Patent No.: US 9,557,338 B2
(45) Date of Patent: *Jan. 31, 2017

(54) INHIBITION OF PHOSPHORYLATION OF PRAS40, GSK3-BETA OR P70S6K1 AS A MARKER FOR TOR KINASE INHIBITORY ACTIVITY

(71) Applicant: SIGNAL PHARMACEUTICALS, LLC, San Diego, CA (US)

(72) Inventors: Weiming Xu, San Diego, CA (US); Deborah Mortensen, San Diego, CA (US); Shuichan Xu, San Diego, CA (US); Kimberly Elizabeth Fultz, San Diego, CA (US)

(73) Assignee: Signal Pharmaceuticals, LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/835,817

(22) Filed: Aug. 26, 2015

(65) Prior Publication Data

US 2015/0362505 A1  Dec. 17, 2015

Related U.S. Application Data

(62) Division of application No. 14/055,995, filed on Oct. 17, 2013, now Pat. No. 9,155,736.

(60) Provisional application No. 61/715,542, filed on Oct. 18, 2012.

(51) Int. Cl.
| | |
|---|---|
| *G01N 33/68* | (2006.01) |
| *A61K 31/4985* | (2006.01) |
| *G01N 33/50* | (2006.01) |
| *C12Q 1/48* | (2006.01) |
| *A61K 31/437* | (2006.01) |
| *A61K 31/519* | (2006.01) |
| *A61K 31/522* | (2006.01) |

(52) U.S. Cl.
CPC ......... *G01N 33/6842* (2013.01); *A61K 31/437* (2013.01); *A61K 31/4985* (2013.01); *A61K 31/519* (2013.01); *A61K 31/522* (2013.01); *C12Q 1/485* (2013.01); *G01N 33/5011* (2013.01); *G01N 2333/9121* (2013.01); *G01N 2800/52* (2013.01); *G01N 2800/7028* (2013.01)

(58) Field of Classification Search
IPC ........................................ G01N 33/68,33/6842
See application file for complete search history.

(56) References Cited

U.S. PATENT DOCUMENTS

| | | | |
|---|---|---|---|
| 3,507,866 A | 4/1970 | Jones et al. | |
| 3,567,725 A | 3/1971 | Grabowski et al. | |
| 4,294,836 A | 10/1981 | Lesher et al. | |
| 4,294,837 A | 10/1981 | Lesher et al. | |
| 4,309,537 A | 1/1982 | Lesher et al. | |
| 4,317,909 A | 3/1982 | Lesher et al. | |
| 4,898,872 A | 2/1990 | Campbell et al. | |
| 4,963,561 A | 10/1990 | Lesher et al. | |
| 5,424,311 A | 6/1995 | Billhardt-Troughton | |
| 5,869,659 A | 2/1999 | Stolle et al. | |
| 6,031,105 A | 2/2000 | Wright | |
| 6,093,728 A | 7/2000 | McMahon et al. | |
| 6,372,740 B1 | 4/2002 | Murata et al. | |
| 6,566,367 B2 | 5/2003 | Bakthavatchalam et al. | |
| 6,791,006 B2 | 9/2004 | Nezu et al. | |
| 6,800,436 B1 | 10/2004 | Jenne et al. | |
| 6,825,184 B2 | 11/2004 | Cirillo et al. | |
| 6,855,723 B2 | 2/2005 | McMahon et al. | |
| 7,199,119 B2 | 4/2007 | Burkitt et al. | |
| 7,247,621 B2 | 7/2007 | Hong et al. | |
| 7,429,572 B2 | 9/2008 | Clark | |
| 7,476,665 B2 | 1/2009 | Burgey | |
| 7,608,622 B2 | 10/2009 | Liu et al. | |
| 7,700,594 B2 | 4/2010 | Chen et al. | |
| 7,767,687 B2 | 8/2010 | Oslob et al. | |
| 7,902,187 B2 | 3/2011 | Neagu et al. | |
| 7,919,490 B2 | 4/2011 | Neagu et al. | |
| 7,968,556 B2 | 6/2011 | Mortensen et al. | |
| 7,981,893 B2 | 7/2011 | Mortensen et al. | |
| 8,110,578 B2 | 2/2012 | Perrin-Ninkovic et al. | |
| 8,268,809 B2 | 9/2012 | Kalman | |
| 8,372,976 B2 | 2/2013 | Mortensen et al. | |
| 8,383,634 B2 | 2/2013 | Mortensen et al. | |
| 8,492,381 B2 | 7/2013 | Perrin-Ninkovic et al. | |
| 8,569,494 B2 | 10/2013 | Harris et al. | |
| 8,628,931 B2 * | 1/2014 | Liotta ........................ | 435/40.51 |

(Continued)

FOREIGN PATENT DOCUMENTS

| | | |
|---|---|---|
| CA | 2 458 699 | 3/2003 |
| DE | 262 026 | 11/1988 |

(Continued)

OTHER PUBLICATIONS

Barlin 1982, "Purine analogs as amplifiers of phleomycin. VII. Some 1H-inidazo[4,5-b]pyrazines and related compound," Australian Journal of Chemistry, vol. 35:2299-2306.
Beresnev et al., 2000, "Interaction of 5-methoxy-1,2,4-traizines with uras as a new route to 6-azapurines," Medeleev Commu., vol. 2:58-59.
Bergmann et al., 1963, "2-Phenylpurines, their chemical and enzumological reactivity," J. Chem Org. , pp. 3729-3735.
Booth et al., 1992, "Synthesis of 9-Hydroxyalkyl-substituted purines from the corresponding 4-(C-Cyanoformimidoyl)imidazole-5-amines," J, Chem Society, Perkin Transactions 1: Organic and Bio-Organic Chemstry, vol. 2119-26.
Booth et al., 1995, "Synthesis of [1α, 2β,3α-2,3-bis(benzyloxymethyl)cyclobut1]imidazol-5-amines: important precursors to cyclobut-A derivatives," J. Chem Society, Perkin Tranactions 1: Organic and Bio-Organic Chemistry, vol. 6, pp. 669-675.
Booth et al., 2001, "The Reactions of Diaminomaleonitrile with Isocyanates and Either Aldehydes or Ketones Revisited," J. Org Chem, vol. 66:8436-8441.

(Continued)

*Primary Examiner* — Shirley V Gembeh
(74) *Attorney, Agent, or Firm* — Jones Day

(57) ABSTRACT

Provided herein are methods for treating a cancer treatable by inhibition of phosphorylation of PRAS40, GSK3β or p70S6K1, comprising administering an effective amount of a TOR kinase inhibitor to a patient having a cancer treatable by inhibition of phosphorylation of PRAS40, GSK3β or p70S6K1.

4 Claims, 1 Drawing Sheet

(56) References Cited

U.S. PATENT DOCUMENTS

| | | |
|---|---|---|
| 8,642,660 B2 | 2/2014 | Goldfarb |
| 2004/0063658 A1 | 4/2004 | Roberts et al. |
| 2006/0004014 A1 | 1/2006 | Hoffmann et al. |
| 2006/0142269 A1 | 6/2006 | Dykes |
| 2007/0036793 A1 | 2/2007 | Hardie et al. |
| 2008/0194019 A1 | 8/2008 | Cantley et al. |
| 2009/0181963 A1 | 7/2009 | Dehnhardt et al. |
| 2009/0281075 A1 | 11/2009 | Roughton et al. |
| 2010/0144738 A1 | 6/2010 | Bornmann et al. |
| 2011/0257167 A1 | 10/2011 | Chopra et al. |
| 2011/0318336 A1 | 12/2011 | Petricoin, III et al. |
| 2012/0028972 A1 | 2/2012 | Wong et al. |
| 2013/0102613 A1 | 4/2013 | Xu et al. |
| 2013/0142873 A1 | 6/2013 | Assaf et al. |
| 2013/0158023 A1 | 6/2013 | Ning et al. |
| 2013/0225518 A1 | 8/2013 | Xu et al. |
| 2013/0245026 A1 | 9/2013 | Xu et al. |
| 2013/0245027 A1 | 9/2013 | Xu et al. |
| 2013/0245028 A1 | 9/2013 | Xu et al. |
| 2013/0245029 A1 | 9/2013 | Xu et al. |
| 2014/0113904 A1 | 4/2014 | Mortensen et al. |

FOREIGN PATENT DOCUMENTS

| | | |
|---|---|---|
| EP | 0 385 850 | 9/1990 |
| JP | 63275582 | 5/1987 |
| JP | 2001048882 | 2/2001 |
| JP | 2002100363 | 4/2002 |
| JP | 2002167387 | 6/2002 |
| WO | WO 03/32989 | 4/1903 |
| WO | WO 04/42002 | 5/1904 |
| WO | WO 99/16438 | 4/1999 |
| WO | WO 99/28320 | 6/1999 |
| WO | WO 99/28459 | 6/1999 |
| WO | WO 00/73306 | 12/2000 |
| WO | WO 02/048152 | 6/2002 |
| WO | WO 02/076954 | 10/2002 |
| WO | WO 03/032989 | 4/2003 |
| WO | WO 03/072557 | 9/2003 |
| WO | WO 03/093290 | 11/2003 |
| WO | WO 2004/042002 | 5/2004 |
| WO | WO 2004/048365 | 6/2004 |
| WO | WO 2004/065378 | 8/2004 |
| WO | WO 2004/076454 | 9/2004 |
| WO | WO 2004/078754 | 9/2004 |
| WO | WO 2004/085409 | 10/2004 |
| WO | WO 2004/096797 | 11/2004 |
| WO | WO 2005/003147 | 1/2005 |
| WO | WO 2005/021519 | 3/2005 |
| WO | WO 2005/120511 | 12/2005 |
| WO | WO 2006/001266 | 1/2006 |
| WO | WO 2006/018182 | 2/2006 |
| WO | WO 2006/030031 | 3/2006 |
| WO | WO 2006/036883 | 4/2006 |
| WO | WO 2006/045828 | 5/2006 |
| WO | WO 2006/046031 | 5/2006 |
| WO | WO 2006/050076 | 5/2006 |
| WO | WO 2006/065703 | 6/2006 |
| WO | WO 2006/087530 | 8/2006 |
| WO | WO 2006/090167 | 8/2006 |
| WO | WO 2006/090169 | 8/2006 |
| WO | WO 2006/091737 | 8/2006 |
| WO | WO 2006/108103 | 10/2006 |
| WO | WO 2007/044698 | 4/2007 |
| WO | WO 2007/044729 | 4/2007 |
| WO | WO 2007/044813 | 4/2007 |
| WO | WO 2007/047754 | 4/2007 |
| WO | WO 2007/060404 | 5/2007 |
| WO | WO 2007/066099 | 6/2007 |
| WO | WO 2007/066102 | 6/2007 |
| WO | WO 2007/080382 | 7/2007 |
| WO | WO 2007/125321 | 11/2007 |
| WO | WO 2007/129044 | 11/2007 |
| WO | WO 2007/129052 | 11/2007 |
| WO | WO 2007/129161 | 11/2007 |
| WO | WO 2007/135398 | 11/2007 |
| WO | WO 2008/016669 | 2/2008 |
| WO | WO 2008/023161 | 2/2008 |
| WO | WO 2008/032027 | 3/2008 |
| WO | WO 2008/032028 | 3/2008 |
| WO | WO 2008/032033 | 3/2008 |
| WO | WO 2008/032036 | 3/2008 |
| WO | WO 2008/032060 | 3/2008 |
| WO | WO 2008/032064 | 3/2008 |
| WO | WO 2008/032072 | 3/2008 |
| WO | WO 2008/032077 | 3/2008 |
| WO | WO 2008/032089 | 3/2008 |
| WO | WO 2008/032091 | 3/2008 |
| WO | WO 2008/051493 | 5/2008 |
| WO | WO 2008/064093 | 5/2008 |
| WO | WO 2008/115974 | 9/2008 |
| WO | WO 2008/140947 | 11/2008 |
| WO | WO 2009/007748 | 1/2009 |
| WO | WO 2009/007750 | 1/2009 |
| WO | WO 2009/007751 | 1/2009 |
| WO | WO 2009/052145 | 4/2009 |
| WO | WO 2009/102986 | 8/2009 |
| WO | WO 2010/006072 | 1/2010 |
| WO | WO 2010/062571 | 6/2010 |
| WO | WO 2010/068483 | 6/2010 |
| WO | WO 2011/031965 | 3/2011 |
| WO | WO 2011/079114 | 6/2011 |
| WO | WO 2011/097333 | 8/2011 |

OTHER PUBLICATIONS

Booth, et al., 1994, "Synthesis of 4- and 5-Disubstituted 1-Benzylimidazoles, Important Precursors of Purine Analogs," J. of Heterocyclic of Chemistry, vol. 31(2):345-50.

Carretero et al. 2010, "Integrative Genomic and Proteomic Analyses Indentity Targets for Lkb1-Deficient Metastatic Lung Tumors," Cancer Cell, vol. 17(6): 547-559.

Chupakhin et al., 2001, "A simple one pot synthesis of condensed 1,2,4-triazines by using the tandem $A_N$-$S_N$ipso and $S_N^H$—$S_N$ipso reactions," J. of Heterocyclic Chemistry, vol. 38(4):901-907.

Cohen, P. 2001, "The role of protein phosphorylation in human health and disease," Eur. J. Biochem,vol. 268:5001-5010.

Cohen, P. 2002, "Protein kinases—the major drug targets of the twenty-first century?" Nature Reviews/Drug Discovery, vol. 1:309-315.

Cohen, 2005, *Protein Kinase Inhibitors for the Treatment of Disease: The Promise and the Problems*, Handbook of Experimental Pharmacology, Springer Berlin Heidelberg, 167:1-7.

Coish, et al., 2006, "Small molecule inhibitors of IKK kinase activity," Expert Opin. Ther. Patents, vol. 16(1):1-12.

Crofts et al., 1997 "Metabolism of 2-amino-1-methyl-6-phenylimidazo [4,5-b]pyridine (PhIP) by human cytochrome P4501B1," Carcinogenesis, vol. 18(9):1793-1798.

Dang et al., 1999, "Efficient synthesis of purines and purine nucelosides via an inverse electron demand diels—alder reaction," J. Am Chem Soc., vol. 121(24):5833-5834.

Database Caplus Online Chemical Abstracts Service, Columbus, Ohio, Database Accession No. 1951:49974 (XP-002472261) (1951).

Database Caplus Online Chemical Abstracts Service, Columbus, Ohio, Database Accession No. 1978:433195 (XP-002472262) (1978).

Database Caplus Online Chemical Abstracts Service, Columbus, Ohio, Database Accession No. 1966:26849 (XP-002472263) (1965).

Dornow et al., 1957, "Synthese von2-Oxy-imidazolo-(5',4':2,3)-pyridinen)," Arch Pharm. vol. 290, pp. 20-31 (w/English language abstract).

Dzierba et al., 2004, "Synthesis, structure-activity relationships, and in vivo properties of 3,4-dihydro-1H-pyrido[2,3-b]pyrazin-2-ones as corticotropin-releasing factor-1 receptor antagonists," J of Medicinal Chemistry, vol. 47, pp. 5783-5790.

Fabbro et al., 2002, "Protein kinases as targets for anticancer agents: from inhibitors to useful drugs," Pharmacol Ther., 93(2-3):79-98.

(56) References Cited

OTHER PUBLICATIONS

Farhadi et al., 2006, "The role of protein kinase C isoforms in modulating injury and repair of the intestinal barrier," J. Pharm Exp. Ther., vol. 316(1):1-7.
Frandsen et al., 1992, "Reaction of the N2-acetoxy derivative of 2-amino-1-methyl-6-phenylimidazo[4,5,b] pyridine . . . ," Carcinogenesis, vol. 13(4):629-635.
Gao et al., 2010, "LKB1 inhibits lung cancer progression through lysyl oxidase and extracellular matrix remodeling," Proceedings of the National Academy of Sciences, vol. 107(44): 18892-18897.
Georgakis and Younes, 2006, "From rapi nui to rapamycin: targeting PI3K/Akt/mTOR for cancer therapy," Expert Rev. Anticancer Ther., vol. 6(1):131-140.
Grimmiger et al., 2010, "Targeting non-malignant disorders with tyrosine kinase inhibitors," Nat. Rev. Drug Disc., 9(12):956-970.
Hamad, 2001, "A new synthesis of 4-cyano-1,3-dihydro-2-oxo-2H-imidazole-5-($N^1$-tosyl)carboxamide: Reactive precursor for thiopurine analogues," J of Heterocyclic Chemistry, vol. 38(4):939-944.
Hernan et al., "De novo germline mutation in the serine-threonine kinase STK11/LKB1 gene associated with Peutz-Jeghers syndrome," Clin Genet., 66(1):58-62.
Huang et al., 2010, "Genetic and epigenetic silencing of SCARA5 may contribute to human hepatocellular carcinoma by activating FAK signaling," Journal of Clinical Investigation, American Society for Clinical investigation, vol. 120(1): 223-241.
Inge et al., 2009, "Expression of LKB1 tumor suppressor in non-small cell lung cancer determines sensitivity to 2-deoxyglucose," Journal of Thoracic and Cardiovascular Surgery, vol. 137(3): 580-586.
Irie et al., 2005, "Toward the development of new medicinal leads with selectivity for protein kinase C isozymes," The Chemical Record, vol. 5:185-195.
Itoh et al., 2004, "A novel practical synthesis of C-2-arylpurines," Advanced Synthesis & Catalysis, vol. 346:1859-1867.
Ji et al., 2007, "LKB1 modulates lung cancer differentiation and metastasis," Nature, 448(7155):807-810.
Jones et al., 1973, "6-Substituted-5-chloro-1,3-dihydro-2H-imidazo(4,5-b)pyrazin-2-ones with hypotensive activity," J. Med. Chem., vol. 16(5):537-542.
Kazaoka et al., 2003, "Synthesis of 6-substituted 9-benzyl-8-hydroxypurines with potential interferon-indcuing activity," Chemical & Pharmaceutical Bulletin, vol. 51(5):608-611.
Killday et al., 2001, "Microxine, a new cdc2 kinase inhibitor from the Australian marine sponge Microxina species," J. of Natural Products, vol. 64(4):525-526.
Mahoney et al., 2009, "LKB1/KRAS mutant lung cancers constitute a genetic subset of NSCLC with increased sensitivity to MAPK and mTOR signalling inhibition," Br J Cancer, 100(2):370-375.
Minehan et al., 2000, "Molecular recognition of DNA by Hoechst Benzimidazoles: Exploring beyond theopyrrole-imidazole-hydroxypyrrole polyamide-pairing code," Helvitica Chima Acta, vol. 83(9):2197-2213.
Nagashima et al., 2004, "Solution-Phase parallel synthesis of an N-Alkylated dihydropteridinone library from fluorous amino acids," J of Comb. Chemistry, vol. 6(6):942-949.

Park et al., 2000, "A novel mechanism of TRAF signaling revealed by structural and functional analyses of the TRADD-TRAF2 interaction," Cell, vol. 101:777-787.
Patani et al., 1998, "Bioisosterim: A rational approach in drug design," Chemical Reviews, vol. 96:3147-3176.
PCT Annex to Form PCT/ISA?206 Communication Relating to the Results of the Partial International Search issued in connection with PCT/US2012/049281,filed Aug. 2, 2012.
PCT International Search Report issued in connection with PCT/US2012/049281, filed Aug. 2, 2012.
PCT Written Opinion of the International Searching Authority issued in connection with PCT/US2012/049281, filed Aug. 2, 2012.
Registry File Document for RN 863501-03-5, 863502-39-0 and others (Sep. 20, 2005).
Yuan et al., 2009, "Targeting tumorigenesis: development and use of mTOR inhibitors in cancer therapy," Journal of Hematology & Oncology, Biomed Central Ltd., London UK, vol. 2(1): 45.
Seela et al., 2004, "Product Class 17: Purines," Science of Synthesis, vol. 16, pp. 945-1108.
Shaw et al., 2004, "The LKB1 tumor suppressor negativiely regulates mTOR signaling," Cancer Cell, vol. 6(1): 91-99.
Shaw et al., 2009, "LKB1 and AMP-activated protein kinase control of mTOR signalling and growth," Acta. Physiol (Oxf.) 196(1):65-80.
Singh et al., 1994, "Novel cAMP PDE III Inhibitors: Imidazo[4,5-b]pyridin-2(3H)-ones and Thiazolo[4,5-b]pyridin-2(3h)-ones and Their Analogs," J. Med. Chem, vol. 37(2):248-54.
Sridhar et al., 2000, "Protein kinases as therapeutic targets," Pharm. Res., 17(11):1345-1353.
Wallace 2008, "Palladium-catalyzed synthesis of quinoxaline derivatives," Tetrahedron, vol. 64:9675-9684.
Wei et al., 2009, "Chemopreventive efficacy of rapamycin on Peutz-Jeghers syndrome in a mouse model," Cancer Lett., 277(2):149-154.
Westover et al., 1981, "Synthesis and antiviral activity of certain 9-β-D-Riofuranoaylpurine-6-carboxamides," J.Med. Chem., vol. 24(8):941-46.
Wingo et al., 2009, "Somatic LKB1 mutations promote cervical cancer progression," PLoS One, 4(4):1-8.
Gao et al.: 2011, "LKB1 in lung cancerigenesis: a serine/threonine kinase as tumor suppressor," Protein & Cell, Gaodeng Jiaoyu Chubanshe, China, vol. 2(2): 99-107.
Yoneda et al., 1976, "A transformationof 7-azapteridines into 6-azapurines (Imidazo[4,5-e]-as—triazines)," Heterocycles, vol. 4(9):1503-1508.
Yoneda et al., 1978, "Synthesis of imadazo[4,5-e]-as-triazine (6-Azapurine) Deriviatives," Chem & Pharm Bulletin, vol. 26(10):3154-3160.
Zaki et al., 2007, "The synthesis of imidazol[4,5-d]pyridines from a substituted imidazole and acyl or sulfonyl acetonitrile," Tetrahedron, vol. 63(18):3745-3753.
Zhong et al., 2006, "LKB1 mutation in large cell carcinoma of the lung," Cancer Lung, vol. 53(3):285-294.
Shoji et al. (2012) "Genotype-dependent efficacy of a dual PI3K/mTOR inhibitor, NVP-BEZ235, and an mTOR inhibitor, RAD001, in endometrial carcinomas." PLoS one 7.5, 2012, e37431.

* cited by examiner

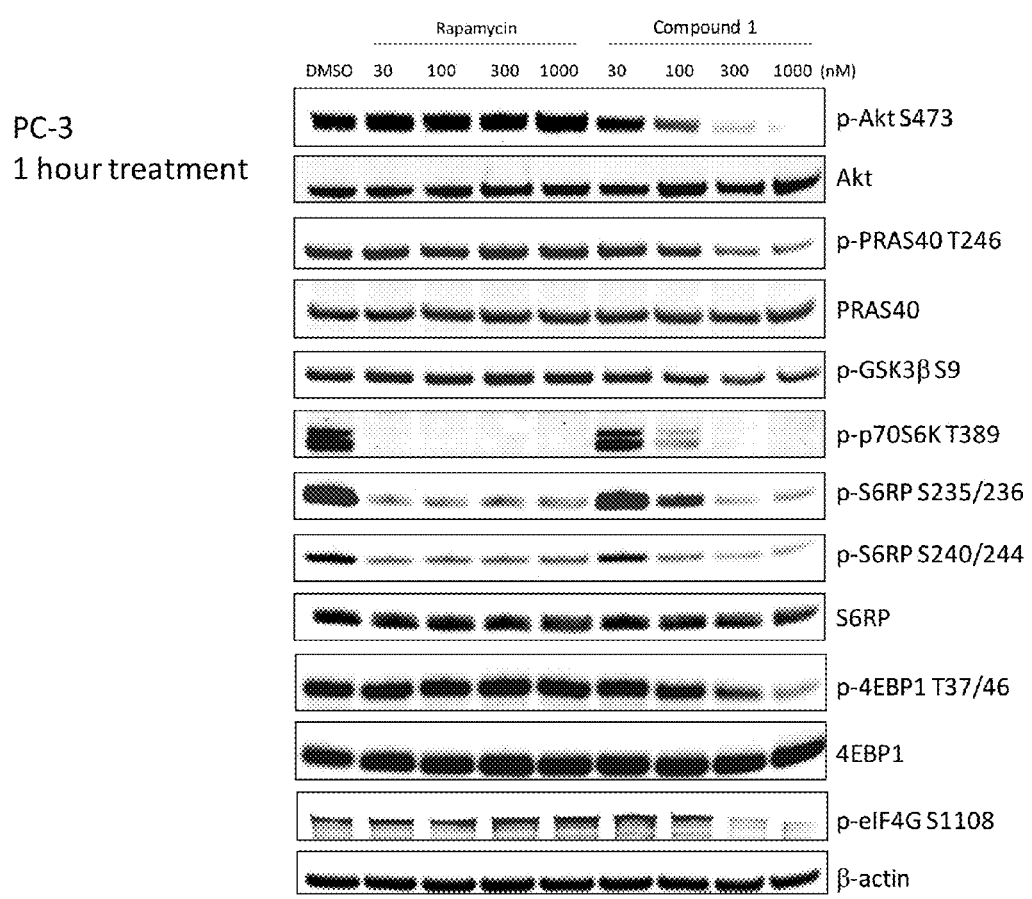

US 9,557,338 B2

INHIBITION OF PHOSPHORYLATION OF PRAS40, GSK3-BETA OR P70S6K1 AS A MARKER FOR TOR KINASE INHIBITORY ACTIVITY

This application is a divisional of U.S. application Ser. No. 14/055,995, filed Oct. 17, 2013, currently allowed, which claims the benefit of U.S. Provisional Application No. 61/715,542, filed Oct. 18, 2012, the entire contents of which are incorporated herein by reference.

1. FIELD

Provided herein are methods for treating and/or preventing a cancer treatable by inhibition of phosphorylation of PRAS40, GSK3β and/or p70S6K1 in a patient, comprising administering an effective amount of a TOR kinase inhibitor to a patient having a cancer treatable by inhibition of phosphorylation of PRAS40, GSK3β and/or p70S6K1.

2. BACKGROUND

The connection between abnormal protein phosphorylation and the cause or consequence of diseases has been known for over 20 years. Accordingly, protein kinases have become a very important group of drug targets. See Cohen, *Nat. Rev. Drug Disc.,* 1:309-315 (2002), Grimmiger et al. *Nat. Rev. Drug Disc.* 9(12):956-970 (2010). Various protein kinase inhibitors have been used clinically in the treatment of a wide variety of diseases, such as cancer and chronic inflammatory diseases, including diabetes and stroke. See Cohen, *Eur. J. Biochem.,* 268:5001-5010 (2001), *Protein Kinase Inhibitors for the Treatment of Disease: The Promise and the Problems,* Handbook of Experimental Pharmacology, Springer Berlin Heidelberg, 167 (2005).

The protein kinases belong to a large and diverse family of enzymes that catalyze protein phosphorylation and play a critical role in cellular signaling. Protein kinases may exert positive or negative regulatory effects, depending upon their target protein. Protein kinases are involved in specific signaling pathways which regulate cell functions such as, but not limited to, metabolism, cell cycle progression, cell adhesion, vascular function, apoptosis, and angiogenesis. Malfunctions of cellular signaling have been associated with many diseases, the most characterized of which include cancer and diabetes. The regulation of signal transduction by cytokines and the association of signal molecules with protooncogenes and tumor suppressor genes have been well documented. Similarly, the connection between diabetes and related conditions, and deregulated levels of protein kinases, has been demonstrated. See e.g., Sridhar et al. *Pharm. Res.* 17(11):1345-1353 (2000). Viral infections and the conditions related thereto have also been associated with the regulation of protein kinases. Park et al. *Cell* 101(7): 777-787 (2000).

Protein kinases can be divided into broad groups based upon the identity of the amino acid(s) that they target (serine/threonine, tyrosine, lysine, and histidine). For example, tyrosine kinases include receptor tyrosine kinases (RTKs), such as growth factors and non-receptor tyrosine kinases, such as the src kinase family. There are also dual-specific protein kinases that target both tyrosine and serine/threonine, such as cyclin dependent kinases (CDKs) and mitogen-activated protein kinases (MAPKs).

Because protein kinases regulate nearly every cellular process, including metabolism, cell proliferation, cell differentiation, and cell survival, they are attractive targets for therapeutic intervention for various disease states. For example, cell-cycle control and angiogenesis, in which protein kinases play a pivotal role are cellular processes associated with numerous disease conditions such as, but not limited to, cancer, inflammatory diseases, abnormal angiogenesis and diseases related thereto, atherosclerosis, macular degeneration, diabetes, obesity, and pain.

Protein kinases have become attractive targets for the treatment of cancers. Fabbro et al. *Pharm. Ther.* 93:79-98 (2002). It has been proposed that the involvement of protein kinases in the development of human malignancies may occur by: (1) genomic rearrangements (e.g., BCR-ABL in chronic myelogenous leukemia), (2) mutations leading to constitutively active kinase activity, such as acute myelogenous leukemia and gastrointestinal tumors, (3) deregulation of kinase activity by activation of oncogenes or loss of tumor suppressor functions, such as in cancers with oncogenic RAS, (4) deregulation of kinase activity by over-expression, as in the case of EGFR and (5) ectopic expression of growth factors that can contribute to the development and maintenance of the neoplastic phenotype. Fabbro et al., *Pharm. Ther.* 93:79-98 (2002).

The elucidation of the intricacy of protein kinase pathways and the complexity of the relationship and interaction among and between the various protein kinases and kinase pathways highlights the importance of developing pharmaceutical agents capable of acting as protein kinase modulators, regulators or inhibitors that have beneficial activity on multiple kinases or multiple kinase pathways. Accordingly, there remains a need for new kinase modulators.

The protein named mTOR (mammalian target of rapamycin), also called FRAP, RAFTI or RAPT1), is a 2549-amino acid Ser/Thr protein kinase, that has been shown to be one of the most critical proteins in the mTOR/PI3K/Akt pathway that regulates cell growth and proliferation. Georgakis and Younes *Expert Rev. Anticancer Ther.* 6(1):131-140 (2006). mTOR exists within two complexes, mTORC1 and mTORC2. While mTORC1 is sensitive to rapamycin analogs (such as temsirolimus or everolimus), mTORC2 is largely rapamycin-insensitive. Notably, rapamycin is not a TOR kinase inhibitor. Several mTOR inhibitors have been or are being evaluated in clinical trials for the treatment of cancer. Temsirolimus was approved for use in renal cell carcinoma in 2007 and everolimus was approved in 2009 for renal cell carcinoma patients that have progressed on vascular endothelial growth factor receptor inhibitors. In addition, sirolimus was approved in 1999 for the prophylaxis of renal transplant rejection. The interesting but limited clinical success of these mTORC1 inhibitory compounds demonstrates the usefulness of mTOR inhibitors in the treatment of cancer and transplant rejection, and the increased potential for compounds with both mTORC1 and mTORC2 inhibitory activity.

Due to the potential pharmaceutical applications for inhibitors of TOR kinase activity, there is a need for methods for detecting and/or measuring the inhibition of TOR kinase activity in vivo.

Citation or identification of any reference in this section is not to be construed as an admission that the reference is prior art to the present application.

3. SUMMARY

Provided herein are methods for detecting or measuring the inhibition of TOR kinase activity in a patient, comprising measuring the amount of phosphorylated PRAS40, GSK3β and/or p70S6K1 in a biological sample from said patient, for example a peripheral blood sample, prior to and after the administration of the TOR kinase inhibitor to said patient. The methods provided herein are believed to have utility in following the inhibition of TOR kinase in a patient.

Further provided herein are methods for determining a dose-response relationship for the administration of a TOR kinase inhibitor to a patient, wherein said patient is administered varying doses of said TOR kinase inhibitor and the amount of TOR kinase activity inhibition in said patient resulting from each dose of said TOR kinase inhibitor is determined by measuring the amount of phosphorylated PRAS40, GSK3β and/or p70S6K1 in a biological sample from said patient, for example a peripheral blood sample, prior to and after the administration of each dose of the TOR kinase inhibitor to said patient.

In certain embodiments, provided herein are methods for inhibiting phosphorylation of PRAS40, GSK3β and/or p70S6K1 in a biological sample of a patient having cancer (for example, prostate cancer, lung cancer, colon cancer, glioma or breast cancer), comprising administering an effective amount of a TOR kinase inhibitor to said patient and comparing the amount of phosphorylated PRAS40, GSK3β and/or p70S6K1 in a biological sample of a patient obtained prior to and after administration of said TOR kinase inhibitor, wherein less phosphorylated PRAS40, GSK3β and/or p70S6K1 in said biological sample obtained after administration of said TOR kinase inhibitor relative to the amount of phosphorylated PRAS40, GSK3β and/or p70S6K1 in said biological sample obtained prior to administration of said TOR kinase inhibitor indicates inhibition.

Also provided herein are methods for treating a cancer treatable by inhibition of phosphorylation of PRAS40, GSK3β and/or p70S6K1, comprising administering an effective amount of a TOR kinase inhibitor to a patient having a cancer treatable by inhibition of phosphorylation of PRAS40, GSK3β and/or p70S6K1. In certain such embodiments, the cancer is prostate cancer, lung cancer, colon cancer, glioma or breast cancer.

Also provided herein are methods for treating a cancer treatable by inhibition of phosphorylation of PRAS40, GSK3β and/or p70S6K1 comprising screening an individual for the presence of a cancer expressing PRAS40, GSK3β and/or p70S6K1 and administering an effective amount of a TOR kinase inhibitor to a patient having a cancer treatable by inhibition of phosphorylation of PRAS40, GSK3β and/or p70S6K1. In certain such embodiments, the cancer is prostate cancer, lung cancer, colon cancer, glioma or breast cancer.

Also provided herein are methods for inhibiting the in vivo phosphorylation of PRAS40, GSK3β and/or p70S6K1 comprising administering an effective amount of a TOR kinase inhibitor to a patient having a cancer treatable by inhibition of phosphorylation of PRAS40, GSK3β and/or p70S6K1. In certain such embodiments, the cancer is prostate cancer, lung cancer, colon cancer, glioma or breast cancer.

Also provided herein are methods for predicting the likelihood of a cancer of a patient being responsive to TOR kinase inhibitor therapy, comprising: screening a biological sample of said patient for the presence of PRAS40, GSK3β and/or p70S6K1, the phosphorylation of which is inhibited by a TOR kinase inhibitor; wherein the presence of PRAS40, GSK3β and/or p70S6K1, the phosphorylation of which is inhibited by a TOR kinase inhibitor, indicates an increased likelihood that a cancer of said patient will be responsive to TOR kinase inhibitor therapy. In certain such embodiments, the cancer is prostate cancer, lung cancer, colon cancer, glioma or breast cancer.

In certain embodiments, the method further comprises predicting the therapeutic efficacy of treatment of a patient with a TOR kinase inhibitor, comprising administering a TOR kinase inhibitor to said patient; obtaining a biological sample from said patient; measuring the level of phosphorylation of PRAS40, GSK3β and/or p70S6K1 in said biological sample; and comparing said measurement with a control measurement from the patient prior to treatment with said TOR kinase inhibitor; wherein a decrease in phosphorylation of PRAS40, GSK3β and/or p70S6K1 in said biological sample relative to the control measurement indicates an increase in therapeutic efficacy of treatment of said patient with a TOR kinase inhibitor.

Further provided herein are methods for determining whether a patient is sensitive to a TOR kinase inhibitor, comprising administering said patient said TOR kinase inhibitor and determining whether or not TOR kinase activity is inhibited in said patient by measuring the amount of phosphorylated PRAS40, GSK3β and/or p70S6K1 in a biological sample from said patient, for example a peripheral blood sample, prior to and after the administration of the TOR kinase inhibitor to said patient.

Further provided herein are methods for determining the effective amount of a TOR kinase inhibitor for the treatment of a cancer treatable by inhibition of phosphorylation of PRAS40, GSK3β and/or p70S6K1 in a patient, comprising administering said patient varying doses of said TOR kinase inhibitor and determining the amount of TOR kinase activity inhibition in said patient resulting from each dose of said TOR kinase inhibitor by measuring the amount of phosphorylated PRAS40, GSK3β and/or p70S6K1 in a biological sample from said patient, for example a peripheral blood sample, prior to and after the administration of each dose of TOR kinase inhibitor to said patient. In certain such embodiments, the cancer is prostate cancer, lung cancer, colon cancer, glioma or breast cancer.

Also provided herein is a kit for detecting inhibition of phosphorylation of PRAS40, GSK3β and/or p70S6K1 by a TOR kinase inhibitor, comprising reagents for measuring phosphorylation of PRAS40, GSK3β and/or p70S6K1 and one or more TOR kinase inhibitors.

In some embodiments, the TOR kinase inhibitor is a compound as described herein.

The present embodiments can be understood more fully by reference to the detailed description and examples, which are intended to exemplify non-limiting embodiments.

4. BRIEF DESCRIPTION OF THE DRAWINGS

FIG. 1 shows the inhibition of mTORC1 and mTORC2 by Compound 1, as measured by inhibition of the phosphorylation of the pathway markers Akt, PRAS40, GSK-3β, p70S6, S6, and 4-EBP1. Rapamycin partially inhibited mTORC1 and does not inhibit mTORC2.

5. DETAILED DESCRIPTION

5.1 Definitions

An "alkyl" group is a saturated, partially saturated, or unsaturated straight chain or branched non-cyclic hydrocarbon having from 1 to 10 carbon atoms, typically from 1 to 8 carbons or, in some embodiments, from 1 to 6, 1 to 4, or 2 to 6 or carbon atoms. Representative alkyl groups include -methyl, -ethyl, -n-propyl, -n-butyl, -n-pentyl and -n-hexyl;

while saturated branched alkyls include -isopropyl, -sec-butyl, -isobutyl, -tert-butyl, -isopentyl, 2-methylpentyl, 3-methylpentyl, 4-methylpentyl, 2,3-dimethylbutyl and the like. Examples of unsaturated alkyl groups include, but are not limited to, vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, —C≡CH, —C≡C(CH$_3$), —C≡C(CH$_2$CH$_3$), —CH$_2$C≡CH, —CH$_2$C≡C(CH$_3$) and —CH$_2$C≡C(CH$_7$CH$_3$), among others. An alkyl group can be substituted or unsubstituted. Unless otherwise indicated, when the alkyl groups described herein are said to be "substituted," they may be substituted with any substituent or substituents as those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonato; phosphine; thiocarbonyl; sulfonyl; sulfone; sulfonamide; ketone; aldehyde; ester; urea; urethane; oxime; hydroxyl amine; alkoxyamine; aralkoxyamine; N-oxide; hydrazine; hydrazide; hydrazone; azide; isocyanate; isothiocyanate; cyanate; thiocyanate; oxygen (=O); B(OH)2, or O(alkyl)aminocarbonyl.

An "alkenyl" group is a straight chain or branched non-cyclic hydrocarbon having from 2 to 10 carbon atoms, typically from 2 to 8 carbon atoms, and including at least one carbon-carbon double bond. Representative straight chain and branched (C$_2$-C$_8$)alkenyls include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl and the like. The double bond of an alkenyl group can be unconjugated or conjugated to another unsaturated group. An alkenyl group can be unsubstituted or substituted.

A "cycloalkyl" group is a saturated, partially saturated, or unsaturated cyclic alkyl group of from 3 to 10 carbon atoms having a single cyclic ring or multiple condensed or bridged rings which can be optionally substituted with from 1 to 3 alkyl groups. In some embodiments, the cycloalkyl group has 3 to 8 ring members, whereas in other embodiments the number of ring carbon atoms ranges from 3 to 5, 3 to 6, or 3 to 7. Such cycloalkyl groups include, by way of example, single ring structures such as cyclopropyl, cyclobutyl, cyclopentyl, cyclohexyl, cycloheptyl, cyclooctyl, 1-methylcyclopropyl, 2-methylcyclopentyl, 2-methylcyclooctyl, and the like, or multiple or bridged ring structures such as adamantyl and the like. Examples of unsaturated cycloalkyl groups include cyclohexenyl, cyclopentenyl, cyclohexadienyl, butadienyl, pentadienyl, hexadienyl, among others. A cycloalkyl group can be substituted or unsubstituted. Such substituted cycloalkyl groups include, by way of example, cyclohexanone and the like.

An "aryl" group is an aromatic carbocyclic group of from 6 to 14 carbon atoms having a single ring (e.g., phenyl) or multiple condensed rings (e.g., naphthyl or anthryl). In some embodiments, aryl groups contain 6-14 carbons, and in others from 6 to 12 or even 6 to 10 carbon atoms in the ring portions of the groups. Particular aryls include phenyl, biphenyl, naphthyl and the like. An aryl group can be substituted or unsubstituted. The phrase "aryl groups" also includes groups containing fused rings, such as fused aromatic-aliphatic ring systems (e.g., indanyl, tetrahydronaphthyl, and the like).

A "heteroaryl" group is an aryl ring system having one to four heteroatoms as ring atoms in a heteroaromatic ring system, wherein the remainder of the atoms are carbon atoms. In some embodiments, heteroaryl groups contain 5 to 6 ring atoms, and in others from 6 to 9 or even 6 to 10 atoms in the ring portions of the groups. Suitable heteroatoms include oxygen, sulfur and nitrogen. In certain embodiments, the heteroaryl ring system is monocyclic or bicyclic. Non-limiting examples include but are not limited to, groups such as pyrrolyl, pyrazolyl, imidazolyl, triazolyl, tetrazolyl, oxazolyl, isoxazolyl, thiazolyl, pyrolyl, pyridyl, pyridazinyl, pyrimidinyl, pyrazinyl, thiophenyl, benzothiophenyl, furanyl, benzofuranyl (for example, isobenzofuran-1,3-diimine), indolyl, azaindolyl (for example, pyrrolopyridyl or 1H-pyrrolo[2,3-b]pyridyl), indazolyl, benzimidazolyl (for example, 1H-benzo[d]imidazolyl), imidazopyridyl (for example, azabenzimidazolyl, 3H-imidazo[4,5-b]pyridyl or 1H-imidazo[4,5-b]pyridyl), pyrazolopyridyl, triazolopyridyl, benzotriazolyl, benzoxazolyl, benzothiazolyl, benzothiadiazolyl, isoxazolopyridyl, thianaphthalenyl, purinyl, xanthinyl, adeninyl, guaninyl, quinolinyl, isoquinolinyl, tetrahydroquinolinyl, quinoxalinyl, and quinazolinyl groups.

A "heterocyclyl" is an aromatic (also referred to as heteroaryl) or non-aromatic cycloalkyl in which one to four of the ring carbon atoms are independently replaced with a heteroatom from the group consisting of O, S and N. In some embodiments, heterocyclyl groups include 3 to 10 ring members, whereas other such groups have 3 to 5, 3 to 6, or 3 to 8 ring members. Heterocyclyls can also be bonded to other groups at any ring atom (i.e., at any carbon atom or heteroatom of the heterocyclic ring). A heterocyclylalkyl group can be substituted or unsubstituted. Heterocyclyl groups encompass unsaturated, partially saturated and saturated ring systems, such as, for example, imidazolyl, imidazolinyl and imidazolidinyl groups. The phrase heterocyclyl includes fused ring species, including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. Representative examples of a heterocyclyl group include, but are not limited to, aziridinyl, azetidinyl, pyrrolidyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl (for example, tetrahydro-2H-pyranyl), tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl; for example, 1H-imidazo[4,5-b]pyridyl, or 1H-imidazo[4,5-b]pyridin-2(3H)-onyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be monosubstituted or substituted more than once, such as, but not limited to, pyridyl or morpholinyl groups, which are 2-, 3-, 4-, 5-, or 6-substituted, or disubstituted with various substituents such as those listed below.

An "cycloalkylalkyl" group is a radical of the formula: -alkyl-cycloalkyl, wherein alkyl and cycloalkyl are defined above. Substituted cycloalkylalkyl groups may be substituted at the alkyl, the cycloalkyl, or both the alkyl and the cycloalkyl portions of the group. Representative cycloalkylalkyl groups include but are not limited to cyclopentylmethyl, cyclopentylethyl, cyclohexylmethyl, cyclohexylethyl, and cyclohexylpropyl. Representative substituted cycloalkylalkyl groups may be mono-substituted or substituted more than once.

An "aralkyl" group is a radical of the formula: -alkyl-aryl, wherein alkyl and aryl are defined above. Substituted aralkyl groups may be substituted at the alkyl, the aryl, or both the alkyl and the aryl portions of the group. Representative aralkyl groups include but are not limited to benzyl and phenethyl groups and fused (cycloalkylaryl)alkyl groups such as 4-ethyl-indanyl.

A "heterocyclylalkyl" group is a radical of the formula: -alkyl-heterocyclyl, wherein alkyl and heterocyclyl are defined above. Substituted heterocyclylalkyl groups may be substituted at the alkyl, the heterocyclyl, or both the alkyl and the heterocyclyl portions of the group. Representative heterocylylalkyl groups include but are not limited to 4-ethyl-morpholinyl, 4-propylmorpholinyl, furan-2-yl methyl, furan-3-yl methyl, pyridine-3-yl methyl, (tetrahydro-2H-pyran-4-yl)methyl, (tetrahydro-2H-pyran-4-yl) ethyl, tetrahydrofuran-2-yl methyl, tetrahydrofuran-2-yl ethyl, and indol-2-yl propyl.

A "halogen" is fluorine, chlorine, bromine or iodine.

A "hydroxyalkyl" group is an alkyl group as described above substituted with one or more hydroxy groups.

An "alkoxy" group is —O-(alkyl), wherein alkyl is defined above.

An "alkoxyalkyl" group is -(alkyl)-O-(alkyl), wherein alkyl is defined above.

An "amino" group is a radical of the formula: —NH$_2$.

An "alkylamino" group is a radical of the formula: —NH-alkyl or —N(alkyl)$_2$, wherein each alkyl is independently as defined above.

A "carboxy" group is a radical of the formula: —C(O)OH.

An "aminocarbonyl" group is a radical of the formula: —C(O)N(R$^\#$)$_2$, —C(O)NH(R$^\#$) or —C(O)NH$_2$, wherein each R$^\#$ is independently a substituted or unsubstituted alkyl, cycloalkyl, aryl, aralkyl, heterocyclyl or heterocyclyl group as defined herein.

An "acylamino" group is a radical of the formula: —NHC(O)(R$^\#$) or —N(alkyl)C(O)(R$^\#$), wherein each alkyl and R$^\#$ are independently as defined above.

An "alkylsulfonylamino" group is a radical of the formula: —NHSO$_2$(R$^\#$) or —N(alkyl)SO$_2$(R$^\#$), wherein each alkyl and R$^\#$ are defined above.

A "urea" group is a radical of the formula: —N(alkyl)C(O)N(R$^\#$)$_2$, —N(alkyl)C(O)NH(R$^\#$), —N(alkyl)C(O)NH$_2$, —NHC(O)N(R$^\#$)$_2$, —NHC(O)NH(R$^\#$), or —NH(CO)NHR$^\#$, wherein each alkyl and R$^\#$ are independently as defined above.

When the groups described herein, with the exception of alkyl group, are said to be "substituted," they may be substituted with any appropriate substituent or substituents. Illustrative examples of substituents are those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonato; phosphine; thiocarbonyl; sulfonyl; sulfone; sulfonamide; ketone; aldehyde; ester; urea; urethane; oxime; hydroxyl amine; alkoxyamine; aralkoxyamine; N-oxide; hydrazine; hydrazide; hydrazone; azide; isocyanate; isothiocyanate; cyanate; thiocyanate; oxygen (=O); B(OH)$_2$, O(alkyl)aminocarbonyl; cycloalkyl, which may be monocyclic or fused or non-fused polycyclic (e.g., cyclopropyl, cyclobutyl, cyclopentyl, or cyclohexyl), or a heterocyclyl, which may be monocyclic or fused or non-fused polycyclic (e.g., pyrrolidyl, piperidyl, piperazinyl, morpholinyl, or thiazinyl); monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl) aryloxy; aralkyloxy; heterocyclyloxy; and heterocyclyl alkoxy.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the TOR kinase inhibitors include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art, see for example, *Remington's Pharmaceutical Sciences*, 18$^{th}$ eds., Mack Publishing, Easton Pa. (1990) or *Remington: The Science and Practice of Pharmacy*, 19$^{th}$ eds., Mack Publishing, Easton Pa. (1995).

As used herein and unless otherwise indicated, the term "clathrate" means a TOR kinase inhibitor, or a salt thereof, in the form of a crystal lattice that contains spaces (e.g., channels) that have a guest molecule (e.g., a solvent or water) trapped within or a crystal lattice wherein a TOR kinase inhibitor is a guest molecule.

As used herein and unless otherwise indicated, the term "solvate" means a TOR kinase inhibitor, or a salt thereof, that further includes a stoichiometric or non-stoichiometric amount of a solvent bound by non-covalent intermolecular forces. In one embodiment, the solvate is a hydrate.

As used herein and unless otherwise indicated, the term "hydrate" means a TOR kinase inhibitor, or a salt thereof, that further includes a stoichiometric or non-stoichiometric amount of water bound by non-covalent intermolecular forces.

As used herein and unless otherwise indicated, the term "prodrug" means a TOR kinase inhibitor derivative that can hydrolyze, oxidize, or otherwise react under biological conditions (in vitro or in vivo) to provide an active compound, particularly a TOR kinase inhibitor. Examples of prodrugs include, but are not limited to, derivatives and metabolites of a TOR kinase inhibitor that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by *Burger's Medicinal Chemistry and Drug Discovery* 6th ed. (Donald J. Abraham ed., 2001, Wiley) and *Design and Application of Prodrugs* (H. Bundgaard ed., 1985, Harwood Academic Publishers Gmfh).

As used herein and unless otherwise indicated, the term "stereoisomer" or "stereomerically pure" means one stereoisomer of a TOR kinase inhibitor that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The TOR kinase inhibitors can have chiral centers and can occur as racemates, individual enantiomers or diastereomers, and mixtures thereof. All such isomeric forms are included within the embodiments disclosed herein, including mixtures thereof. The use of stereomerically pure forms of such TOR kinase inhibitors, as well as the use of mixtures of those forms are encompassed by the embodiments disclosed herein. For example, mixtures comprising equal or unequal amountsv of the enantiomers of a particular TOR kinase inhibitor may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, N.Y., 1962); and Wilen, S. H., *Tables of Resolving Agents and Optical Resolutions* p. 268 (E. L. Eliel, Ed., Univ. of Notre Dame Press, Notre Dame, Ind., 1972).

It should also be noted the TOR kinase inhibitors can include E and Z isomers, or a mixture thereof, and cis and trans isomers or a mixture thereof. In certain embodiments, the TOR kinase inhibitors are isolated as either the cis or trans isomer. In other embodiments, the TOR kinase inhibitors are a mixture of the cis and trans isomers.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

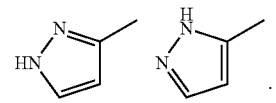

As readily understood by one skilled in the art, a wide variety of functional groups and other structures may exhibit tautomerism and all tautomers of the TOR kinase inhibitors are within the scope of the present invention.

It should also be noted the TOR kinase inhibitors can contain unnatural proportions of atomic isotopes at one or more of the atoms. For example, the compounds may be radiolabeled with radioactive isotopes, such as for example tritium ($^3$H), iodine-125 ($^{125}$I), sulfur-35 ($^{35}$S), or carbon-14 ($^{14}$C), or may be isotopically enriched, such as with deuterium ($^2$H), carbon-13 ($^{13}$C), or nitrogen-15 ($^{15}$N). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer and inflammation therapeutic agents, research reagents, e.g., binding assay reagents, and diagnostic agents, e.g., in vivo imaging agents. All isotopic variations of the TOR kinase inhibitors as described herein, whether radioactive or not, are intended to be encompassed within the scope of the embodiments provided herein. In some embodiments, there are provided isotopologues of the TOR kinase inhibitors, for example, the isotopologues are deuterium, carbon-13, or nitrogen-15 enriched TOR kinase inhibitors.

"Treating" as used herein, means an alleviation, in whole or in part, of symptoms associated with a disorder or disease (e.g., cancer or a tumor syndrome), or slowing, or halting of further progression or worsening of those symptoms.

"Preventing" as used herein, means the prevention of the onset, recurrence or spread, in whole or in part, of the disease or disorder (e.g., cancer), or a symptom thereof.

The term "effective amount" in connection with an TOR kinase inhibitor means an amount capable of alleviating, in whole or in part, symptoms associated with cancer, for example prostate cancer, lung cancer, colon cancer, glioma or breast cancer, or slowing or halting further progression or worsening of those symptoms, or preventing or providing prophylaxis for cancer, in a subject at risk for cancer, for example prostate cancer, lung cancer, colon cancer, glioma or breast cancer. The effective amount of the TOR kinase inhibitor, for example in a pharmaceutical composition, may be at a level that will exercise the desired effect; for example, about 0.005 mg/kg of a subject's body weight to about 100 mg/kg of a patient's body weight in unit dosage for both oral and parenteral administration. As will be apparent to those skilled in the art, it is to be expected that the effective amount of a TOR kinase inhibitor disclosed herein may vary depending on the severity of the indication being treated.

The terms "patient" and "subject" as used herein include an animal, including, but not limited to, an animal such as a cow, monkey, horse, sheep, pig, chicken, turkey, quail, cat, dog, mouse, rat, rabbit or guinea pig, in one embodiment a mammal, in another embodiment a human. In one embodiment, a "patient" or "subject" is a human having a disease provided herein, such as a disease associated with a TOR kinase. In another embodiment, a "patient" or "subject" is a human having a disease provided herein, such as a cancer treatable by inhibition of phosphorylation of PRAS40, GSK3β and/or p70S6K1.

As used herein "reduced level" or "inhibition" means a reduction in level relative to levels observed prior to administration of a TOR kinase inhibitor. In one embodiment the reduction is 10%-50% or 50%-100%. In some embodiments, the reduction is 20%, 30%, 40%, 50%, 60%, 70%, 80%, 90% or 100% (complete inhibition) relative to prior to administration of a TOR kinase inhibitor In the context of cancer, for example prostate cancer, lung cancer, colon cancer, glioma or breast cancer, inhibition may be assessed by delayed appearance of primary or secondary tumors, slowed development of primary or secondary tumors, decreased occurrence of primary or secondary tumors, slowed or decreased severity of secondary effects of disease, arrested tumor growth and regression of tumors, among others. In the extreme, complete inhibition, is referred to herein as prevention or chemoprevention. In this context, the term "prevention" includes either preventing the onset of clinically evident cancer, carcinoma or tumor altogether or preventing the onset of a preclinically evident stage of cancer, carcinoma or tumor in individuals at risk. Also intended to be encompassed by this definition is the prevention of transformation into malignant cells or to arrest or reverse the progression of premalignant cells to malignant cells. This includes prophylactic treatment of those at risk of developing the cancer, carcinoma or tumor.

5.2 TOR Kinase Inhibitors

The compounds provided herein are generally referred to as TOR kinase inhibitors or "TORKi." In a specific embodiment, the TOR kinase inhibitors do not include rapamycin or rapamycin analogs (rapalogs). In certain embodiments, compounds provided herein are also DNA-PK inhibitors or "DNA-PKi."

In one embodiment, the TOR kinase inhibitors include compounds having the following formula (I):

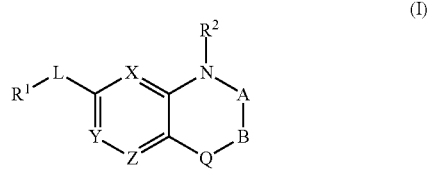

(I)

and pharmaceutically acceptable salts, clathrates, solvates, stereoisomers, tautomers, and prodrugs thereof, wherein:

X, Y and Z are at each occurrence independently N or $CR^3$, wherein at least one of X, Y and Z is N and at least one of X, Y and Z is $CR^3$;

-A-B-Q- taken together form —$CHR^4C(O)NH$—, —$C(O)CHR^4NH$—, —$C(O)NH$—, —$CH_2C(O)O$—, —$C(O)CH_2O$—, —$C(O)O$— or $C(O)NR^3$;

L is a direct bond, NH or O;

$R^1$ is H, substituted or unsubstituted $C_{1-8}$alkyl, substituted or unsubstituted $C_{2-8}$alkenyl, substituted or unsubstituted aryl, substituted or unsubstituted heteroaryl, substituted or unsubstituted cycloalkyl or substituted or unsubstituted heterocyclylalkyl;

$R^2$ is H, substituted or unsubstituted $C_{1-8}$alkyl, substituted or unsubstituted aryl, substituted or unsubstituted heteroaryl, substituted or unsubstituted cycloalkyl, or substituted or unsubstituted heterocyclylalkyl;

$R^3$ is H, substituted or unsubstituted $C_{1-8}$alkyl, substituted or unsubstituted aryl, substituted or unsubstituted heteroaryl, substituted or unsubstituted cycloalkyl, substituted or unsubstituted heterocyclylalkyl, —$NHR^4$ or —$N(R^4)_2$; and $R^4$ is at each occurrence independently substituted or unsubstituted $C_{1-8}$alkyl, substituted or unsubstituted aryl, substituted or unsubstituted heteroaryl, substituted or unsubstituted cycloalkyl, or substituted or unsubstituted heterocyclylalkyl.

In one embodiment, the TOR kinase inhibitors of formula (I) are those wherein -A-B-Q- taken together form —$CH_2C(O)NH$—.

In another embodiment, the TOR kinase inhibitors of formula (I) are those wherein -A-B-Q- taken together form —$C(O)CH_2NH$—.

In another embodiment, the TOR kinase inhibitors of formula (I) are those wherein -A-B-Q- taken together form —$C(O)NH$—.

In another embodiment, the TOR kinase inhibitors of formula (I) are those wherein -A-B-Q- taken together form —$CH_2C(O)O$—.

In another embodiment, the TOR kinase inhibitors of formula (I) are those wherein -A-B-Q- taken together form —$C(O)CH_2O$—.

In another embodiment, the TOR kinase inhibitors of formula (I) are those wherein -A-B-Q- taken together form —$C(O)O$—.

In another embodiment, the TOR kinase inhibitors of formula (I) are those wherein -A-B-Q- taken together form —$C(O)NR^3$—.

In another embodiment, the TOR kinase inhibitors of formula (I) are those wherein Y is $CR^3$.

In another embodiment, the TOR kinase inhibitors of formula (I) are those wherein X and Z are N and Y is $CR^3$.

In another embodiment, the TOR kinase inhibitors of formula (I) are those wherein X and Z are N and Y is CH.

In another embodiment, the TOR kinase inhibitors of formula (I) are those wherein X and Z are CH and Y is N.

In another embodiment, the TOR kinase inhibitors of formula (I) are those wherein Y and Z are CH and X is N.

In another embodiment, the TOR kinase inhibitors of formula (I) are those wherein X and Y are CH and Z is N.

In another embodiment, the TOR kinase inhibitors of formula (I) are those wherein $R^1$ is substituted aryl, such as substituted phenyl.

In another embodiment, the TOR kinase inhibitors of formula (I) are those wherein $R^1$ is substituted or unsubstituted aryl, such as substituted or unsubstituted phenyl or substituted or unsubstituted naphthyl.

In another embodiment, the TOR kinase inhibitors of formula (I) are those wherein $R^1$ is substituted or unsubstituted heteroaryl, such as substituted or unsubstituted quinoline, substituted or unsubstituted pyridine, substituted or unsubstituted pyrimidine, substituted or unsubstituted indole, or substituted or unsubstituted thiophene.

In another embodiment, the TOR kinase inhibitors of formula (I) are those wherein $R^1$ is H.

In another embodiment, the TOR kinase inhibitors of formula (I) are those wherein $R^2$ is substituted $C_{1-8}$alkyl.

In another embodiment, the TOR kinase inhibitors of formula (I) are those wherein $R^2$ is methyl or ethyl substituted with substituted or unsubstituted aryl, substituted or unsubstituted heteroaryl, substituted or unsubstituted cycloalkyl, or substituted or unsubstituted heterocyclylalkyl.

In another embodiment, the TOR kinase inhibitors of formula (I) are those wherein $R^2$ is substituted or unsubstituted cycloalkyl or substituted or unsubstituted heterocyclylalkyl.

In another embodiment, the TOR kinase inhibitors of formula (I) are those wherein $R^2$ is substituted or unsubstituted aryl, such as substituted or unsubstituted phenyl.

In another embodiment, the TOR kinase inhibitors of formula (I) are those wherein $R^2$ is H.

In another embodiment, the TOR kinase inhibitors of formula (I) are those wherein L is a direct bond.

In another embodiment, the TOR kinase inhibitors of formula (I) are those wherein -A-B-Q- taken together form —C(O)NH—, X and Z are N and Y is CH, $R^1$ is substituted or unsubstituted aryl or substituted or unsubstituted heteroaryl, L is a direct bond, and $R^2$ is substituted or unsubstituted $C_{1-8}$alkyl.

In another embodiment, the TOR kinase inhibitors of formula (I) are those wherein -A-B-Q- taken together form —C(O)NH—, X and Z are N and Y is CH, $R^1$ is substituted or unsubstituted aryl, L is a direct bond, and $R^2$ is substituted or unsubstituted $C_{1-8}$alkyl.

In another embodiment, the TOR kinase inhibitors of formula (I) are those wherein -A-B-Q- taken together form —C(O)NH—, X and Z are N and Y is CH, $R^1$ is substituted or unsubstituted aryl, and $R^2$ is $C_{1-8}$alkyl substituted with one or more substituents selected from alkoxy, amino, hydroxy, cycloalkyl, or heterocyclylalkyl.

In another embodiment, the TOR kinase inhibitors of formula (I) are those wherein -A-B-Q- taken together form —C(O)NH—, X and Z are N and Y is CH, $R^1$ is substituted or unsubstituted aryl, and $R^2$ is substituted or unsubstituted cycloalkyl, or substituted or unsubstituted heterocyclylalkyl.

In another embodiment, the TOR kinase inhibitors of formula (I) are those wherein -A-B-Q- taken together form —C(O)NH—, X and Z are N and Y is CH, $R^1$ is substituted phenyl, L is a direct bond, and $R^2$ is substituted $C_{1-8}$alkyl.

In another embodiment, the TOR kinase inhibitors of formula (I) do not include compounds wherein X and Z are both N and Y is CH, -A-B-Q- is —C(O)NH—, L is a direct bond, $R^1$ is substituted or unsubstituted aryl or substituted or unsubstituted heteroaryl, and $R^2$ is $C_{1-8}$alkyl substituted with substituted or unsubstituted aryl or substituted or unsubstituted heteroaryl.

In another embodiment, the TOR kinase inhibitors of formula (I) do not include compounds wherein X and Z are both N and Y is CH, -A-B-Q- is —C(O)NH—, L is a direct bond, $R^1$ is phenyl, naphthyl, indanyl or biphenyl, each of which may be optionally substituted with one or more substituents independently selected from the group consisting substituted or unsubstituted $C_{1-8}$alkyl, substituted or unsubstituted $C_{2-8}$alkenyl, substituted or unsubstituted aryl, substituted or unsubstituted cycloalkyl or substituted or unsubstituted heterocyclylalkyl.

In another embodiment, the TOR kinase inhibitors of formula (I) do not include compounds wherein X and Z are both N and Y is CH, -A-B-Q- is —C(O)NH—, L is a direct bond, $R^1$ is phenyl, naphthyl or biphenyl, each of which may be optionally substituted with one or more substituents each independently selected from the group consisting of $C_{1-4}$alkyl, amino, amino$C_{1-12}$alkyl, halogen, hydroxy, hydroxy$C_{1-4}$alkyl, $C_{1-4}$alkyloxy$C_{1-4}$alkyl, —CF$_3$, $C_{1-12}$alkoxy, aryloxy, aryl$C_{1-12}$alkoxy, —CN, —OCF$_3$, —COR$_g$, —COOR$_g$, —CONR$_g$R$_h$, —NR$_g$COR$_h$, —SO$_2$R$_g$, —SO$_3$R$_g$ or —SO$_2$NR$_g$R$_h$, wherein each R$_g$ and R$_h$ are independently selected from the group consisting of hydrogen, $C_{1-4}$alkyl, $C_{3-6}$cycloalkyl, aryl, aryl$C_{1-6}$alkyl, heteroaryl or heteroaryl$C_{1-6}$alkyl; or A is a 5- to 6-membered monocyclic heteroaromatic ring having from one, two, three or four heteroatoms independently selected from the group consisting of N, O and S, that monocyclic heteroaromatic ring may be optionally substituted with one or more substituents each independently selected from the group consisting of $C_{1-6}$alkyl, amino, amino$C_{1-12}$alkyl, halogen, hydroxy, hydroxy$C_{1-4}$alkyl, $C_{1-4}$alkyloxy$C_{1-4}$alkyl, $C_{1-12}$alkoxy, aryloxy, aryl $C_{1-12}$alkoxy, —CN, —CF$_3$, —OCF$_3$, —COR$_i$, —COOR$_i$, —CONR$_i$R$_j$, —NR$_i$COR$_j$, —NR$_i$SO$_2$R$_j$, —SO$_2$R$_i$, —SO$_3$R$_i$ or —SO$_2$NR$_i$R$_j$, wherein each R$_i$ and R$_j$ are independently selected from the group consisting of hydrogen, $C_{1-4}$ alkyl, $C_{3-6}$cycloalkyl, aryl, aryl$C_{1-6}$alkyl, heteroaryl or heteroaryl$C_{1-6}$alkyl; or A is a 8- to 10 membered bicyclic heteroaromatic ring from one, two, three or four heteroatoms selected from the group consisting of N, O and S, and may be optionally substituted with one, two or three substituents each independently selected from the group consisting of $C_{1-6}$alkyl, amino, amino$C_{1-12}$alkyl, halogen, hydroxy, hydroxy$C_{1-4}$alkyl, $C_{1-4}$alkyloxy$C_{1-4}$alkyl, $C_{1-12}$alkoxy, aryloxy, aryl $C_{1-12}$alkoxy, —CN, —CF$_3$, —OCF$_3$, —COR$_k$, —COOR$_k$, —CONR$_k$R$_l$, —NR$_k$COR$_l$, —NR$_k$SO$_2$R$_l$, —SO$_2$R$_k$, —SO$_3$R$_k$ or —SO$_2$NR$_k$R$_l$, wherein each R$_k$ and R$_l$ are independently selected from the group consisting of hydrogen, $C_{1-4}$ alkyl, $C_{3-6}$ cycloalkyl, aryl, aryl$C_{1-6}$alkyl, heteroaryl or heteroaryl$C_{1-6}$alkyl, and $R^2$ is $C_{1-8}$alkyl substituted with substituted or unsubstituted aryl or substituted or unsubstituted heteroaryl.

In another embodiment, the TOR kinase inhibitors of formula (I) do not include compounds wherein X and Y are both N and Z is CH, -A-B-Q- is —C(O)NH—, L is a direct bond, $R^1$ is substituted or unsubstituted phenyl or substituted or unsubstituted heteroaryl, and $R^2$ is substituted or unsubstituted methyl, unsubstituted ethyl, unsubstituted propyl, or an acetamide.

In another embodiment, the TOR kinase inhibitors of formula (I) do not include compounds wherein X and Y are both N and Z is CH, -A-B-Q- is —C(O)NH—, L is a direct bond, $R^1$ is substituted or unsubstituted phenyl or substituted or unsubstituted heteroaryl, and $R^2$ is an acetamide.

In another embodiment, the TOR kinase inhibitors of formula (I) do not include compounds wherein X is N and Y and Z are both CH, -A-B-Q- is —C(O)NH—, L is a direct bond, $R^1$ is a (2,5'-Bi-1H-benzimidazole)-5-carboxamide, and $R^2$ is H.

In another embodiment, the TOR kinase inhibitors of formula (I) do not include compounds wherein one of X and Z is CH and the other is N, Y is CH, -A-B-Q- is —C(O)NH—, L is a direct bond, $R^1$ is unsubstituted pyridine, and $R^2$ is H, methyl or substituted ethyl.

In another embodiment, the TOR kinase inhibitors of formula (I) do not include compounds wherein X and Z are both N and Y is CH, -A-B-Q- is —C(O)NH—, $R^1$ is H, $C_{1-8}$alkyl, $C_{2-8}$alkenyl, aryl or cycloalkyl, and L is NH.

In another embodiment, the TOR kinase inhibitors of formula (I) do not include compounds wherein X and Z are both N and Y is CH, -A-B-Q- is —C(O)NR$^3$—, $R^2$ is H, substituted or unsubstituted $C_{1-8}$alkyl, substituted or unsubstituted phenyl, substituted or unsubstituted cycloalkyl, or substituted or unsubstituted heterocyclylalkyl, and L is NH.

In another embodiment, the TOR kinase inhibitors of formula (I) do not include compounds wherein $R^1$ is a substituted or unsubstituted oxazolidinone.

In another embodiment, the TOR kinase inhibitors of formula (I) do not include one or more of the following compounds: 1,7-dihydro-2-phenyl-8H-Purin-8-one, 1,2-dihydro-3-phenyl-6H-Imidazo[4,5-e]-1,2,4-triazin-6-one, 1,3-dihydro-6-(4-pyridinyl)-2H-Imidazo[4,5-b]pyridin-2-one, 6-(1,3-benzodioxol-5-yl)-1,3-dihydro-1-[(1S)-1-phenylethyl]-2H-Imidazo[4,5-b]pyrazin-2-one, 3-[2,3-dihydro-2-oxo-3-(4-pyridinylmethyl)-1H-imidazo[4,5-b]pyrazin-5-yl]-Benzamide, 1-[2-(dimethylamino)ethyl]-1,3-dihydro-6-(3,4,5-trimethoxyphenyl)-2H-Imidazo[4,5-b]pyrazin-2-one, N-[5-(1,1-dimethylethyl)-2-methoxyphenyl]-N'-[4-(1,2,3,4-tetrahydro-2-oxopyrido[2,3-b]pyrazin-7-yl)-1-naphthalenyl]-Urea, N-[4-(2,3-dihydro-2-oxo-1H-imidazo[4,5-b]pyridin-6-yl)-1-naphthalenyl]-N'-[5-(1,1-dimethylethyl)-2-methoxyphenyl]-Urea, 1,3-dihydro-5-phenyl-2H-Imidazo[4,5-b]pyrazin-2-one, 1,3-dihydro-5-phenoxy-2H-Imidazo[4,5-b]pyridin-2-one, 1,3-dihydro-1-methyl-6-phenyl-2H-Imidazo[4,5-b]pyridin-2-one, 1,3-dihydro-5-(1H-imidazol-1-yl) 2H-Imidazo[4,5-b]pyridin-2-one, 6-(2,3-dihydro-2-oxo-1H-imidazo[4,5-b]pyridin-6-yl)-8-methyl-2(1H)-Quinolinone and 7,8-dihydro-8-oxo-2-phenyl-9H-purine-9-acetic acid.

In one embodiment, the TOR kinase inhibitors include compounds having the following formula (Ia):

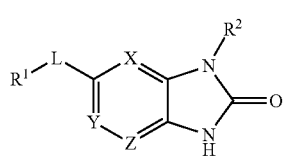

(Ia)

and pharmaceutically acceptable salts, clathrates, solvates, stereoisomers, tautomers, and prodrugs thereof, wherein:

L is a direct bond, NH or O;
Y is N or $CR^3$;
$R^1$ is H, substituted or unsubstituted $C_{1-8}$alkyl, substituted or unsubstituted $C_{2-8}$alkenyl, substituted or unsubstituted aryl, substituted or unsubstituted heteroaryl, substituted or unsubstituted cycloalkyl or substituted or unsubstituted heterocyclylalkyl;
$R^2$ is H, substituted or unsubstituted $C_{1-8}$alkyl, substituted or unsubstituted aryl, substituted or unsubstituted heteroaryl, substituted or unsubstituted cycloalkyl, or substituted or unsubstituted heterocyclylalkyl;
$R^3$ is H, substituted or unsubstituted $C_{1-8}$alkyl, substituted or unsubstituted aryl, substituted or unsubstituted heteroaryl, substituted or unsubstituted cycloalkyl, substituted or unsubstituted heterocyclylalkyl, —$NHR^4$ or —$N(R^4)_2$; and
$R^4$ is at each occurrence independently substituted or unsubstituted $C_{1-8}$alkyl, substituted or unsubstituted aryl, substituted or unsubstituted heteroaryl, substituted or unsubstituted cycloalkyl, or substituted or unsubstituted heterocyclylalkyl.

In one embodiment, the TOR kinase inhibitors of formula (Ia) are those wherein $R^1$ is substituted aryl, such as substituted phenyl.

In another embodiment, the TOR kinase inhibitors of formula (Ia) are those wherein $R^1$ is substituted or unsubstituted aryl, such as substituted or unsubstituted phenyl or substituted or unsubstituted naphthyl.

In another embodiment, the TOR kinase inhibitors of formula (Ia) are those wherein $R^1$ is substituted or unsubstituted heteroaryl, such as substituted or unsubstituted quinoline, substituted or unsubstituted pyridine, substituted or unsubstituted pyrimidine, substituted or unsubstituted indole, or substituted or unsubstituted thiophene.

In another embodiment, the TOR kinase inhibitors of formula (Ia) are those wherein $R^1$ is H.

In another embodiment, the TOR kinase inhibitors of formula (Ia) are those wherein $R^2$ is substituted $C_{1-8}$alkyl.

In another embodiment, the TOR kinase inhibitors of formula (Ia) are those wherein $R^2$ is methyl or ethyl substituted with substituted or unsubstituted aryl, substituted or unsubstituted heteroaryl, substituted or unsubstituted cycloalkyl, or substituted or unsubstituted heterocyclylalkyl.

In another embodiment, the TOR kinase inhibitors of formula (Ia) are those wherein $R^2$ is substituted or unsubstituted cycloalkyl or substituted or unsubstituted heterocyclylalkyl.

In another embodiment, the TOR kinase inhibitors of formula (Ia) are those wherein $R^2$ is substituted or unsubstituted aryl, such as substituted or unsubstituted phenyl.

In another embodiment, the TOR kinase inhibitors of formula (Ia) are those wherein $R^2$ is H.

In another embodiment, the TOR kinase inhibitors of formula (Ia) are those wherein Y is CH.

In another embodiment, the TOR kinase inhibitors of formula (Ia) are those wherein L is a direct bond.

In another embodiment, the TOR kinase inhibitors of formula (Ia) are those wherein $R^1$ is substituted or unsubstituted aryl and $R^2$ is unsubstituted $C_{1-8}$alkyl.

In another embodiment, the TOR kinase inhibitors of formula (Ia) are those wherein $R^1$ is substituted or unsubstituted aryl and $R^2$ is $C_{1-8}$alkyl substituted with one or more substituents selected from alkoxy, amino, hydroxy, cycloalkyl, or heterocyclylalkyl.

In another embodiment, the TOR kinase inhibitors of formula (Ia) are those wherein $R^1$ is substituted or unsubstituted aryl and $R^2$ is substituted or unsubstituted cycloalkyl, or substituted or unsubstituted heterocyclylalkyl.

In another embodiment, the TOR kinase inhibitors of formula (Ia) do not include compounds wherein Y is CH, L is a direct bond, $R^1$ is substituted or unsubstituted aryl or substituted or unsubstituted heteroaryl, and $R^2$ is $C_{1-8}$alkyl substituted with substituted or unsubstituted aryl or substituted or unsubstituted heteroaryl.

In one embodiment, the TOR kinase inhibitors include compounds having the following formula (Ib):

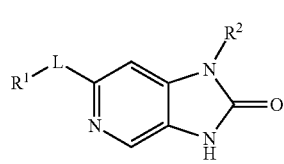

(Ib)

and pharmaceutically acceptable salts, clathrates, solvates, stereoisomers, tautomers, and prodrugs thereof, wherein:

L is a direct bond, NH or O;
$R^1$ is H, substituted or unsubstituted $C_{1-8}$alkyl, substituted or unsubstituted $C_{2-8}$alkenyl, substituted or unsubstituted aryl, substituted or unsubstituted heteroaryl, substituted or unsubstituted cycloalkyl or substituted or unsubstituted heterocyclylalkyl; and $R^2$ is H, substituted or unsubstituted $C_{1-8}$alkyl, substituted or unsubstituted aryl, substituted or unsubstituted heteroaryl, substituted or unsubstituted cycloalkyl, or substituted or unsubstituted heterocyclylalkyl.

In one embodiment, the TOR kinase inhibitors of formula (Ib) are those wherein $R^1$ is substituted aryl, such as substituted phenyl.

In another embodiment, the TOR kinase inhibitors of formula (Ib) are those wherein $R^1$ is substituted or unsubstituted aryl, such as substituted or unsubstituted phenyl or substituted or unsubstituted naphthyl.

In another embodiment, the TOR kinase inhibitors of formula (Ib) are those wherein $R^1$ is substituted or unsubstituted heteroaryl, such as substituted or unsubstituted quinoline, substituted or unsubstituted pyridine, substituted or unsubstituted pyrimidine, substituted or unsubstituted indole, or substituted or unsubstituted thiophene.

In another embodiment, the TOR kinase inhibitors of formula (Ib) are those wherein $R^1$ is H.

In another embodiment, the TOR kinase inhibitors of formula (Ib) are those wherein $R^2$ is substituted $C_{1-8}$alkyl.

In another embodiment, the TOR kinase inhibitors of formula (Ib) are those wherein $R^2$ is methyl or ethyl substituted with substituted or unsubstituted aryl, substituted or unsubstituted heteroaryl, substituted or unsubstituted cycloalkyl, or substituted or unsubstituted heterocyclylalkyl.

In another embodiment, the TOR kinase inhibitors of formula (Ib) are those wherein $R^2$ is substituted or unsubstituted cycloalkyl or substituted or unsubstituted heterocyclylalkyl.

In another embodiment, the TOR kinase inhibitors of formula (Ib) are those wherein $R^2$ is substituted or unsubstituted aryl, such as substituted or unsubstituted phenyl.

In another embodiment, the TOR kinase inhibitors of formula (Ib) are those wherein $R^2$ is H.

In another embodiment, the TOR kinase inhibitors of formula (Ib) are those wherein L is a direct bond.

In another embodiment, the TOR kinase inhibitors of formula (Ib) are those wherein $R^1$ is substituted or unsubstituted aryl and $R^2$ is unsubstituted $C_{1-8}$alkyl.

In another embodiment, the TOR kinase inhibitors of formula (Ib) are those wherein $R^1$ is substituted or unsubstituted aryl and $R^2$ is $C_{1-8}$alkyl substituted with one or more substituents selected from alkoxy, amino, hydroxy, cycloalkyl, or heterocyclylalkyl.

In another embodiment, the TOR kinase inhibitors of formula (Ib) are those wherein $R^1$ is substituted or unsubstituted aryl and $R^2$ is substituted or unsubstituted cycloalkyl, or substituted or unsubstituted heterocyclylalkyl.

In one embodiment, the TOR kinase inhibitors include compounds having the following formula (Ic):

(Ic)

and pharmaceutically acceptable salts, clathrates, solvates, stereoisomers, tautomers, and prodrugs thereof, wherein:

L is a direct bond, NH or O;

$R^1$ is H, substituted or unsubstituted $C_{1-8}$alkyl, substituted or unsubstituted $C_{2-8}$alkenyl, substituted or unsubstituted aryl, substituted or unsubstituted heteroaryl, substituted or unsubstituted cycloalkyl or substituted or unsubstituted heterocyclylalkyl; and $R^2$ is H, substituted or unsubstituted $C_{1-8}$alkyl, substituted or unsubstituted aryl, substituted or unsubstituted heteroaryl, substituted or unsubstituted cycloalkyl, or substituted or unsubstituted heterocyclylalkyl.

In one embodiment, the TOR kinase inhibitors of formula (Ic) are those wherein $R^1$ is substituted aryl, such as substituted phenyl.

In another embodiment, the TOR kinase inhibitors of formula (Ic) are those wherein $R^1$ is substituted or unsubstituted aryl, such as substituted or unsubstituted phenyl or substituted or unsubstituted naphthyl.

In another embodiment, the TOR kinase inhibitors of formula (Ic) are those wherein $R^1$ is substituted or unsubstituted heteroaryl, such as substituted or unsubstituted quinoline, substituted or unsubstituted pyridine, substituted or unsubstituted pyrimidine, substituted or unsubstituted indole, or substituted or unsubstituted thiophene.

In another embodiment, the TOR kinase inhibitors of formula (Ic) are those wherein $R^1$ is H.

In another embodiment, the TOR kinase inhibitors of formula (Ic) are those wherein $R^2$ is substituted $C_{1-8}$alkyl.

In another embodiment, the TOR kinase inhibitors of formula (Ic) are those wherein $R^2$ is methyl or ethyl substituted with substituted or unsubstituted aryl, substituted or unsubstituted heteroaryl, substituted or unsubstituted cycloalkyl, or substituted or unsubstituted heterocyclylalkyl.

In another embodiment, the TOR kinase inhibitors of formula (Ic) are those wherein $R^2$ is substituted or unsubstituted cycloalkyl or substituted or unsubstituted heterocyclylalkyl.

In another embodiment, the TOR kinase inhibitors of formula (Ic) are those wherein $R^2$ is substituted or unsubstituted aryl, such as substituted or unsubstituted phenyl.

In another embodiment, the TOR kinase inhibitors of formula (Ic) are those wherein $R^2$ is H.

In another embodiment, the TOR kinase inhibitors of formula (Ic) are those wherein L is a direct bond.

In another embodiment, the TOR kinase inhibitors of formula (Ic) are those wherein $R^1$ is substituted or unsubstituted aryl and $R^2$ is unsubstituted $C_{1-8}$alkyl.

In another embodiment, the TOR kinase inhibitors of formula (Ic) are those wherein $R^1$ is substituted or unsubstituted aryl and $R^2$ is $C_{1-8}$alkyl substituted with one or more substituents selected from alkoxy, amino, hydroxy, cycloalkyl, or heterocyclylalkyl.

In another embodiment, the TOR kinase inhibitors of formula (Ic) are those wherein $R^1$ is substituted or unsubstituted aryl and $R^2$ is substituted or unsubstituted cycloalkyl, or substituted or unsubstituted heterocyclylalkyl.

In one embodiment, the TOR kinase inhibitors include compounds having the following formula (Id):

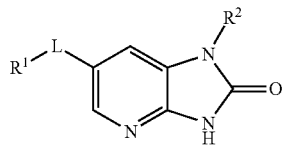
(Id)

and pharmaceutically acceptable salts, clathrates, solvates, stereoisomers, tautomers, and prodrugs thereof, wherein:

L is a direct bond, NH or O;

$R^1$ is H, substituted or unsubstituted $C_{1-8}$alkyl, substituted or unsubstituted $C_{2-8}$alkenyl, substituted or unsubstituted aryl, substituted or unsubstituted heteroaryl, substituted or unsubstituted cycloalkyl or substituted or unsubstituted heterocyclylalkyl; and $R^2$ is H, substituted or unsubstituted $C_{1-8}$alkyl, substituted or unsubstituted aryl, substituted or unsubstituted heteroaryl, substituted or unsubstituted cycloalkyl, or substituted or unsubstituted heterocyclylalkyl.

In one embodiment, the TOR kinase inhibitors of formula (Id) are those wherein $R^1$ is substituted aryl, such as substituted phenyl.

In another embodiment, the TOR kinase inhibitors of formula (Id) are those wherein $R^1$ is substituted or unsubstituted aryl, such as substituted or unsubstituted phenyl or substituted or unsubstituted naphthyl.

In another embodiment, the TOR kinase inhibitors of formula (Id) are those wherein $R^1$ is substituted or unsubstituted heteroaryl, such as substituted or unsubstituted quinoline, substituted or unsubstituted pyridine, substituted or unsubstituted pyrimidine, substituted or unsubstituted indole, or substituted or unsubstituted thiophene.

In another embodiment, the TOR kinase inhibitors of formula (Id) are those wherein $R^1$ is H.

In another embodiment, the TOR kinase inhibitors of formula (Id) are those wherein $R^2$ is substituted $C_{1-8}$alkyl.

In another embodiment, the TOR kinase inhibitors of formula (Id) are those wherein $R^2$ is methyl or ethyl substituted with substituted or unsubstituted aryl, substituted or unsubstituted heteroaryl, substituted or unsubstituted cycloalkyl, or substituted or unsubstituted heterocyclylalkyl.

In another embodiment, the TOR kinase inhibitors of formula (Id) are those wherein $R^2$ is substituted or unsubstituted cycloalkyl or substituted or unsubstituted heterocyclylalkyl.

In another embodiment, the TOR kinase inhibitors of formula (Id) are those wherein $R^2$ is substituted or unsubstituted aryl, such as substituted or unsubstituted phenyl.

In another embodiment, the Heteroaryl Compounds of formula (Id) are those wherein $R^2$ is H.

In another embodiment, the TOR kinase inhibitors of formula (Id) are those wherein L is a direct bond.

In another embodiment, the TOR kinase inhibitors of formula (Id) are those wherein $R^1$ is substituted or unsubstituted aryl and $R^2$ is unsubstituted $C_{1-8}$alkyl.

In another embodiment, the TOR kinase inhibitors of formula (Id) are those wherein $R^1$ is substituted or unsubstituted aryl and $R^2$ is $C_{1-8}$alkyl substituted with one or more substituents selected from alkoxy, amino, hydroxy, cycloalkyl, or heterocyclylalkyl.

In another embodiment, the TOR kinase inhibitors of formula (Id) are those wherein $R^1$ is substituted or unsubstituted aryl and $R^2$ is substituted or unsubstituted cycloalkyl, or substituted or unsubstituted heterocyclylalkyl.

In one embodiment, the TOR kinase inhibitors include compounds having the following formula (Ie):

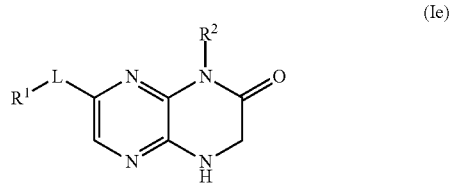

and pharmaceutically acceptable salts, clathrates, solvates, stereoisomers, tautomers, and prodrugs thereof, wherein:

L is a direct bond, NH or O;

$R^1$ is H, substituted or unsubstituted $C_{1-8}$alkyl, substituted or unsubstituted $C_{2-8}$alkenyl, substituted or unsubstituted aryl, substituted or unsubstituted heteroaryl, substituted or unsubstituted cycloalkyl or substituted or unsubstituted heterocyclylalkyl; and $R^2$ is H, substituted or unsubstituted $C_{1-8}$alkyl, substituted or unsubstituted aryl, substituted or unsubstituted heteroaryl, substituted or unsubstituted cycloalkyl, or substituted or unsubstituted heterocyclylalkyl.

In one embodiment, the TOR kinase inhibitors of formula (Ie) are those wherein $R^1$ is substituted aryl, such as substituted phenyl.

In another embodiment, the TOR kinase inhibitors of formula (Ie) are those wherein $R^1$ is substituted or unsubstituted aryl, such as substituted or unsubstituted phenyl or substituted or unsubstituted naphthyl.

In another embodiment, the TOR kinase inhibitors of formula (Ie) are those wherein $R^1$ is substituted or unsubstituted heteroaryl, such as substituted or unsubstituted quinoline, substituted or unsubstituted pyridine, substituted or unsubstituted pyrimidine, substituted or unsubstituted indole, or substituted or unsubstituted thiophene.

In another embodiment, the TOR kinase inhibitors of formula (Ie) are those wherein $R^1$ is H.

In another embodiment, the TOR kinase inhibitors of formula (Ie) are those wherein $R^2$ is substituted $C_{1-8}$alkyl.

In another embodiment, the TOR kinase inhibitors of formula (Ie) are those wherein $R^2$ is methyl or ethyl substituted with substituted or unsubstituted aryl, substituted or unsubstituted heteroaryl, substituted or unsubstituted cycloalkyl, or substituted or unsubstituted heterocyclylalkyl.

In another embodiment, the TOR kinase inhibitors of formula (Ie) are those wherein $R^2$ is substituted or unsubstituted cycloalkyl or substituted or unsubstituted heterocyclylalkyl.

In another embodiment, the TOR kinase inhibitors of formula (Ie) are those wherein $R^2$ is substituted or unsubstituted aryl, such as substituted or unsubstituted phenyl.

In another embodiment, the TOR kinase inhibitors of formula (Ie) are those wherein $R^2$ is H.

In another embodiment, the TOR kinase inhibitors of formula (Ie) are those wherein L is a direct bond.

In another embodiment, the TOR kinase inhibitors of formula (Ie) are those wherein $R^1$ is substituted or unsubstituted aryl and $R^2$ is unsubstituted $C_{1-8}$alkyl.

In another embodiment, the TOR kinase inhibitors of formula (Ie) are those wherein $R^1$ is substituted or unsubstituted aryl and $R^2$ is $C_{1-8}$alkyl substituted with one or more substituents selected from alkoxy, amino, hydroxy, cycloalkyl, or heterocyclylalkyl.

In another embodiment, the TOR kinase inhibitors of formula (Ie) are those wherein $R^1$ is substituted or unsubstituted aryl and $R^2$ is substituted or unsubstituted cycloalkyl, or substituted or unsubstituted heterocyclylalkyl.

In one embodiment, the TOR kinase inhibitors include compounds having the following formula (If):

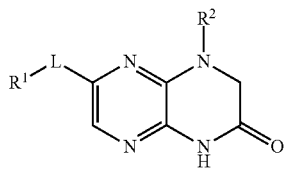

(If)

and pharmaceutically acceptable salts, clathrates, solvates, stereoisomers, tautomers, and prodrugs thereof, wherein:

L is a direct bond, NH or O;

$R^1$ is H, substituted or unsubstituted $C_{1-8}$alkyl, substituted or unsubstituted $C_{2-8}$alkenyl, substituted or unsubstituted aryl, substituted or unsubstituted heteroaryl, substituted or unsubstituted cycloalkyl or substituted or unsubstituted heterocyclylalkyl; and $R^2$ is H, substituted or unsubstituted $C_{1-8}$alkyl, substituted or unsubstituted aryl, substituted or unsubstituted heteroaryl, substituted or unsubstituted cycloalkyl, or substituted or unsubstituted heterocyclylalkyl.

In one embodiment, the TOR kinase inhibitors of formula (If) are those wherein $R^1$ is substituted aryl, such as substituted phenyl.

In another embodiment, the TOR kinase inhibitors of formula (If) are those wherein $R^1$ is substituted or unsubstituted aryl, such as substituted or unsubstituted phenyl or substituted or unsubstituted naphthyl.

In another embodiment, the TOR kinase inhibitors of formula (If) are those wherein $R^1$ is substituted or unsubstituted heteroaryl, such as substituted or unsubstituted quinoline, substituted or unsubstituted pyridine, substituted or unsubstituted pyrimidine, substituted or unsubstituted indole, or substituted or unsubstituted thiophene.

In another embodiment, the TOR kinase inhibitors of formula (If) are those wherein $R^1$ is H.

In another embodiment, the TOR kinase inhibitors of formula (If) are those wherein $R^2$ is substituted $C_{1-8}$alkyl.

In another embodiment, the TOR kinase inhibitors of formula (If) are those wherein $R^2$ is methyl or ethyl substituted with substituted or unsubstituted aryl, substituted or unsubstituted heteroaryl, substituted or unsubstituted cycloalkyl, or substituted or unsubstituted heterocyclylalkyl.

In another embodiment, the TOR kinase inhibitors of formula (If) are those wherein $R^2$ is substituted or unsubstituted cycloalkyl or substituted or unsubstituted heterocyclylalkyl.

In another embodiment, the TOR kinase inhibitors of formula (If) are those wherein $R^2$ is substituted or unsubstituted aryl, such as substituted or unsubstituted phenyl.

In another embodiment, the TOR kinase inhibitors of formula (If) are those wherein $R^2$ is H.

In another embodiment, the TOR kinase inhibitors of formula (If) are those wherein L is a direct bond.

In another embodiment, the TOR kinase inhibitors of formula (If) are those wherein $R^1$ is substituted or unsubstituted aryl and $R^2$ is unsubstituted $C_{1-8}$alkyl.

In another embodiment, the TOR kinase inhibitors of formula (If) are those wherein $R^1$ is substituted or unsubstituted aryl and $R^2$ is $C_{1-8}$alkyl substituted with one or more substituents selected from alkoxy, amino, hydroxy, cycloalkyl, or heterocyclylalkyl.

In another embodiment, the TOR kinase inhibitors of formula (If) are those wherein $R^1$ is substituted or unsubstituted aryl and $R^2$ is substituted or unsubstituted cycloalkyl, or substituted or unsubstituted heterocyclylalkyl.

In one embodiment, the TOR kinase inhibitors include compounds having the following formula (Ig):

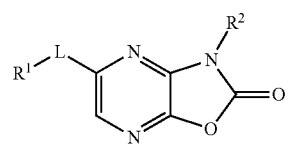

(Ig)

and pharmaceutically acceptable salts, clathrates, solvates, stereoisomers, tautomers, and prodrugs thereof, wherein:

L is a direct bond, NH or O;

$R^1$ is H, substituted or unsubstituted $C_{1-8}$alkyl, substituted or unsubstituted $C_{2-8}$alkenyl, substituted or unsubstituted aryl, substituted or unsubstituted heteroaryl, substituted or unsubstituted cycloalkyl or substituted or unsubstituted heterocyclylalkyl; and $R^2$ is H, substituted or unsubstituted $C_{1-8}$alkyl, substituted or unsubstituted aryl, substituted or unsubstituted heteroaryl, substituted or unsubstituted cycloalkyl, or substituted or unsubstituted heterocyclylalkyl.

In one embodiment, the TOR kinase inhibitors of formula (Ig) are those wherein $R^1$ is substituted aryl, such as substituted phenyl.

In another embodiment, the TOR kinase inhibitors of formula (Ig) are those wherein $R^1$ is substituted or unsubstituted aryl, such as substituted or unsubstituted phenyl or substituted or unsubstituted naphthyl.

In another embodiment, the TOR kinase inhibitors of formula (Ig) are those wherein $R^1$ is substituted or unsubstituted heteroaryl, such as substituted or unsubstituted quinoline, substituted or unsubstituted pyridine, substituted or unsubstituted pyrimidine, substituted or unsubstituted indole, or substituted or unsubstituted thiophene.

In another embodiment, the TOR kinase inhibitors of formula (Ig) are those wherein $R^1$ is H.

In another embodiment, the TOR kinase inhibitors of formula (Ig) are those wherein $R^2$ is substituted $C_{1-8}$alkyl.

In another embodiment, the TOR kinase inhibitors of formula (Ig) are those wherein $R^2$ is methyl or ethyl substituted with substituted or unsubstituted aryl, substituted or unsubstituted heteroaryl, substituted or unsubstituted cycloalkyl, or substituted or unsubstituted heterocyclylalkyl.

In another embodiment, the TOR kinase inhibitors of formula (Ig) are those wherein $R^2$ is substituted or unsubstituted cycloalkyl or substituted or unsubstituted heterocyclylalkyl.

In another embodiment, the TOR kinase inhibitors of formula (Ig) are those wherein $R^2$ is substituted or unsubstituted aryl, such as substituted or unsubstituted phenyl.

In another embodiment, the TOR kinase inhibitors of formula (Ig) are those wherein $R^2$ is H.

In another embodiment, the TOR kinase inhibitors of formula (Ig) are those wherein L is a direct bond.

In another embodiment, the TOR kinase inhibitors of formula (Ig) are those wherein $R^1$ is substituted or unsubstituted aryl and $R^2$ is unsubstituted $C_{1-8}$alkyl.

In another embodiment, the TOR kinase inhibitors of formula (Ig) are those wherein $R^1$ is substituted or unsubstituted aryl and $R^2$ is $C_{1-8}$alkyl substituted with one or more substituents selected from alkoxy, amino, hydroxy, cycloalkyl, or heterocyclylalkyl.

In another embodiment, the TOR kinase inhibitors of formula (Ig) are those wherein $R^1$ is substituted or unsubstituted aryl and $R^2$ is substituted or unsubstituted cycloalkyl, or substituted or unsubstituted heterocyclylalkyl.

Representative TOR kinase inhibitors of formula (I) include compounds from Table A.

TABLE A (S)-1-(1-hydroxy-3-methylbutan-2-yl)-6-phenyl-1H-imidazo[4,5-b]pyrazin-2(3H)-one;
1-((tetrahydro-2H-pyran-4-yl)methyl)-6-(3,4,5-trimethoxyphenyl)-1H-imidazo[4,5-b]pyrazin-2(3H)-one;
(R)-6-(naphthalen-1-yl)-1-(1-phenylethyl)-1H-imidazo[4,5-b]pyrazin-2(3H)-one;
1-(3-methoxybenzyl)-6-(4-(methylsulfonyl)phenyl)-1H-imidazo[4,5-b]pyrazin-2(3H)-one;
(S)-1-(1-phenylethyl)-6-(quinolin-5-yl)-1H-imidazo[4,5-b]pyrazin-2(3H)-one;
6-(4-hydroxyphenyl)-1-((tetrahydro-2H-pyran-4-yl)methyl)-1H-imidazo[4,5-b]pyrazin-2(3H)-one;
(S)-6-(naphthalen-1-yl)-1-(1-phenylethyl)-1H-imidazo[4,5-b]pyrazin-2(3H)-one;
(S)-1-(1-hydroxy-3-methylbutan-2-yl)-6-(5-isopropyl-2-methoxyphenyl)-1H-imidazo[4,5-b]pyrazin-2(3H)-one;
(R)-1-(1-hydroxy-3-methylbutan-2-yl)-6-phenyl-1H-imidazo[4,5-b]pyrazin-2(3H)-one;
(R)-1-(1-phenylethyl)-6-(quinolin-5-yl)-1H-imidazo[4,5-b]pyrazin-2(3H)-one;
(S)-1-(1-hydroxy-3-methylbutan-2-yl)-6-(quinolin-5-yl)-1H-imidazo[4,5-b]pyrazin-2(3H)-one;
(R)-1-(1-hydroxy-3-methylbutan-2-yl)-6-(quinolin-5-yl)-1H-imidazo[4,5-b]pyrazin-2(3H)-one;
(R)-1-(1-hydroxy-3-methylbutan-2-yl)-6-(5-isopropyl-2-methoxyphenyl)-1H-imidazo[4,5-b]pyrazin-2(3H)-one;
1-benzyl-6-(quinolin-5-yl)-1H-imidazo[4,5-b]pyrazin-2(3H)-one;
1-(4-methoxybenzyl)-6-(quinolin-5-yl)-1H-imidazo[4,5-b]pyrazin-2(3H)-one;
(R)-1-(1-phenylethyl)-1H-imidazo[4,5-b]pyrazin-2(3H)-one;
(S)-1-(1-phenylethyl)-1H-imidazo[4,5-b]pyrazin-2(3H)-one;
1-isopropyl-6-(5-isopropyl-2-methoxyphenyl)-1H-imidazo[4,5-b]pyrazin-2(3H)-one;
1-cyclohexyl-6-(5-isopropyl-2-methoxyphenyl)-1H-imidazo[4,5-b]pyrazin-2(3H)-one;
5-(quinolin-5-yl)-1H-imidazo[4,5-b]pyrazin-2(3H)-one;
1-isobutyl-6-(5-isopropyl-2-methoxyphenyl)-1H-imidazo[4,5-b]pyrazin-2(3H)-one;
1-(2-hydroxyethyl)-6-(5-isopropyl-2-methoxyphenyl)-1H-imidazo[4,5-b]pyrazin-2(3H)-one;
6-(5-isopropyl-2-methoxyphenyl)-1-(tetrahydro-2H-pyran-4-yl)-1H-imidazo[4,5-b]pyrazin-2(3H)-one;
(R)-1-(1-phenylethyl)-6-(quinolin-5-yl)-1H-imidazo[4,5-c]pyridin-2(3H)-one;
(S)-1-(1-phenylethyl)-6-(quinolin-5-yl)-1H-imidazo[4,5-c]pyridin-2(3H)-one;
3-(1-phenylethyl)-5-(quinolin-5-yl)-1H-imidazo[4,5-b]pyridin-2(3H)-one;
(R)-3-(1-phenylethyl)-5-(quinolin-5-yl)-1H-imidazo[4,5-b]pyridin-2(3H)-one;
(R)-6-(5-isopropyl-2-methoxyphenyl)-1-(3-methylbutan-2-yl)-1H-imidazo[4,5-b]pyrazin-2(3H)-one;
(S)-6-(5-isopropyl-2-methoxyphenyl)-1-(tetrahydrofuran-3-yl)-1H-imidazo[4,5-b]pyrazin-2(3H)-one;
(S)-6-(5-isopropyl-2-methoxyphenyl)-1-(3-methylbutan-2-yl)-1H-imidazo[4,5-b]pyrazin-2(3H)-one;
1-cyclopentyl-6-(5-isopropyl-2-methoxyphenyl)-1H-imidazo[4,5-b]pyrazin-2(3H)-one;
(R)-6-(5-isopropyl-2-methoxyphenyl)-1-(tetrahydrofuran-3-yl)-1H-imidazo[4,5-b]pyrazin-2(3H)-one;
1-(cyclopropylmethyl)-6-(5-isopropyl-2-methoxyphenyl)-1H-imidazo[4,5-b]pyrazin-2(3H)-one;
1-(cyclopentylmethyl)-6-(5-isopropyl-2-methoxyphenyl)-1H-imidazo[4,5-b]pyrazin-2(3H)-one;
1-(cyclohexylmethyl)-6-(5-isopropyl-2-methoxyphenyl)-1H-imidazo[4,5-b]pyrazin-2(3H)-one;
6-(5-isopropyl-2-methoxyphenyl)-1-neopentyl-1H-imidazo[4,5-b]pyrazin-2(3H)-one;
1-isopropyl-6-(3-isopropylphenyl)-1H-imidazo[4,5-b]pyrazin-2(3H)-one;
1-isopropyl-6-(2-methoxyphenyl)-1H-imidazo[4,5-b]pyrazin-2(3H)-one;
(S)-3-(1-hydroxy-3-methylbutan-2-yl)-5-(5-isopropyl-2-methoxyphenyl)-1H-imidazo[4,5-b]pyridin-2(3H)-one;
(R)-1-(2-hydroxy-1-phenylethyl)-6-(quinolin-5-yl)-1H-imidazo[4,5-b]pyrazin-2(3H)-one;
(S)-1-(2-hydroxy-1-phenylethyl)-6-(quinolin-5-yl)-1H-imidazo[4,5-b]pyrazin-2(3H)-one;
1-(1-phenylethyl)-6-(quinolin-5-yl)-1H-imidazo[4,5-b]pyrazin-2(3H)-one;
1-benzhydryl-6-(quinolin-5-yl)-1H-imidazo[4,5-b]pyrazin-2(3H)-one;
(S)-1-(1-phenylpropyl)-6-(quinolin-5-yl)-1H-imidazo[4,5-b]pyrazin-2(3H)-one;
(R)-1-(1-phenylpropyl)-6-(quinolin-5-yl)-1H-imidazo[4,5-b]pyrazin-2(3H)-one;
6-(5-isopropyl-2-methoxyphenyl)-1-(tetrahydro-2H-pyran-3-yl)-1H-imidazo[4,5-b]pyrazin-2(3H)-one;
1-(3-methoxybenzyl)-6-(quinolin-5-yl)-1H-imidazo[4,5-b]pyrazin-2(3H)-one;
(R)-1-methyl-3-(1-phenylethyl)-5-(quinolin-5-yl)-1H-imidazo[4,5-b]pyrazin-2(3H)-one;
(S)-1-methyl-3-(1-phenylethyl)-5-(quinolin-5-yl)-1H-imidazo[4,5-b]pyrazin-2(3H)-one;
1-(cyclopentylmethyl)-6-(quinolin-5-yl)-1H-imidazo[4,5-b]pyrazin-2(3H)-one;
1-(1-(2-fluorophenyl)ethyl)-6-(quinolin-5-yl)-1H-imidazo[4,5-b]pyrazin-2(3H)-one;
1-(1-(4-fluorophenyl)ethyl)-6-(quinolin-5-yl)-1H-imidazo[4,5-b]pyrazin-2(3H)-one;
1-cyclopentyl-6-(quinolin-5-yl)-1H-imidazo[4,5-b]pyrazin-2(3H)-one;
1-(1-(3-fluorophenyl)ethyl)-6-(quinolin-5-yl)-1H-imidazo[4,5-b]pyrazin-2(3H)-one;
1-(1-(3-methoxyphenyl)ethyl)-6-(quinolin-5-yl)-1H-imidazo[4,5-b]pyrazin-2(3H)-one;
1-(1-(4-methoxyphenyl)ethyl)-6-(quinolin-5-yl)-1H-imidazo[4,5-b]pyrazin-2(3H)-one;
6-(quinolin-5-yl)-1-(tetrahydro-2H-pyran-4-yl)-1H-imidazo[4,5-b]pyrazin-2(3H)-one;
6-(quinolin-5-yl)-1-(tetrahydro-2H-pyran-3-yl)-1H-imidazo[4,5-b]pyrazin-2(3H)-one;

TABLE A-continued 1-((1s,4s)-4-hydroxycyclohexyl)-6-(quinolin-5-yl)-1H-imidazo[4,5-b]pyrazin-2(3H)-one;
1-((1r,4r)-4-hydroxycyclohexyl)-6-(quinolin-5-yl)-1H-imidazo[4,5-b]pyrazin-2(3H)-one;
6-(isoquinolin-5-yl)-1-(1-phenylethyl)-1H-imidazo[4,5-b]pyrazin-2(3H)-one;
(R)-1-(1-phenylethyl)-6-(quinolin-5-yl)-1H-imidazo[4,5-b]pyridin-2(3H)-one;
1-(1-phenylethyl)-6-(quinolin-5-yl)-1H-imidazo[4,5-b]pyridin-2(3H)-one;
1-isopropyl-6-(quinolin-5-yl)-1H-imidazo[4,5-b]pyrazin-2(3H)-one;
1-(1-(4-chlorophenyl)ethyl)-6-(quinolin-5-yl)-1H-imidazo[4,5-b]pyrazin-2(3H)-one;
1-(1-(4-(methylsulfonyl)phenyl)ethyl)-6-(quinolin-5-yl)-1H-imidazo[4,5-b]pyrazin-2(3H)-one;
1-(1-(pyridin-4-yl)ethyl)-6-(quinolin-5-yl)-1H-imidazo[4,5-b]pyrazin-2(3H)-one;
5-methyl-1-((S)-1-phenylethyl)-6-(quinolin-5-yl)-1H-imidazo[4,5-b]pyrazin-2(3H)-one;
5-methyl-1-((R)-1-phenylethyl)-6-(quinolin-5-yl)-1H-imidazo[4,5-b]pyrazin-2(3H)-one;
1-(1-phenylethyl)-6-(quinolin-4-yl)-1H-imidazo[4,5-b]pyrazin-2(3H)-one;
6-(3-fluorophenyl)-1-(1-phenylethyl)-1H-imidazo[4,5-b]pyrazin-2(3H)-one;
6-(2-fluorophenyl)-1-(1-phenylethyl)-1H-imidazo[4,5-b]pyrazin-2(3H)-one;
1-(1-phenylethyl)-6-(quinolin-6-yl)-1H-imidazo[4,5-b]pyrazin-2(3H)-one;
1-(piperidin-4-ylmethyl)-6-(quinolin-5-yl)-1H-imidazo[4,5-b]pyrazin-2(3H)-one;
1-(1-(pyridin-2-yl)ethyl)-6-(quinolin-5-yl)-1H-imidazo[4,5-b]pyrazin-2(3H)-one;
1-(1-(pyridin-3-yl)ethyl)-6-(quinolin-5-yl)-1H-imidazo[4,5-b]pyrazin-2(3H)-one;
1-((1s,4s)-4-(hydroxymethyl)cyclohexyl)-6-(quinolin-5-yl)-1H-imidazo[4,5-b]pyrazin-2(3H)-one;
N-(4-(2-oxo-3-(1-phenylethyl)-2,3-dihydro-1H-imidazo[4,5-b]pyrazin-5-yl)phenyl)methanesulfonamide;
6-(3-(methylsulfonyl)phenyl)-1-(1-phenylethyl)-1H-imidazo[4,5-b]pyrazin-2(3H)-one;
6-(3-aminophenyl)-1-(1-phenylethyl)-1H-imidazo[4,5-b]pyrazin-2(3H)-one;
6-(3-(dimethylamino)phenyl)-1-(1-phenylethyl)-1H-imidazo[4,5-b]pyrazin-2(3H)-one;
1-phenyl-6-(quinolin-5-yl)-1H-imidazo[4,5-b]pyrazin-2(3H)-one;
1-(1-phenylethyl)-6-(4-(trifluoromethyl)phenyl)-1H-imidazo[4,5-b]pyrazin-2(3H)-one;
N-(3-(2-oxo-3-(1-phenylethyl)-2,3-dihydro-1H-imidazo[4,5-b]pyrazin-5-yl)phenyl)methanesulfonamide;
6-(4-(methylsulfonyl)phenyl)-1-(1-phenylethyl)-1H-imidazo[4,5-b]pyrazin-2(3H)-one;
3-(1-phenylethyl)-5-(quinolin-5-yl)oxazolo[5,4-b]pyrazin-2(3H)-one;
1-(cyclopentylmethyl)-6-(4-hydroxyphenyl)-1H-imidazo[4,5-b]pyrazin-2(3H)-one
6-(4-hydroxyphenyl)-1-isopropyl-1H-imidazo[4,5-b]pyrazin-2(3H)-one;
6-(4-hydroxyphenyl)-1-isobutyl-1H-imidazo[4,5-b]pyrazin-2(3H)-one;
6-(4-hydroxyphenyl)-1-((tetrahydro-2H-pyran-3-yl)methyl)-1H-imidazo[4,5-b]pyrazin-2(3H)-one;
1-(cyclohexylmethyl)-6-(4-hydroxyphenyl)-1H-imidazo[4,5-b]pyrazin-2(3H)-one;
5-(3-Hydroxyphenyl)-3-(2-methoxyphenyl)-1H-imidazo[4,5-b]pyridin-2(3H)-one;
4-(3-(3-Methoxybenzyl)-2-oxo-2,3-dihydrooxazolo[5,4-b]pyrazin-5-yl)-N-methyl benzamide;
1-Cyclopentyl-6-(4-hydroxyphenyl)-1H-imidazo[4,5-b]pyrazin-2(3H)-one;
1-Cyclohexyl-6-(4-hydroxyphenyl)-1H-imidazo[4,5-b]pyrazin-2(3H)-one;
4-(3-(Cyclohexylmethyl)-2-oxo-2,3-dihydro-1H-imidazo[4,5-b]pyrazin-5-yl)benzamide;
Methyl 4-(3-(cyclohexylmethyl)-2-oxo-2,3-dihydro-1H-imidazo[4,5-b]pyrazin-5-yl)benzoate;
1-Cyclohexylmethyl-6-(pyridin-4-yl)-1H-imidazo[4,5-b]pyrazin-2(3H)-one;
4-(3-(Cyclohexylmethyl)-2-oxo-2,3-dihydro-1H-imidazo[4,5-b]pyrazin-5-yl)-N-methylbenzamide;
1-(Cyclohexylmethyl)-6-(4-(hydroxymethyl)phenyl)-1H-imidazo[4,5-b]pyrazin-2(3H)-one;
1-(Cyclohexylmethyl)-6-(pyridin-3-yl)-1H-imidazo[4,5-b]pyrazin-2(3H)-one;
3-(Cyclohexylmethyl)-2-oxo-2,3-dihydro-1H-imidazo[4,5-b]pyrazin-5-yl)benzonitrile;
1-(Cyclohexylmethyl)-6-(1H-indol-5-yl)-1H-imidazo[4,5-b]pyrazin-2(3H)-one;
4-(3-(Cyclohexylmethyl)-2-oxo-2,3-dihydro-1H-imidazo[4,5-b]pyrazin-5-yl)-N-isopropylbenzamide;
1-(2-Hydroxyethyl)-6-(4-hydroxyphenyl)-1H-imidazo[4,5-b]pyrazin-2(3H)-one;
1-(Cyclohexylmethyl)-6-(1H-indol-6-yl)-1H-imidazo[4,5-b]pyrazin-2(3H)-one;
3-(3-(Cyclohexylmethyl)-2-oxo-2,3-dihydro-1H-imidazo[4,5-b]pyrazin-5-yl)benzamide;
6-(4-(Aminomethyl)phenyl)-1-(cyclohexylmethyl)-1H-imidazo[4,5-b]pyrazin-2(3H)-one;
6-(4-Hydroxyphenyl)-1-((1-methylpiperidin-4-yl)methyl)-1H-imidazo[4,5-b]pyrazin-2(3H)-one;;
4-(3-(Cyclohexylmethyl)-2-oxo-2,3-dihydro-1H-imidazo[4,5-b]pyrazin-5-yl)benzonitrile;
1-((1s,4s)-4-Hydroxycyclohexyl)-6-(4-hydroxyphenyl)-1H-imidazo[4,5-b]pyrazin-2(3H)-one;
1-(Cyclohexylmethyl)-6-(pyridin-2-yl)-1H-imidazo[4,5-b]pyrazin-2(3H)-one;
4-(3-(Cyclohexylmethyl)-2-oxo-2,3-dihydro-1H-imidazo[4,5-b]pyrazin-5-yl)-N-ethylbenzamide;
1-(Cyclohexylmethyl)-6-(4-(2-hydroxypropan-2-yl)phenyl)-1H-imidazo[4,5-b]pyrazin-2(3H)-one;
1-(Cyclohexylmethyl)-6-(4-hydroxy-2-methylphenyl)-1H-imidazo[4,5-b]pyrazin-2(3H)-one;
4-(3-(Cyclohexylmethyl)-2-oxo-2,3-dihydro-1H-imidazo[4,5-b]pyrazin-5-yl)benzoic acid;
6-(4-Hydroxyphenyl)-1-(2-methoxyethyl)-1H-imidazo[4,5-b]pyrazin-2(3H)-one;
6-(4-Hydroxyphenyl)-1-(3-methoxypropyl)-1H-imidazo[4,5-b]pyrazin-2(3H)-one;
6-(4-Hydroxyphenyl)-4-(3-methoxybenzyl)-3,4-dihydropyrazino[2,3-b]pyrazin-2(1H)-one;
6-(4-Hydroxyphenyl)-1-(2-(tetrahydro-2H-pyran-4-yl)ethyl)-1H-imidazo[4,5-b]pyrazin-2(3H)-one;
6-(4-Hydroxyphenyl)-1-phenethyl-1H-imidazo[4,5-b]pyrazin-2(3H)-one;
1-((1r,4r)-4-Hydroxycyclohexyl)-6-(4-hydroxyphenyl)-1H-imidazo[4,5-b]pyrazin-2(3H)-one;
6-(4-(1H-1,2,4-Triazol-3-yl)phenyl)-1-(cyclohexylmethyl)-1H-imidazo[4,5-b]pyrazin-2(3H)-one;
1-(Cyclohexylmethyl)-6-phenyl-1H-imidazo[4,5-b]pyrazin-2(3H)-one;
1-(Cyclohexylmethyl)-6-(1H-pyrazol-5-yl)-1H-imidazo[4,5-b]pyrazin-2(3H)-one;
1-(Cyclohexylmethyl)-6-(1H-pyrazol-4-yl)-1H-imidazo[4,5-b]pyrazin-2(3H)-one;
1-(Cyclohexylmethyl)-6-(1-oxoisoindolin-5-yl)-1H-imidazo[4,5-b]pyrazin-2(3H)-one;
6-(3-(1H-Tetrazol-5-yl)phenyl)-1-(cyclohexylmethyl)-1H-imidazo[4,5-b]pyrazin-2(3H)-one;
1-(Cyclohexylmethyl)-6-(2-oxoindolin-5-yl)-1H-imidazo[4,5-b]pyrazin-2(3H)-one;

TABLE A-continued 1-(Cyclohexylmethyl)-6-(1H-indazol-5-yl)-1H-imidazo[4,5-b]pyrazin-2(3H)-one;
1-(Cyclohexylmethyl)-6-(6-methoxypyridin-3-yl)-1H-imidazo[4,5-b]pyrazin-2(3H)-one;
6-(4-Hydroxyphenyl)-1-(tetrahydro-2H-pyran-4-yl)-1H-imidazo[4,5-b]pyrazin-2(3H)-one;
6-(4-Hydroxyphenyl)-1-(piperidin-4-ylmethyl)-1H-imidazo[4,5-b]pyrazin-2(3H)-one;
1-(((1r,4r)-4-Aminocyclohexyl)methyl)-6-(4-hydroxyphenyl)-1H-imidazo[4,5-b]pyrazin-2(3H)-one;
1-(Cyclohexylmethyl)-6-(6-hydroxypyridin-3-yl)-1H-imidazo[4,5-b]pyrazin-2(3H)-one;
1-(Cyclohexylmethyl)-6-(2-methoxypyridin-4-yl)-1H-imidazo[4,5-b]pyrazin-2(3H)-one;
4-(3-((1r,4r)-4-Hydroxycyclohexyl)-2-oxo-2,3-dihydro-1H-imidazo[4,5-b]pyrazin-5-yl)benzamide;
2-(4-(3-(Cyclohexylmethyl)-2-oxo-2,3-dihydro-1H-imidazo[4,5-b]pyrazin-5-yl)phenyl) acetic acid;
2-(4-(3-(Cyclohexylmethyl)-2-oxo-2,3-dihydro-1H-imidazo[4,5-b]pyrazin-5-yl)phenyl) acetamide;
1-(Cyclohexylmethyl)-6-(2-oxoindolin-6-yl)-1H-imidazo[4,5-b]pyrazin-2(3H)-one;
4-(3-(Cyclohexylmethyl)-2-oxo-2,3-dihydro-1H-imidazo[4,5-b]pyrazin-5-yl)-3-methyl benzoic acid;
N-Methyl-4-(2-oxo-3-((tetrahydro-2H-pyran-4-yl)methyl)-2,3-dihydro-1H-imidazo[4,5-b]pyrazin-5-yl)benzamide;
4-(2-oxo-3-((Tetrahydro-2H-pyran-4-yl)methyl)-2,3-dihydro-1H-imidazo[4,5-b]pyrazin-5-yl)benzamide;
7-(4-Hydroxyphenyl)-1-(3-methoxybenzyl)-3,4-dihydropyrazino[2,3-b]pyrazin-2(1H)-one;
6-(4-(2-Hydroxypropan-2-yl)phenyl)-1-((tetrahydro-2H-pyran-4-yl)methyl)-1H-imidazo[4,5-b]pyrazin-2(3H)-one;
6-(1H-Indol-5-yl)-1-((tetrahydro-2H-pyran-4-yl)methyl)-1H-imidazo[4,5-b]pyrazin-2(3H)-one;
6-(4-(4H-1,2,4-Triazol-3-yl)phenyl)-1-((tetrahydro-2H-pyran-4-yl)methyl)-1H-imidazo[4,5-b]pyrazin-2(3H)-one;
6-(1H-Benzo[d]imidazol-5-yl)-1-(cyclohexylmethyl)-1H-imidazo[4,5-b]pyrazin-2(3H)-one;
4-(2-oxo-3-(2-(Tetrahydro-2H-pyran-4-yl)ethyl)-2,3-dihydro-1H-imidazo[4,5-b]pyrazin-5-yl)benzamide;
6-(3-(2H-1,2,3-Triazol-4-yl)phenyl)-1-(cyclohexylmethyl)-1H-imidazo[4,5-b]pyrazin-2(3H)-one;
6-(4-(1H-Imidazol-1-yl)phenyl)-1-(cyclohexylmethyl)-1H-imidazo[4,5-b]pyrazin-2(3H)-one;
6-(4-(1H-1,2,4-Triazol-3-yl)phenyl)-1-((1r,4r)-4-hydroxycyclohexyl)-1H-imidazo[4,5-b]pyrazin-2(3H)-one;
6-(4-(2H-tetrazol-5-yl)phenyl)-1-(cyclohexylmethyl)-1H-imidazo[4,5-b]pyrazin-2(3H)-one;
1-(Cyclohexylmethyl)-6-(2-hydroxypyridin-4-yl)-1H-imidazo[4,5-b]pyrazin-2(3H)-one;
6-(4-(1H-1,2,4-Triazol-3-yl)phenyl)-1-(2-(tetrahydro-2H-pyran-4-yl)ethyl)-1H-imidazo[4,5-b]pyrazin-2(3H)-one;
6-(4-(1H-Imidazol-2-yl)phenyl)-1-(cyclohexylmethyl)-1H-imidazo[4,5-b]pyrazin-2(3H)-one;
6-(4-(1H-1,2,3-Triazol-1-yl)phenyl)-1-(cyclohexylmethyl)-1H-imidazo[4,5-b]pyrazin-2(3H)-one;
6-(4-(2-Hydroxypropan-2-yl)phenyl)-1-(2-(tetrahydro-2H-pyran-4-yl)ethyl)-1H-imidazo[4,5-b]pyrazin-2(3H)-one;
1-(Cyclohexylmethyl)-6-(4-(5-methyl-1H-1,2,4-triazol-3-yl)phenyl)-1H-imidazo[4,5-b]pyrazin-2(3H)-one;
6-(4-(1H-Pyrazol-3-yl)phenyl)-1-(cyclohexylmethyl)-1H-imidazo[4,5-b]pyrazin-2(3H)-one;
6-(4-(1H-Pyrazol-4-yl)phenyl)-1-(cyclohexylmethyl)-1H-imidazo[4,5-b]pyrazin-2(3H)-one;
6-(4-(5-(Aminomethyl)-1H-1,2,4-triazol-3-yl)phenyl)-1-(cyclohexylmethyl)-1H-imidazo[4,5-b]pyrazin-2(3H)-one hydrochloride;
1-(Cyclohexylmethyl)-6-(4-(5-(trifluoromethyl)-1H-1,2,4-triazol-3-yl)phenyl)-1H-imidazo[4,5-b]pyrazin-2(3H)-one;
6-(4-Hydroxyphenyl)-1-((1r,4r)-4-methoxycyclohexyl)-1H-imidazo[4,5-b]pyrazin-2(3H)-one;
6-(4-Hydroxyphenyl)-1-((tetrahydrofuran-2-yl)methyl)-1H-imidazo[4,5-b]pyrazin-2(3H)-one;
6-(3-(1H-1,2,4-Triazol-3-yl)phenyl)-1-(cyclohexylmethyl)-1H-imidazo[4,5-b]pyrazin-2(3H)-one;
1-((1r,4r)-4-(Hydroxymethyl)cyclohexyl)-6-(4-hydroxyphenyl)-1H-imidazo[4,5-b]pyrazin-2(3H)-one;
6-(4-Hydroxyphenyl)-1-((1s,4s)-4-methoxycyclohexyl)-1H-imidazo[4,5-b]pyrazin-2(3H)-one;
6-(4-Hydroxyphenyl)-1-((1r,4r)-4-(methoxymethyl)cyclohexyl)-1H-imidazo[4,5-b]pyrazin-2(3H)-one;
6-(1-Methyl-1H-pyrazol-4-yl)-1-((tetrahydro-2H-pyran-4-yl)methyl)-1H-imidazo[4,5-b]pyrazin-2(3H)-one;
1-(((1r,4r)-4-Hydroxycyclohexyl)methyl)-6-(4-hydroxyphenyl)-1H-imidazo[4,5-b]pyrazin-2(3H)-one;
6-(4-Hydroxyphenyl)-1-((tetrahydrofuran-3-yl)methyl)-1H-imidazo[4,5-b]pyrazin-2(3H)-one;
1-(((1s,4s)-4-Hydroxycyclohexyl)methyl)-6-(4-hydroxyphenyl)-1H-imidazo[4,5-b]pyrazin-2(3H)-one;
6-(1H-Benzo[d]imidazol-5-yl)-1-((tetrahydro-2H-pyran-4-yl)methyl)-1H-imidazo[4,5-b]pyrazin-2(3H)-one hydrochloride;
6-(4-(5-(Morpholinomethyl)-1H-1,2,4-triazol-3-yl)phenyl)-1-((tetrahydro-2H-pyran-4-yl)methyl)-1H-imidazo[4,5-b]pyrazin-2(3H)-one;
6-(4-Hydroxyphenyl)-1-(3-(2-oxopyrrolidin-1-yl)propyl)-1H-imidazo[4,5-b]pyrazin-2(3H)-one;
6-(4-Hydroxyphenyl)-1-(2-morpholinoethyl)-1H-imidazo[4,5-b]pyrazin-2(3H)-one hydrochloride;
1-(Cyclohexylmethyl)-6-(4-(oxazol-5-yl)phenyl)-1H-imidazo[4,5-b]pyrazin-2(3H)-one;
6-(2-Methyl-1H-benzo[d]imidazol-5-yl)-1-((tetrahydro-2H-pyran-4-yl)methyl)-1H-imidazo[4,5-b]pyrazin-2(3H)-one hydrocholoride;
6-(4-(5-(Methoxymethyl)-1H-1,2,4-triazol-3-yl)phenyl)-1-((tetrahydro-2H-pyran-4-yl)methyl)-1H-imidazo[4,5-b]pyrazin-2(3H)-one;

TABLE A-continued 1-((1s,4s)-4-(Hydroxymethyl)cyclohexyl)-6-(4-hydroxyphenyl)-1H-imidazo[4,5-b]pyrazin-2(3H)-one;
6-(3-Methyl-1H-pyrazol-4-yl)-1-((tetrahydro-2H-pyran-4-yl)methyl)-1H-imidazo[4,5-b]pyrazin-2(3H)-one;
6-(1H-Pyrazol-4-yl)-1-((tetrahydro-2H-pyran-4-yl)methyl)-1H-imidazo[4,5-b]pyrazin-2(3H)-one;
6-(2-Amino-1H-benzo[d]imidazol-5-yl)-1-((tetrahydro-2H-pyran-4-yl)methyl)-1H-imidazo[4,5-b]pyrazin-2(3H)-one di hydrochloride;
6-(4-(5-(2-Hydroxypropan-2-yl)-1H-1,2,4-triazol-3-yl)phenyl)-1-((tetrahydro-2H-pyran-4-yl)methyl)-1H-imidazo[4,5-b]pyrazin-2(3H)-one;
6-(4-(5-Isopropyl-1H-1,2,4-triazol-3-yl)phenyl)-1-((tetrahydro-2H-pyran-4-yl)methyl)-1H-imidazo[4,5-b]pyrazin-2(3H)-one;
4-(2-Methoxy-1-(2-morpholinoethyl)-1H-imidazo[4,5-b]pyrazin-6-yl)benzamide hydrochloride;
4-(1-((1s,4s)-4-Hydroxycyclohexyl)-2-methoxy-1H-imidazo[4,5-b]pyrazin-6-yl)benzamide;
6-(4-Hydroxyphenyl)-1-((1s,4s)-4-(methoxymethyl)cyclohexyl)-1H-imidazo[4,5-b]pyrazin-2(3H)-one;
6-(3H-imidazo[4,5-b]pyridin-6-yl)-1-((tetrahydro-2H-pyran-4-yl)methyl)-1H-imidazo[4,5-b]pyrazin-2(3H)-one;
1-(2-(2,2-Dimethyltetrahydro-2H-pyran-4-yl)ethyl)-6-(4-hydroxyphenyl)-1H-imidazo[4,5-b]pyrazin-2(3H)-one;
6-(4-(1H-Pyrazol-1-yl)phenyl)-1-((tetrahydro-2H-pyran-4-yl)methyl)-1H-imidazo[4,5-b]pyrazin-2(3H)-one;
6-(4-(4H-1,2,4-Triazol-3-yl)phenyl)-1-(2-morpholinoethyl)-1H-imidazo[4,5-b]pyrazin-2(3H)-one;
6-(4-(1H-Benzo[d]imidazol-2-yl)phenyl)-1-((tetrahydro-2H-pyran-4-yl)methyl)-1H-imidazo[4,5-b]pyrazin-2(3H)-one;
6-(4-(1H-Imidazol-2-yl)phenyl)-1-((tetrahydro-2H-pyran-4-yl)methyl)-1H-imidazo[4,5-b]pyrazin-2(3H)-one hydrochloride;
6-(4-(5-(Hydroxymethyl)-1H-1,2,4-triazol-3-yl)phenyl)-1-((tetrahydro-2H-pyran-4-yl)methyl)-1H-imidazo[4,5-b]pyrazin-2(3H)-one;
6-(4-(1H-Imidazol-5-yl)phenyl)-1-((tetrahydro-2H-pyran-4-yl)methyl)-1H-imidazo[4,5-b]pyrazin-2(3H)-one hydrochloride;
6-(4-Hydroxyphenyl)-1-((5-oxopyrrolidin-2-yl)methyl)-1H-imidazo[4,5-b]pyrazin-2(3H)-one;
6-(4-(4,5-Dimethyl-1H-imidazol-2-yl)phenyl)-1-((tetrahydro-2H-pyran-4-yl)methyl)-1H-imidazo[4,5-b]pyrazin-2(3H)-one;
6-(4-(1H-1,2,4-Triazol-5-yl)phenyl)-1-(((1s,4s)-4-methoxycyclohexyl)methyl)-1H-imidazo[4,5-b]pyrazin-2(3H)-one;
6-(4-(1H-1,2,4-Triazol-5-yl)phenyl)-1-(((1r,4r)-4-methoxycyclohexyl)methyl)-1H-imidazo[4,5-b]pyrazin-2(3H)-one;
6-(6-(1H-1,2,4-Triazol-3-yl)pyridin-3-yl)-1-((tetrahydro-2H-pyran-4-yl)methyl)-1H-imidazo[4,5-b]pyrazin-2(3H)-one;
6-(4-(1H-1,2,4-Triazol-3-yl)phenyl)-1-(2-(2-oxopyrrolidin-1-yl)ethyl)-1H-imidazo[4,5-b]pyrazin-2(3H)-one;
6-(4-(5-((dimethylamino)methyl)-1H-1,2,4-triazol-3-yl)phenyl)-1-((tetrahydro-2H-pyran-4-yl)methyl)-1H-imidazo[4,5-b]pyrazin-2(3H)-one;
6-(4-Hydroxyphenyl)-1-(pyrrolidin-2-ylmethyl)-1H-imidazo[4,5-b]pyrazin-2(3H)-one hydrochloride;
6-(2-Aminobenzimidazol-5-yl)-1-(cyclohexylmethyl)-4-imidazolino[4,5-b]pyrazin-2-one di hydrochloride;
6-(2-(Dimethylamino)-1H-benzo[d]imidazol-5-yl)-1-((tetrahydro-2H-pyran-4-yl) methyl)-1H-imidazo[4,5-b]pyrazin-2(3H)-one;
6-(4-Hydroxyphenyl)-1-(piperidin-3-ylmethyl)-1H-imidazo[4,5-b]pyrazin-2(3H)-one;
6-(4-(4H-1,2,4-triazol-3-yl)phenyl)-1-(2-(piperidin-1-yl)ethyl)-1H-imidazo[4,5-b]pyrazin-2(3H)-one hydrochloride;
1-(Cyclohexylmethyl)-6-(2-(methylamino)pyrimidin-5-yl)-1H-imidazo[4,5-b]pyrazin-2(3H)-one;
6-(3-methyl-4-(1H-1,2,4-triazol-3-yl)phenyl)-1-((tetrahydro-2H-pyran-4-yl)methyl)-1H-imidazo[4,5-b]pyrazin-2(3H)-one;
1-(Cyclohexylmethyl)-6-(2-(2-methoxyethylamino)pyrimidin-5-yl)-1H-imidazo[4,5-b]pyrazin-2(3H)-one;
6-(4-(5-((methylamino)methyl)-1H-1,2,4-triazol-3-yl)phenyl)-1-((tetrahydro-2H-pyran-4-yl)methyl)-1H-imidazo[4,5-b]pyrazin-2(3H)-one;
6-(4-(5-Oxopyrrolidin-2-yl)phenyl)-1-(2-(tetrahydro-2H-pyran-4-yl)ethyl)-1H-imidazo[4,5-b]pyrazin-2(3H)-one;
6-(4-(5-methyl-1H-1,2,4-triazol-3-yl)phenyl)-1-(2-(tetrahydro-2H-pyran-4-yl)ethyl)-1H-imidazo[4,5-b]pyrazin-2(3H)-one;
6-(4-(1H-imidazol-2-yl)phenyl)-1-(2-(tetrahydro-2H-pyran-4-yl)ethyl)-1H-imidazo[4,5-b]pyrazin-2(3H)-one;
6-(4-(4H-1,2,4-triazol-3-yl)phenyl)-1-(2-methyl-2-morpholinopropyl)-1H-imidazo[4,5-b]pyrazin-2(3H)-one;
6-(4-(4H-1,2,4-Triazol-3-yl)phenyl)-1-(1-morpholinopropan-2-yl)-1H-imidazo[4,5-b]pyrazin-2(3H)-one;
6-(4-(Pyrrolidin-2-yl)phenyl)-1-(2-(tetrahydro-2H-pyran-4-yl)ethyl)-1H-imidazo[4,5-b]pyrazin-2(3H)-one;
6-(4-(5-(aminomethyl)-1H-1,2,4-triazol-3-yl)phenyl)-1-(2-(tetrahydro-2H-pyran-4-yl)ethyl)-1H-imidazo[4,5-b]pyrazin-2(3H)-one;
6-(5-(Hydroxymethyl)thiophen-2-yl)-1-((tetrahydro-2H-pyran-4-yl)methyl)-1H-imidazo[4,5-b]pyrazin-2(3H)-one;
(1r,4r)-4-(6-(4-Hydroxyphenyl)-2-oxo-2,3-dihydro-1H-imidazo[4,5-b]pyrazin-1-yl)cyclohexanecarboxamide;

TABLE A-continued (1s,4s)-4-(6-(4-Hydroxyphenyl)-2-oxo-2,3-dihydro-1H-imidazo[4,5-b]pyrazin-1-yl)cyclohexanecarboxamide;
6-(4-(5-methyl-1H-1,2,4-triazol-3-yl)phenyl)-1-(2-morpholinoethyl)-1H-imidazo[4,5-b]pyrazin-2(3H)-one;
6-(4-(5-Oxopyrrolidin-3-yl)phenyl)-1-(2-(tetrahydro-2H-pyran-4-yl)ethyl)-1H-imidazo[4,5-b]pyrazin-2(3H)-one;
6-(4-(Pyrrolidin-3-yl)phenyl)-1-(2-(tetrahydro-2H-pyran-4-yl)ethyl)-1H-imidazo[4,5-b]pyrazin-2(3H)-one;
6-(1H-benzo[d]imidazol-5-yl)-1-(2-(tetrahydro-2H-pyran-4-yl)ethyl)-1H-imidazo[4,5-b]pyrazin-2(3H)-one;
6-(3-(Hydroxymethyl)thiophen-2-y 1)-1-((tetrahydro-2H-pyran-4-yl)methyl)-1H-imidazo[4,5-b]pyrazin-2(3H)-one;
6-(5-(2-Hydroxyethyl)thiophen-2-yl)-1-((tetrahydro-2H-pyran-4-yl)methyl)-1H-imidazo[4,5-b]pyrazin-2(3H)-one;
1-(Cyclohexylmethyl)-6-(pyrimidin-5-yl)-1H-imidazo[4,5-b]pyrazin-2(3H)-one;
6-(6-Fluoropyridin-3-yl)-1-((tetrahydro-2H-pyran-4-yl)methyl)-1H-imidazo[4,5-b]pyrazin-2(3H)-one;
6-(6-Aminopyridin-3-yl)-1-((tetrahydro-2H-pyran-4-yl)methyl)-1H-imidazo[4,5-b]pyrazin-2(3H)-one;
6-(4-(5-methyl-1H-imidazol-2-yl)phenyl)-1-((tetrahydro-2H-pyran-4-yl)methyl)-1H-imidazo[4,5-b]pyrazin-2(3H)-one;
6-(4-(5-Methyl-1H-1,2,4-triazol-3-yl)phenyl)-1-(2-(2-oxopyrrolidin-1-yl)ethyl)-1H-imidazo[4,5-b]pyrazin-2(3H)-one;
6-(6-(Methylamino)pyridin-3-yl)-1-((tetrahydro-2H-pyran-4-yl)methyl)-1H-imidazo[4,5-b]pyrazin-2(3H)-one;
6-(2-aminopyrimidin-5-yl)-1-(cyclohexylmethyl)-1H-imidazo[4,5-b]pyrazin-2(3H)-one;
6-(4-(2-hydroxypropan-2-yl)phenyl)-1-(((1r,4r)-4-methoxycyclohexyl)methyl)-1H-imidazo[4,5-b]pyrazin-2(3H)-one;
6-(4-hydroxyphenyl)-1-((1-methylpiperidin-3-yl)methyl)-1H-imidazo[4,5-b]pyrazin-2(3H)-one;
6-(2-methyl-4-(1H-1,2,4-triazol-3-yl)phenyl)-1-(2-(tetrahydro-2H-pyran-4-yl)ethyl)-1H-imidazo[4,5-b]pyrazin-2(3H)-one;
1-(cyclohexylmethyl)-6-(6-(2-hydroxypropan-2-yl)pyridin-3-yl)-1H-imidazo[4,5-b]pyrazin-2(3H)-one;
6-(4-(hydroxymethyl)thiophen-2-yl)-1-((tetrahydro-2H-pyran-4-yl)methyl)-1H-imidazo[4,5-b]pyrazin-2(3H)-one;
6-(1H-benzo[d]imidazol-6-yl)-1-(((1r,4r)-4-methoxycyclohexyl)methyl)-1H-imidazo[4,5-b]pyrazin-2(3H)-one;
6-(4-(4,5-dimethyl-1H-imidazol-2-yl)phenyl)-1-(2-morpholinoethyl)-1H-imidazo[4,5-b]pyrazin-2(3H)-one;
6-(6-(2-hydroxypropan-2-yl)pyridin-3-yl)-1-((tetrahydro-2H-pyran-4-yl)methyl)-1H-imidazo[4,5-b]pyrazin-2(3H)-one;
6-(6-(2-hydroxypropan-2-yl)pyridin-3-yl)-1-(2-(tetrahydro-2H-pyran-4-yl)ethyl)-1H-imidazo[4,5-b]pyrazin-2(3H)-one;
6-(4-(4H-1,2,4-triazol-3-yl)phenyl)-1-(2-morpholino-2-oxoethyl)-1H-imidazo[4,5-b]pyrazin-2(3H)-one;
6-(4-(4H-1,2,4-triazol-3-yl)phenyl)-3-(cyclohexylmethyl)-3,4-dihydropyrazino[2,3-b]pyrazin-2(1H)-one;
6-(4-(1H-1,2,4-triazol-3-yl)phenyl)-1-(2-(tetrahydro-2H-pyran-4-yl)ethyl)-1H-imidazo[4,5-b]pyridin-2(3H)-one;
(R)-6-(4-(1H-1,2,4-triazol-3-yl)phenyl)-1-(1-phenylethyl)-1H-imidazo[4,5-b]pyrazin-2(3H)-one;
(S)-6-(4-(1H-1,2,4-triazol-3-yl)phenyl)-1-(1-phenylethyl)-1H-imidazo[4,5-b]pyrazin-2(3H)-one;
(1r,4r)-4-(6-(4-(2-hydroxypropan-2-yl)phenyl)-2-oxo-2,3-dihydro-1H-imidazo[4,5-b]pyrazin-1-yl)cyclohexanecarboxamide;
6-(3-Methyl-4-(1H-1,2,4-Triazol-3-yl)phenyl)-1-((tetrahydro-2H-pyran-4-yl)methyl)-1H-imidazo[4,5-B]pyrazin-2(3H)-one;
6-(4-(1H-imidazol-2-yl)phenyl)-1-(2-(tetrahydro-2H-pyran-4-yl)ethyl)-1H-imidazo[4,5-b]pyrazin-2(3H)-one;
6-(4-(5-(Aminomethyl)-1H-1,2,4-triazol-3-yl)phenyl)-1-(2-(tetrahydro-2H-pyran-4-yl)ethyl)-1H-imidazo[4,5-b]pyrazin-2(3H)-one;
6-(1H-benzo[d]imidazol-5-yl)-1-(2-(tetrahydro-2H-pyran-4-yl)ethyl)-1H-imidazo[4,5-b]pyrazin-2(3H)-one;
6-(2-Aminopyrimidin-5-yl)-1-(cyclohexylmethyl)-1H-imidazo[4,5-b]pyrazin-2(3H)-one;
6-(4-Hydroxyphenyl)-1-((1-methylpiperidin-2-yl)methyl)-1H-imidazo[4,5-b]pyrazin-2(3H)-one hydrochloride;
6-(3-Methyl-4-(1H-1,2,4-Triazol-3-yl)phenyl)-1-((tetrahydro-2H-pyran-4-yl)methyl)-1H-imidazo[4,5-B]pyrazin-2(3H)-one;
1-(Cyclohexylmethyl)-6-(6-(2-hydroxypropan-2-yl)pyridin-3-yl)-1H-imidazo[4,5-b]pyrazin-2(3H)-one;
6-(6-(2-Hydroxypropan-2-yl)pyridin-3-yl)-1-((tetrahydro-2H-pyran-4-yl)methyl)-1H-imidazo[4,5-b]pyrazin-2(3H)-one;
6-(6-(2-Hydroxypropan-2-yl)pyridin-3-yl)-1-(2-(tetrahydro-2H-pyran-4-yl)ethyl)-1H-imidazo[4,5-b]pyrazin-2(3H)-one;
6-(4-(4H-1,2,4-Triazol-3-yl)phenyl)-1-(2-morpholino-2-oxoethyl)-1H-imidazo[4,5-b]pyrazin-2(3H)-one;
(R)-6-(4-(4H-1,2,4-Triazol-3-yl)phenyl)-3-(cyclohexylmethyl)-3,4-dihydropyrazino[2,3-b]pyrazin-2(1H)-one;
(R)-6-(4-(1H-1,2,4-Triazol-3-yl)phenyl)-1-(1-phenylethyl)-1H-imidazo[4,5-B]pyrazin-2(3H)-one;
(S)-6-(4-(4H-1,2,4-Triazol-3-yl)phenyl)-1-(1-phenylethyl)-1H-imidazo[4,5-b]pyrazin-2(3H)-one;

TABLE A-continued (1r,4r)-4-(6-(4-(2-Hydroxypropan-2-yl)phenyl)-2-oxo-2,3-dihydro-1H-imidazo[4,5-b]pyrazin-1-yl)cyclohexanecarboxamide; and
6-(4-(5-Methyl-1H-1,2,4-triazol-3-yl)phenyl)-1-(2-(tetrahydro-2H-pyran-4-yl)ethyl)-1H-imidazo[4,5-b]pyrazin-2(3H)-one,
and pharmaceutically acceptable salts, clathrates, solvates, stereoisomers, tautomers, and prodrugs thereof.

In one embodiment, the TOR kinase inhibitors include compounds having the following formula (II):

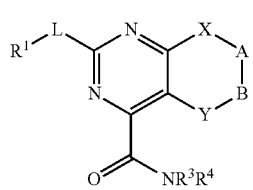

(II)

and pharmaceutically acceptable salts, clathrates, solvates, stereoisomers, tautomers, and prodrugs thereof, wherein:

$R^1$ is substituted or unsubstituted $C_{1-8}$alkyl, substituted or unsubstituted aryl, substituted or unsubstituted heteroaryl, substituted or unsubstituted cycloalkyl, or substituted or unsubstituted heterocyclylalkyl;

—X-A-B—Y— taken together form —N($R^2$)CH$_2$C(O)NH—, —N($R^2$)C(O)CH$_2$NH—, —N($R^2$)C(O)NH—, —N($R^2$)C=N—, or —C($R^2$)=CHNH—;

L is a direct bond, NH or O;

$R^2$ is substituted or unsubstituted $C_{1-8}$alkyl, substituted or unsubstituted aryl, substituted or unsubstituted heteroaryl, substituted or unsubstituted cycloalkyl, or substituted or unsubstituted heterocyclylalkyl; and $R^3$ and $R^4$ are independently H or $C_{1-8}$alkyl.

In one embodiment, the TOR kinase inhibitors of formula (II) are those wherein —X-A-B—Y— taken together form —N($R^2$)CH$_2$C(O)NH—.

In another embodiment, the TOR kinase inhibitors of formula (II) are those wherein —X-A-B—Y— taken together form —N($R^2$)C(O)CH$_2$NH—.

In another embodiment, the TOR kinase inhibitors of formula (II) are those wherein —X-A-B—Y— taken together form —N($R^2$)C(O)NH—.

In another embodiment, the TOR kinase inhibitors of formula (II) are those wherein —X-A-B—Y— taken together form —N($R^2$)C=N—.

In another embodiment, the TOR kinase inhibitors of formula (II) are those wherein —X-A-B—Y— taken together form —C($R^2$)=CHNH—.

In another embodiment, the TOR kinase inhibitors of formula (II) are those wherein L is a direct bond.

In another embodiment, the TOR kinase inhibitors of formula (II) are those wherein $R^1$ is substituted aryl, such as substituted phenyl.

In another embodiment, the TOR kinase inhibitors of formula (II) are those wherein $R^1$ is substituted or unsubstituted heteroaryl, such as substituted or unsubstituted pyridine, substituted or unsubstituted indole or substituted or unsubstituted quinoline.

In another embodiment, the TOR kinase inhibitors of formula (II) are those wherein $R^1$ is substituted or unsubstituted cycloalkyl, such as substituted or unsubstituted cyclopentyl.

In another embodiment, the TOR kinase inhibitors of formula (II) are those wherein —X-A-B—Y— taken together form —N($R^2$)C(O)NH— and $R^1$ is substituted aryl, such as phenyl.

In another embodiment, the TOR kinase inhibitors of formula (II) are those wherein —X-A-B—Y— taken together form —N($R^2$)C(O)NH— and $R^1$ is substituted or unsubstituted heteroaryl, such as substituted or unsubstituted pyridine, substituted or unsubstituted indole or substituted or unsubstituted quinoline.

In another embodiment, the TOR kinase inhibitors of formula (II) are those wherein —X-A-B—Y— taken together form —N($R^2$)C(O)NH— and $R^1$ is substituted or unsubstituted cycloalkyl, such as substituted or unsubstituted cyclopentyl.

In another embodiment, the TOR kinase inhibitors of formula (II) are those wherein $R^2$ is substituted $C_{1-8}$alkyl, such as —CH$_2$C$_6$H$_5$.

In another embodiment, the TOR kinase inhibitors of formula (II) are those wherein $R^2$ is unsubstituted $C_{1-8}$alkyl, such as unsubstituted methyl.

In another embodiment, the TOR kinase inhibitors of formula (II) are those wherein $R^2$ is substituted or unsubstituted aryl, such as substituted or unsubstituted phenyl.

In another embodiment, the TOR kinase inhibitors of formula (II) are those wherein $R^2$ is substituted aryl, such as halo, haloalkyl or alkoxy substituted phenyl.

In another embodiment, the TOR kinase inhibitors of formula (II) are those wherein $R^2$ is substituted or unsubstituted cycloalkyl, such as substituted or unsubstituted cyclohexyl or substituted or unsubstituted cycloheptyl.

In another embodiment, the TOR kinase inhibitors of formula (II) are those wherein $R^2$ is substituted heterocyclylalkyl, such as substituted piperidine.

In another embodiment, the TOR kinase inhibitors of formula (II) are those wherein $R^3$ and $R^4$ are H.

In another embodiment, the TOR kinase inhibitors of formula (II) are those wherein —X-A-B—Y— taken together form —N($R^2$)C(O)NH— and $R^2$ is unsubstituted aryl, such as unsubstituted phenyl.

In another embodiment, the TOR kinase inhibitors of formula (II) are those wherein —X-A-B—Y— taken together form —N($R^2$)C(O)NH—, $R^1$ is substituted or unsubstituted heteroaryl, such as substituted or unsubstituted pyridine, and $R^2$ is substituted or unsubstituted aryl, such as substituted or unsubstituted phenyl.

In another embodiment, the TOR kinase inhibitors of formula (II) are those wherein —X-A-B—Y— taken together form —N($R^2$)C(O)NH—, $R^1$ is substituted or unsubstituted heteroaryl, such as substituted or unsubstituted pyridine, $R^2$ is substituted or unsubstituted aryl, such as substituted or unsubstituted phenyl, and $R^3$ and $R^4$ are H.

In another embodiment, the TOR kinase inhibitors of formula (II) are those wherein —X-A-B—Y— taken together form —N($R^2$)C(O)NH—, L is a direct bond, $R^1$ is substituted or unsubstituted heteroaryl, such as substituted or unsubstituted pyridine, R² is substituted or unsubstituted aryl, such as substituted or unsubstituted phenyl, and R³ and R⁴ are H.

In another embodiment, the TOR kinase inhibitors of formula (II) are those wherein —X-A-B—Y— taken together form —N(R²)C(O)NH—, R¹ is substituted or unsubstituted aryl, such as substituted or unsubstituted phenyl, and R² is substituted or unsubstituted aryl, such as substituted or unsubstituted phenyl.

In another embodiment, the TOR kinase inhibitors of formula (II) are those wherein —X-A-B—Y— taken together form —N(R²)C(O)NH—, R¹ is substituted or unsubstituted aryl, such as substituted or unsubstituted phenyl, R² is substituted or unsubstituted aryl, such as substituted or unsubstituted phenyl, and R³ and R⁴ are H.

In another embodiment, the TOR kinase inhibitors of formula (II) are those wherein —X-A-B—Y— taken together form —N(R²)C(O)NH—, L is a direct bond, R¹ is substituted or unsubstituted aryl, such as substituted or unsubstituted phenyl, R² is substituted or unsubstituted aryl, such as substituted or unsubstituted phenyl, and R³ and R⁴ are H.

In another embodiment, the TOR kinase inhibitors of formula (II) are those wherein —X-A-B—Y— taken together form —N(R²)C(O)NH—, R¹ is substituted or unsubstituted heteroaryl, L is a direct bond and R² is substituted or unsubstituted C$_{1-8}$alkyl or substituted or unsubstituted cycloalkyl.

In another embodiment, the TOR kinase inhibitors of formula (II) are those wherein —X-A-B—Y— taken together form —N(R²)C(O)NH—, R¹ is substituted or unsubstituted aryl, L is a direct bond and R² is substituted or unsubstituted C$_{1-8}$alkyl or substituted or unsubstituted cycloalkyl.

In another embodiment, the TOR kinase inhibitors of formula (II) do not include 8,9-dihydro-8-oxo-9-phenyl-2-(3-pyridinyl)-7H-purine-6-carboxamide, 8,9-dihydro-8-oxo-9-phenyl-2-(3-pyridinyl)-7H-purine-6-carboxamide, 8,9-dihydro-8-oxo-9-phenyl-2-(3-pyridinyl)-7H-purine-6-carboxamide, 2-(4-cyanophenyl)-8-oxo-9-phenyl-8,9-dihydro-7H-purine-6-carboxamide, 2-(4-nitrophenyl)-8-oxo-9-phenyl-8,9-dihydro-7H-purine-6-carboxamide, 9-benzyl-2-(4-methoxyphenyl)-8-oxo-8,9-dihydro-7H-purine-6-carboxamide, 2-methyl-8-oxo-9-phenyl-8,9-dihydro-7H-purine-6-carboxamide, 9-benzyl-9H-purine-2,6-dicarboxamide, 9-[2,3-bis[(benzoyloxy)methyl]cyclobutyl]-2-methyl-9H-Purine-6-carboxamide, 9-benzyl-2-methyl-9H-purine-6-carboxamide, 9-(2-hydroxyethyl)-2-methyl-9H-purine-6-carboxamide, 9-(2-hydroxyethyl)-2-(trifluoromethyl)-9H-purine-6-carboxamide, 9-(2-hydroxyethyl)-2-(prop-1-enyl)-9H-purine-6-carboxamide, 9-(2-hydroxyethyl)-2-phenyl-9H-purine-6-carboxamide, 9-(3-hydroxypropyl)-2-methyl-9H-purine-6-carboxamide, 9-(3-hydroxypropyl)-2-(trifluoromethyl)-9H-purine-6-carboxamide, 2-methyl-9-phenylmethyl-9H-purine-6-carboxamide or 2-methyl-9-β-D-ribofuranosyl-9H-purine-6-carboxamide.

In another embodiment, the TOR kinase inhibitors of formula (II) do not include compounds wherein R² is a substituted furanoside.

In another embodiment, the TOR kinase inhibitors of formula (II) do not include compounds wherein R² is a substituted or unsubstituted furanoside.

In another embodiment, the TOR kinase inhibitors of formula (II) do not include (2'R)-2'-deoxy-2'-fluoro-2'-C-methyl nucleosides.

In one embodiment, the TOR kinase inhibitors include compounds having the following formula (IIa):

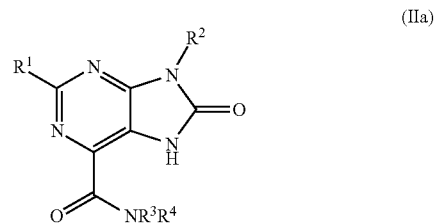

and pharmaceutically acceptable salts, clathrates, solvates, stereoisomers, tautomers, and prodrugs thereof, wherein:

R¹ is substituted or unsubstituted C$_{1-8}$alkyl, substituted or unsubstituted aryl, substituted or unsubstituted heteroaryl, substituted or unsubstituted cycloalkyl, or substituted or unsubstituted heterocyclylalkyl;

R² is substituted or unsubstituted C$_{1-8}$alkyl, substituted or unsubstituted aryl, substituted or unsubstituted heteroaryl, substituted or unsubstituted cycloalkyl, or substituted or unsubstituted heterocyclylalkyl; and R³ and R⁴ are independently H or C$_{1-8}$alkyl.

In one embodiment, the TOR kinase inhibitors of formula (IIa) are those wherein R¹ is substituted aryl, substituted or unsubstituted heteroaryl, such as substituted phenyl.

In another embodiment, the TOR kinase inhibitors of formula (IIa) are those wherein R¹ is substituted or unsubstituted heteroaryl, such as substituted or unsubstituted pyridine, substituted or unsubstituted indole or substituted or unsubstituted quinoline.

In another embodiment, the TOR kinase inhibitors of formula (IIa) are those wherein R¹ is substituted or unsubstituted cycloalkyl, such as substituted or unsubstituted cyclopentyl.

In another embodiment, the TOR kinase inhibitors of formula (IIa) are those wherein R² is substituted C$_{1-8}$alkyl, such as —CH₂C₆H₅.

In another embodiment, the TOR kinase inhibitors of formula (IIa) are those wherein R² is unsubstituted C$_{1-8}$alkyl, such as unsubstituted methyl.

In another embodiment, the TOR kinase inhibitors of formula (IIa) are those wherein R² is substituted or unsubstituted aryl, such as substituted or unsubstituted phenyl.

In another embodiment, the TOR kinase inhibitors of formula (IIa) are those wherein R² is substituted aryl, such as halo, haloalkyl or alkoxy substituted phenyl.

In another embodiment, the TOR kinase inhibitors of formula (IIa) are those wherein R² is substituted or unsubstituted cycloalkyl, such as substituted or unsubstituted cyclohexyl or substituted or unsubstituted cycloheptyl.

In another embodiment, the TOR kinase inhibitors of formula (IIa) are those wherein R² is substituted heterocyclylalkyl, such as substituted piperidine.

In another embodiment, the TOR kinase inhibitors of formula (IIa) are those wherein R³ and R⁴ are H.

In another embodiment, the TOR kinase inhibitors of formula (IIa) do not include 8,9-dihydro-8-oxo-9-phenyl-2-(3-pyridinyl)-7H-Purine-6-carboxamide, 8,9-dihydro-8-oxo-9-phenyl-2-(3-pyridinyl)-7H-Purine-6-carboxamide, 8,9-dihydro-8-oxo-9-phenyl-2-(3-pyridinyl)-7H-Purine-6-carboxamide, 2-(4-cyanophenyl)-8-oxo-9-phenyl-8,9-dihydro-7H-purine-6-carboxamide, 2-(4-nitrophenyl)-8-oxo-9-phenyl-8,9-dihydro-7H-purine-6-carboxamide, 9-benzyl- 2-(4-methoxyphenyl)-8-oxo-8,9-dihydro-7H-purine-6-carboxamide, 9-phenylmethyl-9H-purine-2,6-dicarboxamide, or 2-methyl-8-oxo-9-phenyl-8,9-dihydro-7H-purine-6-carboxamide.

In another embodiment, the TOR kinase inhibitors of formula (IIa) do not include compounds wherein $R^2$ is a substituted furanoside.

In another embodiment, the TOR kinase inhibitors of formula (IIa) do not include compounds wherein $R^2$ is a substituted or unsubstituted furanoside.

In another embodiment, the TOR kinase inhibitors of formula (IIa) do not include (2'R)-2'-deoxy-2'-fluoro-2'-C-methyl nucleosides.

In one embodiment, the TOR kinase inhibitors include compounds having the following formula (IIb):

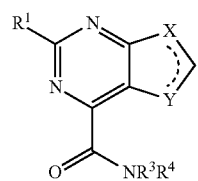

and pharmaceutically acceptable salts, clathrates, solvates, stereoisomers, tautomers, and prodrugs thereof, wherein:

is —C($R^2$)=CH—NH— or —N($R^2$)—CH=N—;

$R^1$ is substituted or unsubstituted $C_{1-8}$alkyl, substituted or unsubstituted aryl, substituted or unsubstituted heteroaryl, substituted or unsubstituted cycloalkyl, or substituted or unsubstituted heterocyclylalkyl;

$R^2$ is substituted or unsubstituted $C_{1-8}$alkyl, substituted or unsubstituted aryl, substituted or unsubstituted heteroaryl, substituted or unsubstituted cycloalkyl, or substituted or unsubstituted heterocyclylalkyl; and $R^3$ and $R^4$ are independently H or $C_{1-8}$alkyl.

In one embodiment, the TOR kinase inhibitors of formula (IIb) are those wherein $R^1$ is substituted aryl, such as substituted phenyl.

In another embodiment, the TOR kinase inhibitors of formula (IIb) are those wherein $R^1$ is substituted or unsubstituted heteroaryl, such as substituted or unsubstituted pyridine, substituted or unsubstituted indole or substituted or unsubstituted quinoline.

In another embodiment, the TOR kinase inhibitors of formula (IIb) are those wherein $R^1$ is substituted or unsubstituted cycloalkyl, such as substituted or unsubstituted cyclopentyl.

In another embodiment, the TOR kinase inhibitors of formula (IIb) are those wherein $R^2$ is substituted $C_{1-8}$alkyl, such as —$CH_2C_6H_5$.

In another embodiment, the TOR kinase inhibitors of formula (IIb) are those wherein $R^2$ is unsubstituted $C_{1-8}$alkyl, such as unsubstituted methyl.

In another embodiment, the TOR kinase inhibitors of formula (IIb) are those wherein $R^2$ is substituted or unsubstituted aryl, such as substituted or unsubstituted phenyl.

In another embodiment, the TOR kinase inhibitors of formula (IIb) are those wherein $R^2$ is substituted aryl, such as halo, haloalkyl or alkoxy substituted phenyl.

In another embodiment, the TOR kinase inhibitors of formula (IIb) are those wherein $R^2$ is substituted or unsubstituted cycloalkyl, such as substituted or unsubstituted cyclohexyl or substituted or unsubstituted cycloheptyl.

In another embodiment, the TOR kinase inhibitors of formula (IIb) are those wherein $R^2$ is substituted heterocyclylalkyl, such as substituted piperidine.

In another embodiment, the TOR kinase inhibitors of formula (IIb) are those wherein $R^3$ and $R^4$ are H.

In another embodiment, the TOR kinase inhibitors of formula (IIb) are those wherein

is —C($R^2$)=CH—NH— and $R^2$ is substituted aryl, such as substituted phenyl.

In another embodiment, the TOR kinase inhibitors of formula (IIb) are those wherein

is —N($R^2$)—CH=N— and $R^2$ is substituted aryl, such as substituted phenyl.

In another embodiment, the TOR kinase inhibitors of formula (IIb) are those wherein $R^1$ is substituted aryl, such as phenyl, and $R^2$ is substituted aryl, such as substituted phenyl.

In another embodiment, the TOR kinase inhibitors of formula (IIb) do not include 9-benzyl-9H-purine-2,6-dicarboxamide, 9-[2,3-bis[(benzoyloxy)methyl]cyclobutyl]-2-methyl-9H-Purine-6-carboxamide, 9-benzyl-2-methyl-9H-purine-6-carboxamide, 9-(2-hydroxyethyl)-2-methyl-9H-purine-6-carboxamide, 9-(2-hydroxyethyl)-2-(trifluoromethyl)-9H-purine-6-carboxamide, 9-(2-hydroxyethyl)-2-(prop-1-enyl)-9H-purine-6-carboxamide, 9-(2-hydroxyethyl)-2-phenyl-9H-purine-6-carboxamide, 9-(3-hydroxypropyl)-2-methyl-9H-purine-6-carboxamide, 9-(3-hydroxypropyl)-2-(trifluoromethyl)-9H-purine-6-carboxamide, 9-phenylmethyl-9H-purine-2,6-dicarboxamide, 2-methyl-9-phenylmethyl-9H-purine-6-carboxamide or 2-methyl-9-β-D-ribofuranosyl-9H-purine-6-carboxamide.

In another embodiment, the TOR kinase inhibitors of formula (IIb) do not include compounds wherein $R^2$ is substituted cyclobutyl when

is —N($R^2$)—CH=N—.

In another embodiment, the TOR kinase inhibitors of formula (IIb) do not include compounds wherein $R^2$ is a substituted furanoside when

is —N($R^2$)—CH=N—.

In another embodiment, the TOR kinase inhibitors of formula (IIb) do not include compounds wherein $R^2$ is substituted pyrimidine when

is —C($R^2$)=CH—NH—.

In another embodiment, the TOR kinase inhibitors of formula (IIb) do not include compounds wherein $R^2$ is substituted oxetane when

is —N($R^2$)—CH=N—.

In another embodiment, the TOR kinase inhibitors of formula (IIb) do not include compounds wherein $R^2$ is substituted cyclopentyl or a heterocyclopentyl when

is —N($R^2$)—CH=N—.

In one embodiment, the TOR kinase inhibitors include compounds having the following formula (IIc):

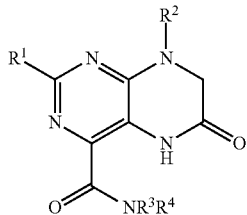

(IIc)

and pharmaceutically acceptable salts, clathrates, solvates, stereoisomers, tautomers, and prodrugs thereof, wherein:

$R^1$ is substituted or unsubstituted $C_{1-8}$alkyl, substituted or unsubstituted aryl, substituted or unsubstituted heteroaryl, substituted or unsubstituted cycloalkyl, or substituted or unsubstituted heterocyclylalkyl;

$R^2$ is substituted or unsubstituted $C_{1-8}$alkyl, substituted or unsubstituted aryl, substituted or unsubstituted heteroaryl, substituted or unsubstituted cycloalkyl, or substituted or unsubstituted heterocyclylalkyl; and $R^3$ and $R^4$ are independently H or $C_{1-8}$alkyl.

In one embodiment, the TOR kinase inhibitors of formula (IIc) are those wherein $R^1$ is substituted aryl, such as substituted phenyl.

In another embodiment, the TOR kinase inhibitors of formula (IIc) are those wherein $R^1$ is substituted or unsubstituted heteroaryl, such as substituted or unsubstituted pyridine, substituted or unsubstituted indole or substituted or unsubstituted quinoline.

In another embodiment, the TOR kinase inhibitors of formula (IIc) are those wherein $R^1$ is substituted or unsubstituted cycloalkyl, such as substituted or unsubstituted cyclopentyl.

In another embodiment, the TOR kinase inhibitors of formula (IIc) are those wherein $R^2$ is substituted $C_{1-8}$alkyl, such as —$CH_2C_6H_5$.

In another embodiment, the TOR kinase inhibitors of formula (IIc) are those wherein $R^2$ is unsubstituted $C_{1-8}$alkyl, such as unsubstituted methyl.

In another embodiment, the TOR kinase inhibitors of formula (IIc) are those wherein $R^2$ is substituted or unsubstituted aryl, such as substituted or unsubstituted phenyl.

In another embodiment, the TOR kinase inhibitors of formula (IIc) are those wherein $R^2$ is substituted aryl, such as halo, haloalkyl or alkoxy substituted phenyl.

In another embodiment, the TOR kinase inhibitors of formula (IIc) are those wherein $R^2$ is substituted or unsubstituted cycloalkyl, such as substituted or unsubstituted cyclohexyl or substituted or unsubstituted cycloheptyl.

In another embodiment, the TOR kinase inhibitors of formula (IIc) are those wherein $R^2$ is substituted heterocyclylalkyl, such as substituted piperidine.

In another embodiment, the TOR kinase inhibitors of formula (IIc) are those wherein $R^3$ and $R^4$ are H.

In one embodiment, the TOR kinase inhibitors include compounds having the following formula (IId):

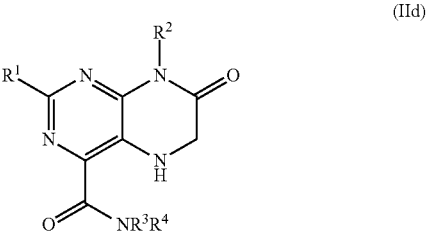

(IId)

and pharmaceutically acceptable salts, clathrates, solvates, stereoisomers, tautomers, and prodrugs thereof, wherein:

$R^1$ is substituted or unsubstituted $C_{1-8}$alkyl, substituted or unsubstituted aryl, substituted or unsubstituted heteroaryl, substituted or unsubstituted cycloalkyl, or substituted or unsubstituted heterocyclylalkyl;

$R^2$ is substituted or unsubstituted $C_{1-8}$alkyl, substituted or unsubstituted aryl, substituted or unsubstituted heteroaryl, substituted or unsubstituted cycloalkyl, or substituted or unsubstituted heterocyclylalkyl; and $R^3$ and $R^4$ are independently H or $C_{1-8}$alkyl.

In one embodiment, the TOR kinase inhibitors of formula (IId) are those wherein $R^1$ is substituted aryl, such as substituted phenyl.

In another embodiment, the TOR kinase inhibitors of formula (IId) are those wherein $R^1$ is substituted or unsubstituted heteroaryl, such as substituted or unsubstituted pyridine, substituted or unsubstituted indole or substituted or unsubstituted quinoline.

In another embodiment, the TOR kinase inhibitors of formula (IId) are those wherein $R^1$ is substituted or unsubstituted cycloalkyl, such as substituted or unsubstituted cyclopentyl.

In another embodiment, the TOR kinase inhibitors of formula (IId) are those wherein $R^2$ is substituted $C_{1-8}$alkyl, such as —$CH_2C_6H_5$.

In another embodiment, the TOR kinase inhibitors of formula (IId) are those wherein $R^2$ is unsubstituted $C_{1-8}$alkyl, such as unsubstituted methyl.

In another embodiment, the TOR kinase inhibitors of formula (IId) are those wherein $R^2$ is substituted or unsubstituted aryl, such as substituted or unsubstituted phenyl.

In another embodiment, the TOR kinase inhibitors of formula (IId) are those wherein $R^2$ is substituted aryl, such as halo, haloalkyl or alkoxy substituted phenyl.

In another embodiment, the TOR kinase inhibitors of formula (IId) are those wherein $R^2$ is substituted or unsubstituted cycloalkyl, such as substituted or unsubstituted cyclohexyl or substituted or unsubstituted cycloheptyl.

In another embodiment, the TOR kinase inhibitors of formula (IId) are those wherein $R^2$ is substituted heterocyclylalkyl, such as substituted piperidine.

In another embodiment, the TOR kinase inhibitors of formula (IId) are those wherein $R^3$ and $R^4$ are H.

Representative TOR kinase inhibitors of formula (II) include compounds from Table B.

TABLE B 9-benzyl-8-oxo-2-(pyridin-3-yl)-8,9-dihydro-7H-purine-6-carboxamide;
N-methyl-8-oxo-9-phenyl-2-(pyridin-3-yl)-8,9-dihydro-7H-purine-6-carboxamide;
8-oxo-9-phenyl-2-(pyridin-2-yl)-8,9-dihydro-7H-purine-6-carboxamide;
2-(2-chloropyridin-3-yl)-8-oxo-9-phenyl-8,9-dihydro-7H-purine-6-carboxamide;
2-(2-methoxypyridin-3-yl)-8-oxo-9-phenyl-8,9-dihydro-7H-purine-6-carboxamide;
N,N-dimethyl-8-oxo-9-phenyl-2-(pyridin-3-yl)-8,9-dihydro-7H-purine-6-carboxamide;
9-methyl-8-oxo-2-(pyridin-3-yl)-8,9-dihydro-7H-purine-6-carboxamide;
2-(4-hydroxyphenyl)-9-(2-methoxyphenyl)-8-oxo-8,9-dihydro-7H-purine-6-carboxamide;
2-(3-hydroxyphenyl)-8-oxo-9-o-tolyl-8,9-dihydro-7H-purine-6-carboxamide;
2-(1H-indol-4-yl)-9-(2-methoxyphenyl)-8-oxo-8,9-dihydro-7H-purine-6-carboxamide;
2-(1H-indol-6-yl)-9-(2-methoxyphenyl)-8-oxo-8,9-dihydro-7H-purine-6-carboxamide;
2-(3-hydroxyphenyl)-9-(4-methoxyphenyl)-8-oxo-8,9-dihydro-7H-purine-6-carboxamide;
2-(2-hydroxypyridin-4-yl)-9-(2-methoxyphenyl)-8-oxo-8,9-dihydro-7H-purine-6-carboxamide;
9-(2-chlorophenyl)-2-(3-hydroxyphenyl)-8-oxo-8,9-dihydro-7H-purine-6-carboxamide;
9-(2-fluorophenyl)-2-(3-hydroxyphenyl)-8-oxo-8,9-dihydro-7H-purine-6-carboxamide;
9-(2,6-difluorophenyl)-2-(3-hydroxyphenyl)-8-oxo-8,9-dihydro-7H-purine-6-carboxamide;
9-cycloheptyl-8-oxo-2-(pyridin-3-yl)-8,9-dihydro-7H-purine-6-carboxamide;
9-(2-methoxyphenyl)-8-oxo-2-(quinolin-5-yl)-8,9-dihydro-7H-purine-6-carboxamide;
2-cyclopentyl-9-(2-methoxyphenyl)-8-oxo-8,9-dihydro-7H-purine-6-carboxamide;
9-(2-methoxyphenyl)-8-oxo-2-(3-(trifluoromethyl)phenyl)-8,9-dihydro-7H-purine-6-carboxamide;
9-(2-methoxyphenyl)-2-(6-methoxypyridin-3-yl)-8-oxo-8,9-dihydro-7H-purine-6-carboxamide;
2-(3-hydroxyphenyl)-8-oxo-9-(4-(trifluoromethyl)phenyl)-8,9-dihydro-7H-purine-6-carboxamide;
9-benzyl-2-(3-hydroxyphenyl)-8-oxo-8,9-dihydro-7H-purine-6-carboxamide;
2-(3-hydroxyphenyl)-8-oxo-9-(2-(trifluoromethoxy)phenyl)-8,9-dihydro-7H-purine-6-carboxamide;
9-(2,4-dichlorophenyl)-2-(3-hydroxyphenyl)-8-oxo-8,9-dihydro-7H-purine-6-carboxamide;
9-(2-methoxyphenyl)-2-(3-nitrophenyl)-8-oxo-8,9-dihydro-7H-purine-6-carboxamide;
2-(3-cyanophenyl)-8-oxo-9-phenyl-8,9-dihydro-7H-purine-6-carboxamide;
9-(3-fluorophenyl)-2-(3-hydroxyphenyl)-8-oxo-8,9-dihydro-7H-purine-6-carboxamide;
9-(2-methoxyphenyl)-8-oxo-2-(2-(trifluoromethyl)phenyl)-8,9-dihydro-7H-purine-6-carboxamide;
2-(5-fluoropyridin-3-yl)-9-(2-methoxyphenyl)-8-oxo-8,9-dihydro-7H-purine-6-carboxamide;
2-(1-benzylpiperidin-4-yl)-9-(2-methoxyphenyl)-8-oxo-8,9-dihydro-7H-purine-6-carboxamide;
benzyl 4-(6-carbamoyl-8-oxo-2-(pyridin-3-yl)-7H-purin-9(8H)-yl)piperidine-1-carboxylate;
9-cyclohexyl-2-(3-hydroxyphenyl)-8-oxo-8,9-dihydro-7H-purine-6-carboxamide;
9-(2-methoxyphenyl)-8-oxo-2-(3-(trifluoromethoxy)phenyl)-8,9-dihydro-7H-purine-6-carboxamide;
9-phenyl-2-(pyridin-3-yl)-9H-purine-6-carboxamide;
6-oxo-8-phenyl-2-(pyridin-3-yl)-5,6,7,8-tetrahydropteridine-4-carboxamide;
6-oxo-8-phenyl-2-(pyridin-4-yl)-5,6,7,8-tetrahydropteridine-4-carboxamide;
2-(3-aminophenyl)-9-(2-methoxyphenyl)-8-oxo-8,9-dihydro-7H-purine-6-carboxamide;
2-(3-hydroxyphenyl)-9-(2-methoxyphenyl)-9H-purine-6-carboxamide;
9-Cyclopentyl-2-(3-hydroxyphenyl)-8-oxo-8,9-dihydro-7H-purine-6-carboxamide;
9-tert-Butyl-2-(3-hydroxy-phenyl)-8-oxo-8,9-dihydo-7H-purine-6-carboxamide;
[2-(3-Hydroxyphenyl)-9-(2-methoxyphenyl)-8-oxo(7-hydropurin-6-yl)]-N-methylcarbox-amide;
2-phenyl-5H-pyrrolo[3,2-d]pyrimidine-4-carboxamide;
[2-(3-Hydroxyphenyl)-9-(2-methoxyphenyl)-8-oxo(7-hydropurin-6-yl)]-N,N-dimethyl carboxamide;
2-(3-Hydroxyphenylamino)-9-(2-methoxyphenyl)-8-oxo-8,9-dihydro-7H-purine-6-carboxamide;
2-(4-Hydroxyphenylamino)-9-(2-methoxyphenyl)-8-oxo-8,9-dihydro-7H-purine-6-carboxamide;
9-(trans-4-Hydroxycyclohexyl)-2-(3-hydroxyphenyl)-8-oxo-8,9-dihydro-7H-purine-6-carboxamide;
9-(trans-4-Hydroxycyclohexyl)-8-oxo-2-(pyridin-3-yl)-8,9-dihydro-7H-purine-6-carboxamide;
9-(trans-4-Hydroxycyclohexyl)-2-(3-hydroxyphenyl)-8-oxo-8,9-dihydro-7H-purine-6-carboxamide;
9-(trans-4-Hydroxycyclohexyl)-8-oxo-2-(pyridin-3-yl)-8,9-dihydro-7H-purine-6-carboxamide;
2-(3-Hydroxyphenylamino)-9-(2-methoxyphenyl)-9H-purine-6-carboxamide;
9-Isopropyl-2-(3-hydroxy-phenyl)-8-oxo-8,9-dihydo-7H-purine-6-carboxamide;
Methyl 4-(6-carbamoyl-9-(2-methoxyphenyl)-8-oxo-8,9-dihydro-7H-purin-2-yl) benzoate;
2-(2-Chloro-3-hydroxyphenyl)-9-(2-methoxyphenyl)-8-oxo-7-hydropurine-6-carbox amide;
2-(3-Cyanophenyl)-9-(2-methoxyphenyl)-8-oxo-8,9-dihydro-7H-purine-6-carboxamide;
2-(2-Hydroxyphenylamino)-9-(2-methoxyphenyl)-8-oxo-8,9-dihydro-7H-purine-6-carboxamide;
2-(3-Hydroxyphenyl)-9-(4-methoxy-2-methylphenyl)-8-oxo-8,9-dihydro-7H-purine-6-carboxamide;
2-(3-Hydroxyphenyl)-8-oxo-9-(2-(trifluoromethyl)phenyl)-8,9-dihydro-7H-purine-6-carboxamide;

TABLE B-continued 2-(4-Cyano-phenyl)-9-(2-methoxy-phenyl)-8-oxo-8,9-dihydro-7H-purine-6-carboxamide;
4-[6-Carbamoyl-9-(2-methoxy-phenyl)-8-oxo-8,9-dihydro-7H-purin-2-yl]-benzoic acid;
Methyl 3-(6-carbamoyl-9-(2-methoxyphenyl)-8-oxo-8,9-dihydro-7H-purin-2-yl)benzoate;
3-(6-Carbamoyl-9-(2-methoxyphenyl)-8-oxo-8,9-dihydro-7H-purin-2-yl)benzoic acid;
2-(3-Hydroxyphenyl)-9-(2-isopropylphenyl)-8-oxo-8,9-dihydro-7H-purine-6-carboxamide;
2-(1H-Indazol-6-yl)-9-(2-methoxyphenyl)-8-oxo-7-hydropurine-6-carboxamide;
2-(4-Carbamoylphenyl)-9-(2-methoxyphenyl)-8-oxo-8,9-dihydro-7H-purine-6-carboxamide;
9-(2-Ethylphenyl)-2-(3-hydroxyphenyl)-8-oxo-8,9-dihydro-7H-purine-6-carboxamide;
9-(2,5-Dichlorophenyl)-2-(3-hydroxyphenyl)-8-oxo-7-hydropurine-6-carboxamide;
2-(3-Carbamoylphenyl)-9-(2-methoxyphenyl)-8-oxo-8,9-dihydro-7H-purine-6-carbox amide;
9-(2,6-Dichlorophenyl)-2-(3-hydroxyphenyl)-8-oxo-7-hydropurine-6-carboxamide;
2-(Hydroxyphenyl)-9-(2-methoxyphenyl)purine-6-carboxamide;
2-(1H-Indazol-5-yl)-9-(2-methoxyphenyl)-8-oxo-7-hydropurine-6-carboxamide;
9-(2,3-Dichlorophenyl)-2-(3-hydroxyphenyl)-8-oxo-7-hydropurine-6-carboxamide;
2-[4-(Hydroxymethyl)phenyl]-9-(2-methoxyphenyl)-8-oxo-7-hydropurine-6-carbox-amide;
2-[3-(Hydroxymethyl)phenyl]-9-(2-methoxyphenyl)-8-oxo-7-hydropurine-6-carbox-amide;
9-(2-Methoxyphenyl)-8-oxo-2-(pyridin-4-yl)-8,9-dihydro-7H-purine-6-carboxamide;
2-(4-Fluoro-3-hydroxyphenyl)-9-(2-methoxyphenyl)-8-oxo-7-hydropurine-6-carbox-amide;
2-(2-Fluoro-3-hydroxyphenyl)-9-(2-methoxyphenyl)-8-oxo-7-hydropurine-6-carbox-amide;
2-[4-(1-Hydroxy-isopropyl)phenyl]-9-(2-methoxyphenyl)-8-oxo-7-hydropurine-6-carboxamide;
2-[3-(1-Hydroxy-isopropyl)phenyl]-9-(2-methoxyphenyl)-8-oxo-7-hydropurine-6-carboxamide;
9-(2-Methoxyphenyl)-2-(2-nitrophenyl)-8-oxo-7-hydropurine-6-carboxamide;
9-(2-Methoxyphenyl)-2-(4-nitrophenyl)-8-oxo-7-hydropurine-6-carboxamide;
9-(2-Methoxyphenyl)-2-(2-nitrophenyl)-8-oxo-7-hydropurine-6-carboxamide;
9-(2,4-Difluorophenyl)-2-(3-hydroxyphenyl)-8-oxo-7-hydropurine-6-carboxamide;
9-(2-Methoxyphenyl)-2-{3-[(methylsulfonyl)amino]phenyl}-8-oxo-7-hydropurine-6-carboxamide;
9-(4-Chloro-2-fluorophenyl)-2-(3-hydroxyphenyl)-8-oxo-7-hydropurine-6-carboxamide;
9-(2-Chlorophenyl)-8-oxo-2-(3-pyridyl)-7-hydropurine-6-carboxamide;
8-Oxo-2-(3-pyridyl)-9-[2-(trifluoromethyl)phenyl]-7-hydropurine-6-carboxamide;
9-(3-Chloro-2-fluorophenyl)-2-(3-hydroxyphenyl)-8-oxo-7-hydropurine-6-carboxamide;
9-(2-Fluoro-3-trifluoromethylphenyl)-2-(3-hydroxyphenyl)-8-oxo-7-hydropurine-6-carboxamide;
9-(2,3,4-Trifluorophenyl)-2-(3-hydroxyphenyl)-8-oxo-7-hydropurine-6-carboxamide;
2-(1H-Benzo[d]imidazol-6-yl)-9-(2-methoxyphenyl)-8-oxo-8,9-dihydro-7H-purine-6-carboxamide;
2-[3-(Acetylamino)phenyl]-9-(2-methoxyphenyl)-8-oxo-7-hydropurine-6-carboxamide;
2-(3-hydroxyphenyl)-8-(2-methoxyphenyl)-6-oxo-5,6,7,8-tetrahydropteridine-4-carbox-amide;
9-(2-Methoxyphenyl)-8-oxo-2-pyrazol-4-yl-7-hydropurine-6-carboxamide;
9-(2-Methoxyphenyl)-8-oxo-2-pyrazol-3-yl-7-hydropurine-6-carboxamide;
9-(4-Aminocyclohexyl)-2-(3-hydroxyphenyl)-8-oxo-7-hydropurine-6-carboxamide;
2-[3-(Difluoromethyl)phenyl]-9-(2-methoxyphenyl)-8-oxo-7-hydropurine-6-carbox-amide;
2-[5-(Difluoromethyl)-2-fluorophenyl]-9-(2-methoxyphenyl)-8-oxo-7-hydropurine-6-carboxamide;
2-(1H-benzo[d]imidazol-4-yl)-9-(2-methoxyphenyl)-8-oxo-8,9-dihydro-7H-purine-6-carboxamide;
2-(6-Hydroxypyridin-3-yl)-8-oxo-9-(2-(trifluoromethyl)phenyl)-8,9-dihydro-7H-purine-6-carboxamide;
2-(1H-benzo[d]imidazol-6-yl)-9-(2-fluorophenyl)-8-oxo-8,9-dihydro-7H-purine-6-carboxamide;
2-Benzimidazol-6-yl-8-oxo-9-[2-(trifluoromethyl)phenyl]-7-hydropurine-6-carboxamide;
2-(5-Chloropyridin-3-yl)-8-oxo-9-(2-(trifluoromethyl)phenyl)-8,9-dihydro-7H-purine-6-carboxamide;
trans-4-(6-Carbamoyl-9-(2-methoxyphenyl)-8-oxo-8,9-dihydro-7H-purin-2-ylamino) cyclohexyl carbamate;
(R)-9-(2-Methoxyphenyl)-8-oxo-2-(pyrrolidin-3-ylamino)-8,9-dihydro-7H-purine-6-carboxamide;
(S)-9-(2-Methoxyphenyl)-8-oxo-2-(pyrrolidin-3-ylamino)-8,9-dihydro-7H-purine-6-carboxamide;
(cis)-4-(6-Carbamoyl-9-(2-methoxyphenyl)-8-oxo-8,9-dihydro-7H-purin-2-ylamino) cyclohexyl carbamate;
2-(trans-4-Hydroxycyclohexylamino)-9-(2-methoxyphenyl)-8-oxo-8,9-dihydro-7H-purine-6-carboxamide;
2-(4-Chloropyridin-3-yl)-8-oxo-9-(2-(trifluoromethyl)phenyl)-8,9-dihydro-7H-purine-6-carboxamide;
2-(cis-4-Hydroxycyclohexylamino)-9-(2-methoxyphenyl)-8-oxo-8,9-dihydro-7H-purine-6-carboxamide;
2-(4-((1H-Imidazol-1-yl)methyl)phenylamino)-9-(2-methoxyphenyl)-8-oxo-8,9-dihydro-7H-purine-6-carboxamide;
2-(4-Hydroxypyridin-3-yl)-8-oxo-9-(2-(trifluoromethyl)phenyl)-8,9-dihydro-7H-purine-6-carboxamide;
(R)-9-(2-Methoxyphenyl)-8-oxo-2-(pyrrolidin-2-ylmethylamino)-8,9-dihydro-7H-purine-6-carboxamide;
(S)-9-(2-Methoxyphenyl)-8-oxo-2-(pyrrolidin-2-ylmethylamino)-8,9-dihydro-7H-purine-6-carboxamide;
2-(4-(1H-1,2,4-Triazol-3-yl)phenyl)-9-(2-methoxyphenyl)-8-oxo-7-hydropurine-6-carboxamide;
2-(2-Hydroxyethylamino)-9-(2-methoxyphenyl)-8-oxo-8,9-dihydro-7H-purine-6-carboxamide;
9-(2-Methoxyphenyl)-8-oxo-2-(2-(trifluoromethyl)-1H-benzo[d]imidazol-6-yl)-8,9-dihydro-7H-purine-6-carboxamide;
2-(3-(1H-1,2,4-Triazol-3-yl)phenyl)-9-(2-methoxyphenyl)-8-oxo-7-hydropurine-6-carboxamide;
9-(Biphenyl-2-yl)-2-(3-hydroxyphenyl)-8-oxo-8,9-dihydro-7H-purine-6-carboxamide;

TABLE B-continued 2-(4-(1H-1,2,4-Triazol-3-yl)phenyl)-9-(2-fluorophenyl)-8-oxo-7-hydropurine-6-carboxamide;
2-(4-(1H-1,2,4-Triazol-3-yl)phenyl)-9-(2-isopropylphenyl)-8-oxo-8,9-dihydro-7H-purine-6-carboxamide;
9-(2-Methoxyphenyl)-2-(2-methyl-1H-benzo[d]imidazol-6-yl)-8-oxo-8,9-dihydro-7H-purine-6-carboxamide;
2-(3-(Hydroxymethyl)phenylamino)-9-(2-methoxyphenyl)-8-oxo-8,9-dihydro-7H-purine-6-carboxamide;
2-(2-(Hydroxymethyl)phenylamino)-9-(2-methoxyphenyl)-8-oxo-8,9-dihydro-7H-purine-6-carboxamide;
9-(2-tert-Butylphenyl)-2-(3-hydroxyphenyl)-8-oxo-8,9-dihydro-7H-purine-6-carboxamide;
2-(3-Hydroxyphenyl)-8-oxo-9-(2-phenoxyphenyl)-8,9-dihydro-7H-purine-6-carboxamide;
2-(1H-Benzo[d]imidazol-6-yl)-9-(2-isopropylphenyl)-8-oxo-8,9-dihydro-7H-purine-6-carboxamide;
2-(1H-Indazol-4-yl)-9-(2-methoxyphenyl)-8-oxo-8,9-dihydro-7H-purine-6-carboxamide;
2-(2-Hydroxypyridin-3-yl)-8-oxo-9-(2-(trifluoromethyl)phenyl)-8,9-dihydro-7H-purine-6-carboxamide;
2-(1H-Imidazo[4,5-b]pyridin-6-yl)-9-(2-methoxyphenyl)-8-oxo-8,9-dihydro-7H-purine-6-carboxamide;
2-(4-(1H-Imidazol-1-yl)phenyl)-9-(2-isopropylphenyl)-8-oxo-8,9-dihydro-7H-purine-6-carboxamide;
9-(2-Cyclohexylphenyl)-2-(3-hydroxyphenyl)-8-oxo-8,9-dihydro-7H-purine-6-carboxamide;
2-(4-(1H-Imidazol-2-yl)phenyl)-9-(2-isopropylphenyl)-8-oxo-8,9-dihydro-7H-purine-6-carboxamide;
2-(1H-Benzo[d]imidazol-1-yl)-9-(2-methoxyphenyl)-8-oxo-8,9-dihydro-7H-purine-6-carboxamide;
2-(1H-Imidazo[4,5-b]pyridin-6-yl)-9-(2-isopropylphenyl)-8-oxo-8,9-dihydro-7H-purine-6-carboxamide;
9-(2-Isopropylphenyl)-8-oxo-2-(1H-pyrrolo[2,3-b]pyridin-5-yl)-8,9-dihydro-7H-purine-6-carboxamide;
2-(1H-Imidazo[4,5-b]pyridin-6-yl)-8-oxo-9-(2-(trifluoromethyl)phenyl)-8,9-dihydro-7H-purine-6-carboxamide;
9-(2-Methoxyphenyl)-2-(2-(methylthio)-1H-benzo[d]imidazol-5-yl)-8-oxo-8,9-dihydro-7H-purine-6-carboxamide;
2-(1H-Indol-5-yl)-9-(2-isopropylphenyl)-8-oxo-8,9-dihydro-7H-purine-6-carboxamide;
9-(Cyclohexylmethyl)-2-(3-hydroxyphenyl)-8-oxo-8,9-dihydro-7H-purine-6-carboxamide;
9-(2,3-Dihydro-1H-inden-1-yl)-2-(3-hydroxyphenyl)-8-oxo-8,9-dihydro-7H-purine-6-carboxamide;
2-(3-Hydroxyphenyl)-9-isobutyl-8-oxo-8,9-dihydro-7H-purine-6-carboxamide;
9-(trans-4-Methoxycyclohexyl)-2-(3-hydroxyphenyl)-8-oxo-8,9-dihydro-7H-purine-6-carboxamide;
9-(cis-4-Methoxycyclohexyl)-2-(3-hydroxyphenyl)-8-oxo-8,9-dihydro-7H-purine-6-carboxamide;
2-(3-Hydroxyphenyl)-8-oxo-9-(5,6,7,8-tetrahydronaphthalen-1-yl)-8,9-dihydro-7H-purine-6-carboxamide;
2-(4-(1H-1,2,4-Triazol-3-yl)phenyl)-9-cyclohexyl-8-oxo-8,9-dihydro-7H-purine-6-carboxamide;
2-(3-Hydroxyphenyl)-9-(1H-indol-4-yl)-8-oxo-8,9-dihydro-7H-purine-6-carboxamide;
9-(2-Fluoro-3-methoxyphenyl)-2-(3-hydroxyphenyl)-8-oxo-8,9-dihydro-7H-purine-6-carboxamide;
9-(2-Fluoro-5-methoxyphenyl)-2-(3-hydroxyphenyl)-8-oxo-8,9-dihydro-7H-purine-6-carboxamide;
9-Cyclohexyl-2-(1H-imidazo[4,5-b]pyridin-6-yl)-8-oxo-8,9-dihydro-7H-purine-6-carboxamide;
2-(3-Hydroxyphenyl)-8-oxo-9-(tetrahydro-2H-pyran-4-yl)-8,9-dihydro-7H-purine-6-carboxamide;
2-(3-Hydroxyphenyl)-8-oxo-9-((tetrahydro-2H-pyran-4-yl)methyl)-8,9-dihydro-7H-purine-6-carboxamide;
9-(2-Cyclopentylphenyl)-2-(3-hydroxyphenyl)-8-oxo-8,9-dihydro-7H-purine-6-carboxamide;
2-(3-Hydroxyphenyl)-8-oxo-9-(piperidin-4-yl)-8,9-dihydro-7H-purine-6-carboxamide;
9-(2-Fluoro-4-methoxyphenyl)-2-(3-hydroxyphenyl)-8-oxo-8,9-dihydro-7H-purine-6-carboxamide;
2-(1H-benzo[d]imidazol-6-yl)-9-cyclohexyl-8-oxo-8,9-dihydro-7H-purine-6-carboxamide;
2-Benzimidazol-6-yl-9-(trans-4-methoxycyclohexyl)-8-oxo-7-hydropurine-6-carboxamide;
2-(4-(Aminomethyl)phenyl)-9-(2-methoxyphenyl)-8-oxo-8,9-dihydro-7H-purine-6-carboxamide;
2-(3-Hydroxyphenyl)-9-(cis-4-(methoxymethyl)cyclohexyl)-8-oxo-8,9-dihydro-7H-purine-6-carboxamide;
9-(trans-4-Aminocyclohexyl)-2-(3-hydroxyphenyl)-8-oxo-8,9-dihydro-7H-purine-6-carboxamide;
2-(3-Hydroxyphenyl)-9-(2-isobutylphenyl)-8-oxo-8,9-dihydro-7H-purine-6-carboxamide;
(R)-2-(3-Hydroxyphenyl)-8-oxo-9-(tetrahydrofuran-3-yl)-8,9-dihydro-7H-purine-6-carboxamide;
(S)-2-(3-Hydroxyphenyl)-8-oxo-9-(tetrahydrofuran-3-yl)-8,9-dihydro-7H-purine-6-carboxamide;
2-(3-(Aminomethyl)phenyl)-9-(2-methoxyphenyl)-8-oxo-8,9-dihydro-7H-purine-6-carboxamide;
2-(4-(1H-1,2,3-Triazol-5-yl)phenyl)-9-(2-isopropylphenyl)-8-oxo-8,9-dihydro-7H-purine-6-carboxamide;
2-(4-(1H-1,2,4-Triazol-3-yl)phenyl)-9-(cis-4-methoxycyclohexyl)-8-oxo-8,9-dihydro-7H-purine-6-carboxamide;
2-(1H-Benzo[d]imidazol-6-yl)-9-(cis-4-methoxycyclohexyl)-8-oxo-8,9-dihydro-7H-purine-6-carboxamide;
2-(1H-Imidazo[4,5-b]pyridin-6-yl)-9-(cis-4-methoxycyclohexyl)-8-oxo-8,9-dihydro-7H-purine-6-carboxamide;

TABLE B-continued 2-(3-Hydroxyphenyl)-9-((1r,4r)-4-(methoxymethyl)cyclohexyl)-8-oxo-8,9-dihydro-7H-purine-6-carboxamide; and
9-(2-Isopropylphenyl)-2-(4-(5-methyl-4H-1,2,4-triazol-3-yl)phenyl)-8-oxo-8,9-dihydro-7H-purine-6-carboxamide,
and pharmaceutically acceptable salts, clathrates, solvates, stereoisomers, tautomers, and prodrugs thereof.

In one embodiment, the TOR kinase inhibitors include compounds having the following formula (III):

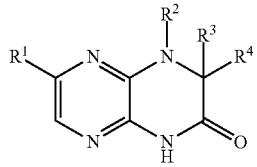

and pharmaceutically acceptable salts, clathrates, solvates, stereoisomers, tautomers, and prodrugs thereof, wherein:

$R^1$ is substituted or unsubstituted $C_{1-8}$ alkyl, substituted or unsubstituted aryl, substituted or unsubstituted cycloalkyl, substituted or unsubstituted heterocyclyl, or substituted or unsubstituted heterocyclylalkyl;

$R^2$ is H, substituted or unsubstituted $C_{1-8}$ alkyl, substituted or unsubstituted cycloalkyl, substituted or unsubstituted heterocyclyl, substituted or unsubstituted heterocyclylalkyl, substituted or unsubstituted aralkyl, or substituted or unsubstituted cycloalkylalkyl;

$R^3$ and $R^4$ are each independently H, substituted or unsubstituted $C_{1-8}$ alkyl, substituted or unsubstituted aryl, substituted or unsubstituted cycloalkyl, substituted or unsubstituted heterocyclyl, substituted or unsubstituted heterocyclylalkyl, substituted or unsubstituted aralkyl, substituted or unsubstituted cycloalkylalkyl, or $R^3$ and $R^4$, together with the atoms to which they are attached, form a substituted or unsubstituted cycloalkyl or substituted or unsubstituted heterocyclyl;

or $R^2$ and one of $R^3$ and $R^4$, together with the atoms to which they are attached, form a substituted or unsubstituted heterocyclyl, wherein in certain embodiments, the TOR kinase inhibitors do not include the compounds depicted below, namely:

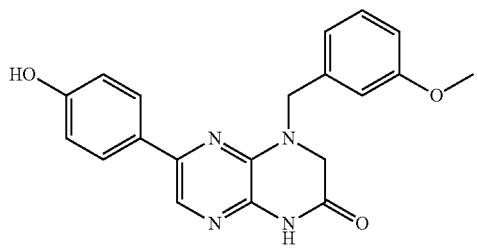 [SMILES: COc1cccc(CN2CC(=O)Nc3ncc(-c4ccc(O)cc4)nc32)c1]

6-(4-hydroxyphenyl)-4-(3-methoxybenzyl)-3,4-dihydropyrazino[2,3-b]pyrazin-2(1H)-one;

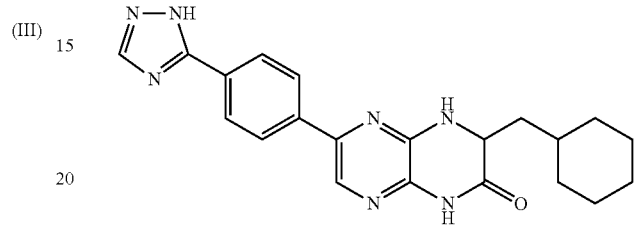

6-(4-(1H-1,2,4-triazol-5-yl)phenyl)-3-(cyclohexylmethyl)-3,4-dihydropyrazino[2,3-b]pyrazin-2(1H)-one; or

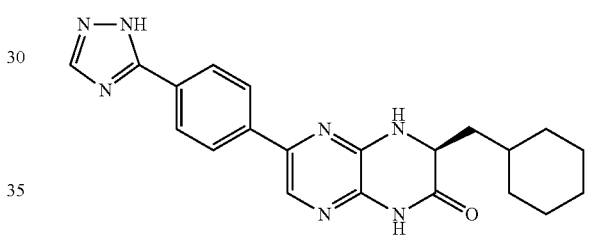

(R)-6-(4-(1H-1,2,4-triazol-5-yl)phenyl)-3-(cyclohexylmethyl)-3,4-dihydropyrazino[2,3-b]pyrazin-2(1H)-one.

In some embodiments of compounds of formula (III), $R^1$ is substituted or unsubstituted aryl or substituted or unsubstituted heteroaryl. In one embodiment, $R^1$ is phenyl, pyridyl, pyrimidyl, benzimidazolyl, indolyl, indazolyl, 1H-pyrrolo[2,3-b]pyridyl, 1H-imidazo[4,5-b]pyridyl, 1H-imidazo[4,5-b]pyridin-2(3H)-onyl, 3H-imidazo[4,5-b]pyridyl, or pyrazolyl, each optionally substituted. In some embodiments, $R^1$ is phenyl substituted with one or more substituents independently selected from the group consisting of substituted or unsubstituted $C_{1-8}$ alkyl (for example, methyl), substituted or unsubstituted heterocyclyl (for example, substituted or unsubstituted triazolyl or pyrazolyl), halogen (for example, fluorine), aminocarbonyl, cyano, hydroxyalkyl (for example, hydroxypropyl), and hydroxy. In other embodiments, $R^1$ is pyridyl substituted with one or more substituents independently selected from the group consisting of substituted or unsubstituted $C_{1-8}$ alkyl, substituted or unsubstituted heterocyclyl (for example, substituted or unsubstituted triazolyl), halogen, aminocarbonyl, cyano, hydroxyalkyl, —OR, and —$NR_2$, wherein each R is independently H, or a substituted or unsubstituted $C_{1-4}$ alkyl. In yet other embodiments, $R^1$ is 1H-pyrrolo[2,3-b]pyridyl or benzimidazolyl, each optionally substituted with one or more substituents independently selected from the group consisting of substituted or unsubstituted $C_{1-8}$ alkyl, and —$NR_2$, wherein each R is independently H, or a substituted or unsubstituted $C_{1-4}$ alkyl.

In some embodiments of compounds of formula (III), R¹ is

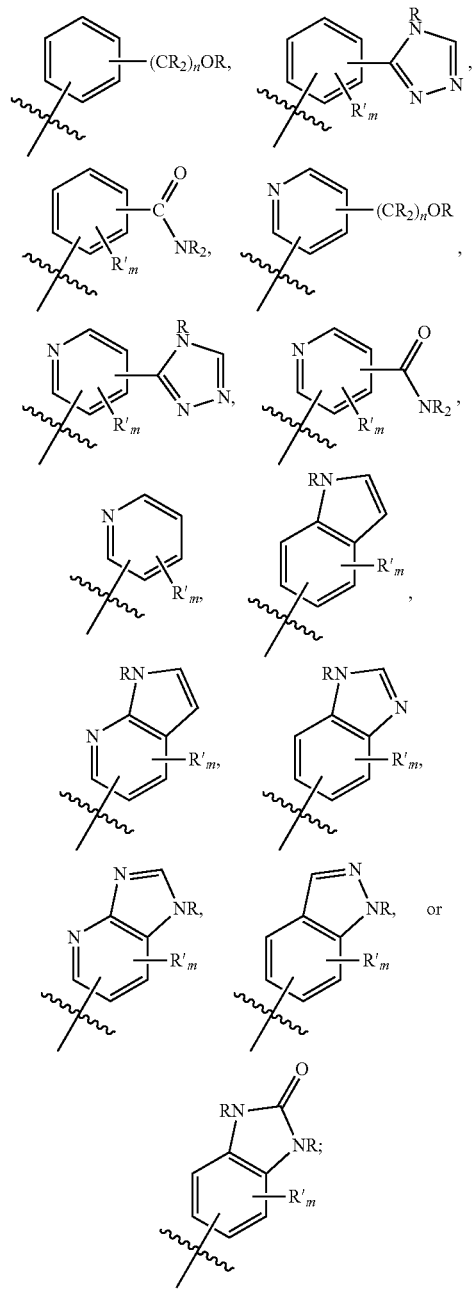

wherein R is at each occurrence independently H, or a substituted or unsubstituted $C_{1-4}$ alkyl (for example, methyl); R' is at each occurrence independently a substituted or unsubstituted $C_{1-4}$ alkyl, halogen (for example, fluorine), cyano, —OR, or —NR₂; m is 0-3; and n is 0-3. It will be understood by those skilled in the art that any of the substituents R' may be attached to any suitable atom of any of the rings in the fused ring systems. It will also be understood by those skilled in the art that the connecting bond of R¹ (designated by the bisecting wavy line) may be attached to any of the atoms in any of the rings in the fused ring systems.

In some embodiments of compounds of formula (III), R¹ is

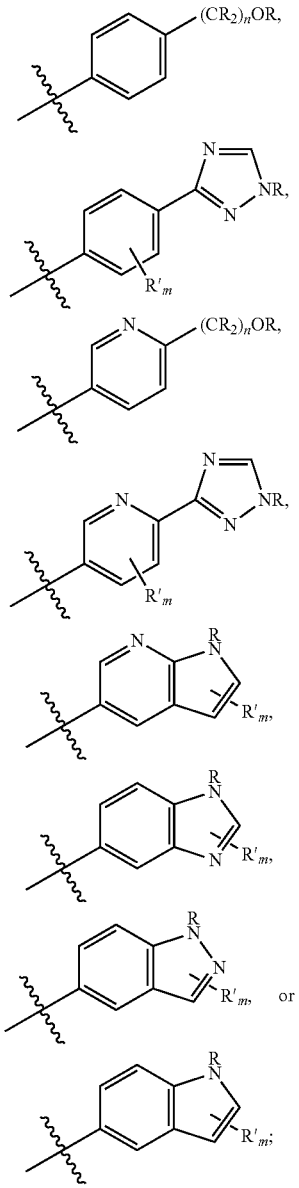

wherein R is at each occurrence independently H, or a substituted or unsubstituted $C_{1-4}$ alkyl; R' is at each occurrence independently a substituted or unsubstituted $C_{1-4}$ alkyl, halogen, cyano, —OR, or —NR₂; m is 0-3; and n is 0-3.

In some embodiments of compounds of formula (III), R² is H, substituted or unsubstituted $C_{1-8}$ alkyl, substituted or unsubstituted cycloalkyl, substituted or unsubstituted heterocyclyl, substituted or unsubstituted $C_{1-4}$ alkyl-heterocyclyl, substituted or unsubstituted $C_{1-4}$ alkyl-aryl, or substituted or unsubstituted $C_{1-4}$ alkyl-cycloalkyl. For example, R² is H, methyl, ethyl, n-propyl, isopropyl, n-butyl, sec-butyl, isobutyl, tert-butyl, n-pentyl, isopentyl, cyclopentyl, cyclohexyl, tetrahydrofuranyl, tetrahydropyranyl, ($C_{1-4}$ alkyl)-phenyl, ($C_{1-4}$ alkyl)-cyclopropyl, ($C_{1-4}$ alkyl)-cyclobutyl, ($C_{1-4}$ alkyl)-cyclopentyl, ($C_{1-4}$ alkyl)-cyclohexyl, ($C_{1-4}$ alkyl)-pyrrolidyl, ($C_{1-4}$ alkyl)-piperidyl, ($C_{1-4}$ alkyl)- piperazinyl, (C$_{1-4}$ alkyl)-morpholinyl, (C$_{1-4}$ alkyl)-tetrahydrofuranyl, or (C$_{1-4}$ alkyl)-tetrahydropyranyl, each optionally substituted.

In other embodiments, R$^2$ is H, C$_{1-4}$ alkyl, (C$_{1-4}$alkyl)(OR),

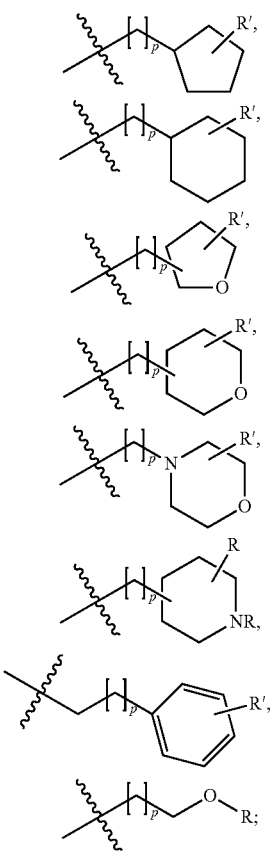

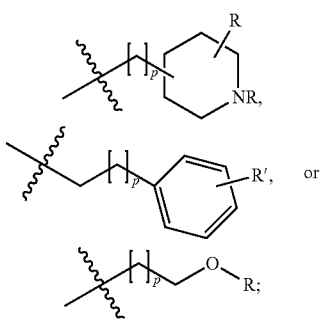

wherein R is at each occurrence independently H, or a substituted or unsubstituted C$_{1-4}$ alkyl (for example, methyl); R' is at each occurrence independently H, —OR, cyano, or a substituted or unsubstituted C$_{1-4}$ alkyl (for example, methyl); and p is 0-3.

In some such embodiments, R$^2$ is H, C$_{1-4}$ alkyl, (C$_{1-4}$alkyl)(OR),

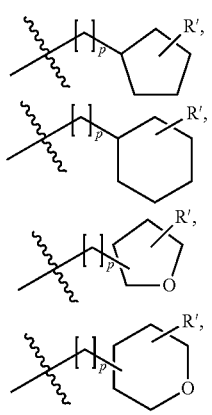

wherein R is at each occurrence independently H, or a substituted or unsubstituted C$_{1-2}$ alkyl; R' is at each occurrence independently H, —OR, cyano, or a substituted or unsubstituted C$_{1-2}$ alkyl; and p is 0-1.

In some other embodiments of compounds of formula (III), R$^2$ and one of R$^3$ and R$^4$ together with the atoms to which they are attached form a substituted or unsubstituted heterocyclyl. For example, in some embodiments, the compound of formula (III) is

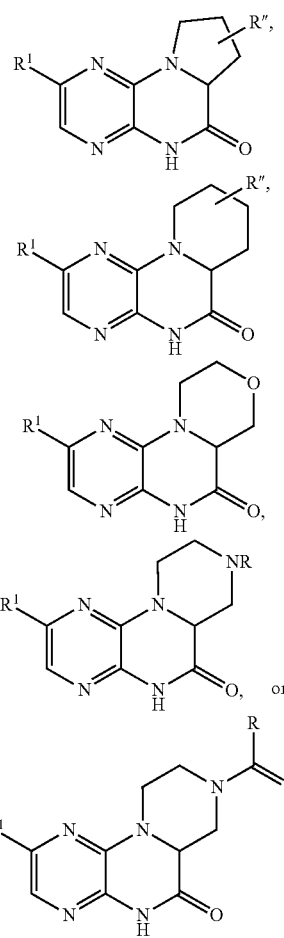

wherein R is at each occurrence independently H, or a substituted or unsubstituted $C_{1-4}$ alkyl; R" is H, OR, or a substituted or unsubstituted $C_{1-4}$ alkyl; and $R^1$ is as defined herein.

In some embodiments of compounds of formula (III), $R^3$ and $R^4$ are both H. In others, one of $R^3$ and $R^4$ is H and the other is other than H. In still others, one of $R^3$ and $R^4$ is $C_{1-4}$ alkyl (for example, methyl) and the other is H. In still others, both of $R^3$ and $R^4$ are $C_{1-4}$ alkyl (for example, methyl).

In some such embodiments described above, $R^1$ is substituted or unsubstituted aryl, or substituted or unsubstituted heteroaryl. For example, $R^1$ is phenyl, pyridyl, pyrimidyl, benzimidazolyl, indolyl, indazolyl, 1H-pyrrolo[2,3-b] pyridyl, 1H-imidazo[4,5-b]pyridyl, 1H-imidazo[4,5-b]pyridin-2(3H)-onyl, 3H-imidazo[4,5-b]pyridyl, or pyrazolyl, each optionally substituted. In some embodiments, $R^1$ is phenyl substituted with one or more substituents independently selected from the group consisting of substituted or unsubstituted $C_{1-8}$ alkyl, substituted or unsubstituted heterocyclyl, halogen, aminocarbonyl, cyano, hydroxyalkyl and hydroxy. In others, $R^1$ is pyridyl substituted with one or more substituents independently selected from the group consisting of cyano, substituted or unsubstituted $C_{1-8}$ alkyl, substituted or unsubstituted heterocyclyl, hydroxyalkyl, halogen, aminocarbonyl, —OR, and —$NR_2$, wherein each R is independently H, or a substituted or unsubstituted $C_{1-4}$ alkyl. In others, $R^1$ is 1H-pyrrolo[2,3-b]pyridyl or benzimidazolyl, optionally substituted with one or more substituents independently selected from the group consisting of substituted or unsubstituted $C_{1-8}$ alkyl, and —$NR_2$, wherein R is independently H, or a substituted or unsubstituted $C_{1-4}$ alkyl In certain embodiments, the compounds of formula (III) have an $R^1$ group set forth herein and an $R^2$ group set forth herein.

In some embodiments of compounds of formula (III), the compound at a concentration of 10 μM inhibits mTOR, DNA-PK, or PI3K or a combination thereof, by at least about 50%. Compounds of formula (III) may be shown to be inhibitors of the kinases above in any suitable assay system.

Representative TOR kinase inhibitors of formula (III) include compounds from Table C.

TABLE C 6-(1H-pyrrolo[2,3-b]pyridin-3-yl)-4-(2-(tetrahydro-2H-pyran-4-yl)ethyl)-3,4-dihydropyrazino[2,3-b]pyrazin-2(1H)-one;
6-(4-methyl-6-(1H-1,2,4-triazol-3-yl)pyridin-3-yl)-4-((tetrahydro-2H-pyran-4-yl)methyl)-3,4-dihydropyrazino[2,3-b]pyrazin-2(1H)-one;
6-(5-fluoro-2-methyl-4-(1H-1,2,4-triazol-3-yl)phenyl)-4-((trans-4-methoxycyclohexyl)methyl)-3,4-dihydropyrazino[2,3-b]pyrazin-2(1H)-one;
6-(5-fluoro-2-methyl-4-(1H-1,2,4-triazol-3-yl)phenyl)-4-((cis-4-methoxycyclohexyl)methyl)-3,4-dihydropyrazino[2,3-b]pyrazin-2(1H)-one;
6-(6-(1H-1,2,4-triazol-3-yl)pyridin-3-yl)-4-((trans-4-methoxycyclohexyl)methyl)-3,4-dihydropyrazino[2,3-b]pyrazin-2(1H)-one;
6-(5-fluoro-2-methyl-4-(1H-1,2,4-triazol-3-yl)phenyl)-4-((trans-4-hydroxycyclohexyl)methyl)-3,4-dihydropyrazino[2,3-b]pyrazin-2(1H)-one;
6-(6-(1H-1,2,4-triazol-3-yl)pyridin-3-yl)-4-((cis-4-methoxycyclohexyl)methyl)-3,4-dihydropyrazino[2,3-b]pyrazin-2(1H)-one;
6-(6-(1H-1,2,4-triazol-3-yl)pyridin-3-yl)-4-((trans-4-hydroxycyclohexyl)methyl)-3,4-dihydropyrazino[2,3-b]pyrazin-2(1H)-one;
6-(6-(1H-1,2,4-triazol-3-yl)pyridin-3-yl)-4-(cis-4-hydroxycyclohexyl)-3,4-dihydropyrazino[2,3-b]pyrazin-2(1H)-one;
6-(6-(1H-1,2,4-triazol-3-yl)pyridin-3-yl)-4-((cis-4-hydroxycyclohexyl)methyl)-3,4-dihydropyrazino[2,3-b]pyrazin-2(1H)-one;
6-(5-fluoro-2-methyl-4-(1H-1,2,4-triazol-3-yl)phenyl)-4-(trans-4-methoxycyclohexyl)-3,4-dihydropyrazino[2,3-b]pyrazin-2(1H)-one;
6-(6-(1H-1,2,4-triazol-3-yl)pyridin-3-yl)-4-(trans-4-methoxycyclohexyl)-3,4-dihydropyrazino[2,3-b]pyrazin-2(1H)-one;
6-(6-(1H-1,2,4-triazol-3-yl)pyridin-3-yl)-4-(trans-4-hydroxycyclohexyl)-3,4-dihydropyrazino[2,3-b]pyrazin-2(1H)-one;
6-(5-fluoro-2-methyl-4-(1H-1,2,4-triazol-3-yl)phenyl)-4-((cis-4-hydroxycyclohexyl)methyl)-3,4-dihydropyrazino[2,3-b]pyrazin-2(1H)-one;
6-(6-(1H-1,2,4-triazol-3-yl)pyridin-3-yl)-4-(cis-4-methoxycyclohexyl)-3,4-dihydropyrazino[2,3-b]pyrazin-2(1H)-one;
6-(6-(1H-1,2,4-triazol-3-yl)pyridin-3-yl)-4-(2-methoxyethyl)-3,4-dihydropyrazino[2,3-b]pyrazin-2(1H)-one;
6-(6-(1H-1,2,4-triazol-3-yl)pyridin-3-yl)-4-isopropyl-3,4-dihydropyrazino[2,3-b]pyrazin-2(1H)-one;
6-(5-fluoro-2-methyl-4-(1H-1,2,4-triazol-3-yl)phenyl)-4-(cis-4-hydroxycyclohexyl)-3,4-dihydropyrazino[2,3-b]pyrazin-2(1H)-one;
6-(5-fluoro-2-methyl-4-(1H-1,2,4-triazol-3-yl)phenyl)-4-(cis-4-methoxycyclohexyl)-3,4-dihydropyrazino[2,3-b]pyrazin-2(1H)-one;
6-(5-fluoro-2-methyl-4-(1H-1,2,4-triazol-3-yl)phenyl)-4-(2-methoxyethyl)-3,4-dihydropyrazino[2,3-b]pyrazin-2(1H)-one;
6-(6-(1H-1,2,4-triazol-3-yl)pyridin-3-yl)-4-(tetrahydro-2H-pyran-4-yl)-3,4-dihydropyrazino[2,3-b]pyrazin-2(1H)-one;
6-(6-(1H-1,2,4-triazol-3-yl)pyridin-3-yl)-4-ethyl-3,4-dihydropyrazino[2,3-b]pyrazin-2(1H)-one;
6-(5-fluoro-2-methyl-4-(1H-1,2,4-triazol-3-yl)phenyl)-4-(trans-4-hydroxycyclohexyl)-3,4-dihydropyrazino[2,3-b]pyrazin-2(1H)-one;
6-(5-fluoro-2-methyl-4-(1H-1,2,4-triazol-3-yl)phenyl)-4-(tetrahydro-2H-pyran-4-yl)-3,4-dihydropyrazino[2,3-b]pyrazin-2(1H)-one;
6-(5-fluoro-2-methyl-4-(1H-1,2,4-triazol-3-yl)phenyl)-4-isopropyl-3,4-dihydropyrazino[2,3-b]pyrazin-2(1H)-one;
4-ethyl-6-(5-fluoro-2-methyl-4-(1H-1,2,4-triazol-3-yl)phenyl)-3,4-dihydropyrazino[2,3-b]pyrazin-2(1H)-one;
6-(3-fluoro-2-methyl-4-(1H-1,2,4-triazol-3-yl)phenyl)-4-(tetrahydro-2H-pyran-4-yl)-3,4-dihydropyrazino[2,3-b]pyrazin-2(1H)-one;

TABLE C-continued 6-(3-fluoro-2-methyl-4-(1H-1,2,4-triazol-3-yl)phenyl)-4-(cis-4-methoxycyclohexyl)-3,4-dihydropyrazino[2,3-b]pyrazin-2(1H)-one;
6-(3-fluoro-2-methyl-4-(1H-1,2,4-triazol-3-yl)phenyl)-4-(trans-4-methoxycyclohexyl)-3,4-dihydropyrazino[2,3-b]pyrazin-2(1H)-one;
4-(2-methoxyethyl)-6-(4-methyl-6-(1H-1,2,4-triazol-3-yl)pyridin-3-yl)-3,4-dihydropyrazino[2,3-b]pyrazin-2(1H)-one;
6-(3-(1H-1,2,4-triazol-5-yl)phenyl)-4-(2-(tetrahydro-2H-pyran-4-yl)ethyl)-3,4-dihydropyrazino[2,3-b]pyrazin-2(1H)-one;
5-(8-(2-methoxyethyl)-6-oxo-5,6,7,8-tetrahydropyrazino[2,3-b]pyrazin-2-yl)-4-methylpicolinamide;
3-(6-oxo-8-(2-(tetrahydro-2H-pyran-4-yl)ethyl)-5,6,7,8-tetrahydropyrazino[2,3-b]pyrazin-2-yl)benzamide;
3-(6-oxo-8-(2-(tetrahydro-2H-pyran-4-yl)ethyl)-5,6,7,8-tetrahydropyrazino[2,3-b]pyrazin-2-yl)benzonitrile;
5-(8-(trans-4-methoxycyclohexyl)-6-oxo-5,6,7,8-tetrahydropyrazino[2,3-b]pyrazin-2-yl)-4-methylpicolinamide;
6-(1H-imidazo[4,5-b]pyridin-6-yl)-4-(2-(tetrahydro-2H-pyran-4-yl)ethyl)-3,4-dihydropyrazino[2,3-b]pyrazin-2(1H)-one;
6-(1H-indazol-6-yl)-4-(2-(tetrahydro-2H-pyran-4-yl)ethyl)-3,4-dihydropyrazino[2,3-b]pyrazin-2(1H)-one;
4-((1R,3S)-3-methoxycyclopentyl)-6-(2-methyl-6-(4H-1,2,4-triazol-3-yl)pyridin-3-yl)-3,4-dihydropyrazino[2,3-b]pyrazin-2(1H)-one;
4-((1S,3R)-3-methoxycyclopentyl)-6-(2-methyl-6-(4H-1,2,4-triazol-3-yl)pyridin-3-yl)-3,4-dihydropyrazino[2,3-b]pyrazin-2(1H)-one;
4-((1R,3R)-3-methoxycyclopentyl)-6-(2-methyl-6-(4H-1,2,4-triazol-3-yl)pyridin-3-yl)-3,4-dihydropyrazino[2,3-b]pyrazin-2(1H)-one;
4-((1S,3S)-3-methoxycyclopentyl)-6-(2-methyl-6-(4H-1,2,4-triazol-3-yl)pyridin-3-yl)-3,4-dihydropyrazino[2,3-b]pyrazin-2(1H)-one;
4-ethyl-6-(2-methyl-6-(4H-1,2,4-triazol-3-yl)pyridin-3-yl)-3,4-dihydropyrazino[2,3-b]pyrazin-2(1H)-one;
6-(1H-pyrrolo[2,3-b]pyridin-5-yl)-4-(2-(tetrahydro-2H-pyran-4-yl)ethyl)-3,4-dihydropyrazino[2,3-b]pyrazin-2(1H)-one;
6-(1H-indol-6-yl)-4-(2-(tetrahydro-2H-pyran-4-yl)ethyl)-3,4-dihydropyrazino[2,3-b]pyrazin-2(1H)-one;
6-(1H-indol-5-yl)-4-(2-(tetrahydro-2H-pyran-4-yl)ethyl)-3,4-dihydropyrazino[2,3-b]pyrazin-2(1H)-one;
4-(((1R,3S)-3-methoxycyclopentyl)methyl)-6-(2-methyl-6-(4H-1,2,4-triazol-3-yl)pyridin-3-yl)-3,4-dihydropyrazino[2,3-b]pyrazin-2(1H)-one;
4-(((1S,3R)-3-methoxycyclopentyl)methyl)-6-(2-methyl-6-(4H-1,2,4-triazol-3-yl)pyridin-3-yl)-3,4-dihydropyrazino[2,3-b]pyrazin-2(1H)-one;
6-(3-fluoro-2-methyl-4-(4H-1,2,4-triazol-3-yl)phenyl)-4-(2-(tetrahydro-2H-pyran-4-yl)ethyl)-3,4-dihydropyrazino[2,3-b]pyrazin-2(1H)-one;
6-(3-fluoro-2-methyl-4-(4H-1,2,4-triazol-3-yl)phenyl)-4-(2-methoxyethyl)-3,4-dihydropyrazino[2,3-b]pyrazin-2(1H)-one;
3,3-dimethyl-6-(4-methyl-6-(4H-1,2,4-triazol-3-yl)pyridin-3-yl)-4-((tetrahydro-2H-pyran-4-yl)methyl)-3,4-dihydropyrazino[2,3-b]pyrazin-2(1H)-one;
6-(6-(2-hydroxypropan-2-yl)pyridin-3-yl)-4-((1R,3S)-3-methoxycyclopentyl)-3,4-dihydropyrazino[2,3-b]pyrazin-2(1H)-one;
6-(6-(2-hydroxypropan-2-yl)pyridin-3-yl)-4-((1S,3R)-3-methoxycyclopentyl)-3,4-dihydropyrazino[2,3-b]pyrazin-2(1H)-one;
6-(6-(2-hydroxypropan-2-yl)pyridin-3-yl)-4-(((1S,3S)-3-methoxycyclopentyl)methyl)-3,4-dihydropyrazino[2,3-b]pyrazin-2(1H)-one;
6-(6-(2-hydroxypropan-2-yl)pyridin-3-yl)-4-(((1R,3R)-3-methoxycyclopentyl)methyl)-3,4-dihydropyrazino[2,3-b]pyrazin-2(1H)-one;
6-(6-(2-hydroxypropan-2-yl)pyridin-3-yl)-4-((1S,3S)-3-methoxycyclopentyl)-3,4-dihydropyrazino[2,3-b]pyrazin-2(1H)-one;
6-(6-(2-hydroxypropan-2-yl)pyridin-3-yl)-4-((1R,3R)-3-methoxycyclopentyl)-3,4-dihydropyrazino[2,3-b]pyrazin-2(1H)-one;
6-(6-(2-hydroxypropan-2-yl)pyridin-3-yl)-4-(((1R,3S)-3-methoxycyclopentyl)methyl)-3,4-dihydropyrazino[2,3-b]pyrazin-2(1H)-one;
6-(6-(2-hydroxypropan-2-yl)pyridin-3-yl)-4-(((1S,3R)-3-methoxycyclopentyl)methyl)-3,4-dihydropyrazino[2,3-b]pyrazin-2(1H)-one;
6-(3-fluoro-4-(4H-1,2,4-triazol-3-yl)phenyl)-4-(2-methoxyethyl)-3,4-dihydropyrazino[2,3-b]pyrazin-2(1H)-one;
6-(3-fluoro-4-(4H-1,2,4-triazol-3-yl)phenyl)-4-(2-(tetrahydro-2H-pyran-4-yl)ethyl)-3,4-dihydropyrazino[2,3-b]pyrazin-2(1H)-one;
7'-(2-methyl-4-(4H-1,2,4-triazol-3-yl)phenyl)-1'-((tetrahydro-2H-pyran-4-yl)methyl)-1'H-spiro[cyclopentane-1,2'-pyrazino[2,3-b]pyrazin]-3'(4'H)-one;
7'-(2-methyl-4-(4H-1,2,4-triazol-3-yl)phenyl)-1'-((tetrahydro-2H-pyran-4-yl)methyl)-1'H-spiro[cyclobutane-1,2'-pyrazino[2,3-b]pyrazin]-3'(4'H)-one;
4-(cyclopropylmethyl)-6-(6-(2-hydroxypropan-2-yl)pyridin-3-yl)-3,4-dihydropyrazino[2,3-b]pyrazin-2(1H)-one;
7'-(2-methyl-4-(4H-1,2,4-triazol-3-yl)phenyl)-1'H-spiro[cyclopentane-1,2'-pyrazino[2,3-b]pyrazin]-3'(4'H)-one;
7'-(2-methyl-4-(4H-1,2,4-triazol-3-yl)phenyl)-1'H-spiro[cyclobutane-1,2'-pyrazino[2,3-b]pyrazin]-3'(4'H)-one;
7'-(2-methyl-4-(4H-1,2,4-triazol-3-yl)phenyl)-1'H-spiro[cyclopropane-1,2'-pyrazino[2,3-b]pyrazin]-3'(4'H)-one;
(R)-6-(4-(4H-1,2,4-triazol-3-yl)phenyl)-4-((tetrahydrofuran-2-yl)methyl)-3,4-dihydropyrazino[2,3-b]pyrazin-2(1H)-one;

TABLE C-continued (S)-6-(4-(4H-1,2,4-triazol-3-yl)phenyl)-4-((tetrahydrofuran-2-yl)methyl)-3,4-dihydropyrazino[2,3-b]pyrazin-2(1H)-one;
6-(1H-indazol-5-yl)-4-(2-(tetrahydro-2H-pyran-4-yl)ethyl)-3,4-dihydropyrazino[2,3-b]pyrazin-2(1H)-one;
4-(6-oxo-8-(2-(tetrahydro-2H-pyran-4-yl)ethyl)-5,6,7,8-tetrahydropyrazino[2,3-b]pyrazin-2-yl)benzamide;
4-(2-methoxyethyl)-3,3-dimethyl-6-(2-methyl-4-(4H-1,2,4-triazol-3-yl)phenyl)-3,4-dihydropyrazino[2,3-b]pyrazin-2(1H)-one;
4-ethyl-3,3-dimethyl-6-(2-methyl-4-(4H-1,2,4-triazol-3-yl)phenyl)-3,4-dihydropyrazino[2,3-b]pyrazin-2(1H)-one;
6-(2-methyl-4-(4H-1,2,4-triazol-3-yl)phenyl)-3,4-dihydropyrazino[2,3-b]pyrazin-2(1H)-one;
3,3-dimethyl-6-(2-methyl-6-(4H-1,2,4-triazol-3-yl)pyridin-3-yl)-4-((tetrahydro-2H-pyran-4-yl)methyl)-3,4-dihydropyrazino[2,3-b]pyrazin-2(1H)-one;
(R)-6-(6-(1-hydroxyethyl)pyridin-3-yl)-4-(2-(tetrahydro-2H-pyran-4-yl)ethyl)-3,4-dihydropyrazino[2,3-b]pyrazin-2(1H)-one;
3,3-dimethyl-6-(2-methyl-4-(4H-1,2,4-triazol-3-yl)phenyl)-4-((tetrahydro-2H-pyran-4-yl)methyl)-3,4-dihydropyrazino[2,3-b]pyrazin-2(1H)-one;
6-(6-(2-hydroxypropan-2-yl)-4-methylpyridin-3-yl)-4-(trans-4-methoxycyclohexyl)-3,4-dihydropyrazino[2,3-b]pyrazin-2(1H)-one;
6-(6-(2-hydroxypropan-2-yl)-4-methylpyridin-3-yl)-4-((tetrahydro-2H-pyran-4-yl)methyl)-3,4-dihydropyrazino[2,3-b]pyrazin-2(1H)-one;
3,3-dimethyl-6-(2-methyl-4-(4H-1,2,4-triazol-3-yl)phenyl)-3,4-dihydropyrazino[2,3-b]pyrazin-2(1H)-one;
3,3-dimethyl-6-(2-methyl-6-(4H-1,2,4-triazol-3-yl)pyridin-3-yl)-4-(2-(tetrahydro-2H-pyran-4-yl)ethyl)-3,4-dihydropyrazino[2,3-b]pyrazin-2(1H)-one;
6-(6-(2-hydroxypropan-2-yl)-2-methylpyridin-3-yl)-4-((tetrahydro-2H-pyran-4-yl)methyl)-3,4-dihydropyrazino[2,3-b]pyrazin-2(1H)-one;
6-(6-(2-hydroxypropan-2-yl)-2-methylpyridin-3-yl)-4-(trans-4-methoxycyclohexyl)-3,4-dihydropyrazino[2,3-b]pyrazin-2(1H)-one;
(S)-6-(6-(1-hydroxyethyl)pyridin-3-yl)-4-(2-(tetrahydro-2H-pyran-4-yl)ethyl)-3,4-dihydropyrazino[2,3-b]pyrazin-2(1H)-one;
3,3-dimethyl-6-(2-methyl-4-(4H-1,2,4-triazol-3-yl)phenyl)-4-(2-(tetrahydro-2H-pyran-4-yl)ethyl)-3,4-dihydropyrazino[2,3-b]pyrazin-2(1H)-one;
6-(6-(2-hydroxypropan-2-yl)pyridin-3-yl)-3,3-dimethyl-4-(2-(tetrahydro-2H-pyran-4-yl)ethyl)-3,4-dihydropyrazino[2,3-b]pyrazin-2(1H)-one;
6-(4-(2-hydroxypropan-2-yl)phenyl)-4-(trans-4-methoxycyclohexyl)-3,4-dihydropyrazino[2,3-b]pyrazin-2(1H)-one;
6-(4-(2-hydroxypropan-2-yl)phenyl)-4-((trans-4-methoxycyclohexyl)methyl)-3,4-dihydropyrazino[2,3-b]pyrazin-2(1H)-one;
4-(cis-4-methoxycyclohexyl)-6-(2-methyl-6-(4H-1,2,4-triazol-3-yl)pyridin-3-yl)-3,4-dihydropyrazino[2,3-b]pyrazin-2(1H)-one;
4-(trans-4-methoxycyclohexyl)-6-(2-methyl-6-(4H-1,2,4-triazol-3-yl)pyridin-3-yl)-3,4-dihydropyrazino[2,3-b]pyrazin-2(1H)-one;
6-(4-(2-hydroxypropan-2-yl)phenyl)-4-((tetrahydro-2H-pyran-4-yl)methyl)-3,4-dihydropyrazino[2,3-b]pyrazin-2(1H)-one;
4-(2-methoxyethyl)-6-(2-methyl-6-(4H-1,2,4-triazol-3-yl)pyridin-3-yl)-3,4-dihydropyrazino[2,3-b]pyrazin-2(1H)-one;
9-(6-(4H-1,2,4-triazol-3-yl)-3-pyridyl)-6,11,4a-trihydromorpholino[4,3-e]pyrazino[2,3-b]pyrazin-5-one;
6-(2-methyl-6-(4H-1,2,4-triazol-3-yl)pyridin-3-yl)-4-((tetrahydro-2H-pyran-4-yl)methyl)-3,4-dihydropyrazino[2,3-b]pyrazin-2(1H)-one;
5-(8-(cis-4-methoxycyclohexyl)-6-oxo-5,6,7,8-tetrahydropyrazino[2,3-b]pyrazin-2-yl)-6-methylpicolinonitrile;
6-(6-(4H-1,2,4-triazol-3-yl)pyridin-3-yl)-4-(2-(tetrahydro-2H-pyran-4-yl)ethyl)-3,4-dihydropyrazino[2,3-b]pyrazin-2(1H)-one;
9-(4-(4H-1,2,4-triazol-3-yl)-2-methylphenyl)-3-(2-methoxyacetyl)-6,11,4a-trihydropiperazino[1,2-e]pyrazino[2,3-b]pyrazin-5-one;
9-(4-(4H-1,2,4-triazol-3-yl)-2-methylphenyl)-6,11,4a-trihydropiperazino[1,2-e]pyrazino[2,3-b]pyrazin-5-one;
9-(4-(4H-1,2,4-triazol-3-yl)-2-methylphenyl)-3-(2-methoxyethyl)-6,11,4a-trihydropiperazino[1,2-e]pyrazino[2,3-b]pyrazin-5-one;
4-(cyclopentylmethyl)-6-(2-methyl-6-(4H-1,2,4-triazol-3-yl)pyridin-3-yl)-3,4-dihydropyrazino[2,3-b]pyrazin-2(1H)-one;
9-(6-(4H-1,2,4-triazol-3-yl)-2-methyl-3-pyridyl)-6,11,4a-trihydromorpholino[4,3-e]pyrazino[2,3-b]pyrazin-5-one;
4-(trans-4-hydroxycyclohexyl)-6-(6-(2-hydroxypropan-2-yl)pyridin-3-yl)-3,4-dihydropyrazino[2,3-b]pyrazin-2(1H)-one;
4-(cis-4-hydroxycyclohexyl)-6-(6-(2-hydroxypropan-2-yl)pyridin-3-yl)-3,4-dihydropyrazino[2,3-b]pyrazin-2(1H)-one;
6-(6-(2-hydroxypropan-2-yl)pyridin-3-yl)-4-((tetrahydrofuran-3-yl)methyl)-3,4-dihydropyrazino[2,3-b]pyrazin-2(1H)-one;
4-(cyclopentylmethyl)-6-(6-(2-hydroxypropan-2-yl)pyridin-3-yl)-3,4-dihydropyrazino[2,3-b]pyrazin-2(1H)-one;
6-(6-(2-hydroxypropan-2-yl)pyridin-3-yl)-4-neopentyl-3,4-dihydropyrazino[2,3-b]pyrazin-2(1H)-one;
6-(6-(2-hydroxypropan-2-yl)pyridin-3-yl)-4-isobutyl-3,4-dihydropyrazino[2,3-b]pyrazin-2(1H)-one;

TABLE C-continued 3-methyl-6-(2-methyl-4-(4H-1,2,4-triazol-3-yl)phenyl)-4-(2-(tetrahydro-2H-pyran-4-yl)ethyl)-3,4-dihydropyrazino[2,3-b]pyrazin-2(1H)-one;
6-(6-(2-hydroxypropan-2-yl)pyridin-3-yl)-4-(piperidin-4-yl)-3,4-dihydropyrazino[2,3-b]pyrazin-2(1H)-one;
6-(6-(2-hydroxypropan-2-yl)pyridin-3-yl)-4-(2-(tetrahydro-2H-pyran-3-yl)ethyl)-3,4-dihydropyrazino[2,3-b]pyrazin-2(1H)-one;
8-(4-(4H-1,2,4-triazol-3-yl)-2-methylphenyl)(3aS,2R)-2-methoxy-5,10,3a-trihydropyrazino[2,3-b]pyrrolidino[1,2-e]pyrazin-4-one;
8-(4-(4H-1,2,4-triazol-3-yl)-2-methylphenyl)(2R,3aR)-2-methoxy-5,10,3a-trihydropyrazino[2,3-b]pyrrolidino[1,2-e]pyrazin-4-one;
8-(4-(4H-1,2,4-triazol-3-yl)-2-methylphenyl)(2S,3aR)-2-methoxy-5,10,3a-trihydropyrazino[2,3-b]pyrrolidino[1,2-e]pyrazin-4-one;
8-(4-(4H-1,2,4-triazol-3-yl)-2-methylphenyl)(2S,3aS)-2-methoxy-5,10,3a-trihydropyrazino[2,3-b]pyrrolidino[1,2-e]pyrazin-4-one;
6-(6-(2-hydroxypropan-2-yl)pyridin-3-yl)-4-(3-methoxypropyl)-3,4-dihydropyrazino[2,3-b]pyrazin-2(1H)-one;
(S)-6-(6-(2-hydroxypropan-2-yl)pyridin-3-yl)-4-((tetrahydrofuran-2-yl)methyl)-3,4-dihydropyrazino[2,3-b]pyrazin-2(1H)-one;
(R)-6-(6-(2-hydroxypropan-2-yl)pyridin-3-yl)-4-((tetrahydrofuran-2-yl)methyl)-3,4-dihydropyrazino[2,3-b]pyrazin-2(1H)-one;
6-(2-methyl-6-(4H-1,2,4-triazol-3-yl)pyridin-3-yl)-4-(2-(tetrahydro-2H-pyran-4-yl)ethyl)-3,4-dihydropyrazino[2,3-b]pyrazin-2(1H)-one;
9-(4-(4H-1,2,4-triazol-3-yl)-2-methylphenyl)-3-methyl-6,11,4a-trihydropiperazino[1,2-e]pyrazino[2,3-b]pyrazin-5-one;
9-(4-(4H-1,2,4-triazol-3-yl)phenyl)-6,11,4a-trihydromorpholino[4,3-e]pyrazino[2,3-b]pyrazin-5-one;
9-(4-(4H-1,2,4-triazol-3-yl)-2-methylphenyl)-6,11,4a-trihydropiperidino[1,2-e]pyrazino[2,3-b]pyrazin-5-one;
6-(6-(2-hydroxypropan-2-yl)pyridin-3-yl)-4-(trans-4-methoxycyclohexyl)-3,4-dihydropyrazino[2,3-b]pyrazin-2(1H)-one;
6-(6-(2-hydroxypropan-2-yl)pyridin-3-yl)-4-(cis-4-methoxycyclohexyl)-3,4-dihydropyrazino[2,3-b]pyrazin-2(1H)-one;
6-(6-(2-hydroxypropan-2-yl)pyridin-3-yl)-4-(2-morpholinoethyl)-3,4-dihydropyrazino[2,3-b]pyrazin-2(1H)-one;
6-(6-(2-hydroxypropan-2-yl)pyridin-3-yl)-4-phenethyl-3,4-dihydropyrazino[2,3-b]pyrazin-2(1H)-one;
6-(6-(2-hydroxypropan-2-yl)pyridin-3-yl)-4-(tetrahydro-2H-pyran-4-yl)-3,4-dihydropyrazino[2,3-b]pyrazin-2(1H)-one;
4-(cyclohexylmethyl)-6-(6-(2-hydroxypropan-2-yl)pyridin-3-yl)-3,4-dihydropyrazino[2,3-b]pyrazin-2(1H)-one;
6-(6-(2-hydroxypropan-2-yl)pyridin-3-yl)-4-((trans-4-methoxycyclohexyl)methyl)-3,4-dihydropyrazino[2,3-b]pyrazin-2(1H)-one;
6-(6-(2-hydroxypropan-2-yl)pyridin-3-yl)-4-((cis-4-methoxycyclohexyl)methyl)-3,4-dihydropyrazino[2,3-b]pyrazin-2(1H)-one;
(R)-6-(6-(2-hydroxypropan-2-yl)pyridin-3-yl)-4-(tetrahydrofuran-3-yl)-3,4-dihydropyrazino[2,3-b]pyrazin-2(1H)-one;
(S)-6-(6-(2-hydroxypropan-2-yl)pyridin-3-yl)-4-(tetrahydrofuran-3-yl)-3,4-dihydropyrazino[2,3-b]pyrazin-2(1H)-one;
6-(6-(2-hydroxypropan-2-yl)pyridin-3-yl)-4-phenyl-3,4-dihydropyrazino[2,3-b]pyrazin-2(1H)-one;
(S)-6-(6-(2-hydroxypropan-2-yl)pyridin-3-yl)-3-methyl-4-(2-(tetrahydro-2H-pyran-4-yl)ethyl)-3,4-dihydropyrazino[2,3-b]pyrazin-2(1H)-one;
9-[6-(1-hydroxy-isopropyl)-3-pyridyl]-6,11,4a-trihydromorpholino[4,3-e]pyrazino[2,3-b]pyrazin-5-one;
6-(6-(2-hydroxypropan-2-yl)pyridin-3-yl)-4-((tetrahydro-2H-pyran-4-yl)methyl)-3,4-dihydropyrazino[2,3-b]pyrazin-2(1H)-one;
6-(6-(2-hydroxypropan-2-yl)pyridin-3-yl)-4-(2-methoxyethyl)-3,4-dihydropyrazino[2,3-b]pyrazin-2(1H)-one;
6-(2-amino-7-methyl-1H-benzo[d]imidazol-5-yl)-4-(3-(trifluoromethyl)benzyl)-3,4-dihydropyrazino[2,3-b]pyrazin-2(1H)-one;
6-(6-(2-hydroxypropan-2-yl)pyridin-3-yl)-4-(3-(trifluoromethyl)benzyl)-3,4-dihydropyrazino[2,3-b]pyrazin-2(1H)-one;
9-(4-(4H-1,2,4-triazol-3-yl)-2-methylphenyl)-6,11,4a-trihydromorpholino[4,3-e]pyrazino[2,3-b]pyrazin-5-one;
6-(4-methyl-2-(methylamino)-1H-benzo[d]imidazol-6-yl)-4-(2-(tetrahydro-2H-pyran-4-yl)ethyl)-3,4-dihydropyrazino[2,3-b]pyrazin-2(1H)-one;
8-(4-(4H-1,2,4-triazol-3-yl)-2-methylphenyl)-5,10,3a-trihydropyrazino[2,3-b]pyrrolidino[1,2-e]pyrazin-4-one;
6-(4-(4H-1,2,4-triazol-3-yl)phenyl)-4-ethyl-3,4-dihydropyrazino[2,3-b]pyrazin-2(1H)-one;
6-(4-(4H-1,2,4-triazol-3-yl)phenyl)-4-((tetrahydro-2H-pyran-4-yl)methyl)-3,4-dihydropyrazino[2,3-b]pyrazin-2(1H)-one;
6-(6-(2-hydroxypropan-2-yl)pyridin-3-yl)-4-(2-(tetrahydro-2H-pyran-4-yl)ethyl)-3,4-dihydropyrazino[2,3-b]pyrazin-2(1H)-one;
6-(4-(4H-1,2,4-triazol-3-yl)phenyl)-4-(2-methoxyethyl)-3,4-dihydropyrazino[2,3-b]pyrazin-2(1H)-one;
6-(4-(4H-1,2,4-triazol-3-yl)phenyl)-4-(3-(trifluoromethyl)benzyl)-3,4-dihydropyrazino[2,3-b]pyrazin-2(1H)-one;
6-(2-methyl-4-(4H-1,2,4-triazol-3-yl)phenyl)-4-(2-(tetrahydro-2H-pyran-4-yl)ethyl)-3,4-dihydropyrazino[2,3-b]pyrazin-2(1H)-one;
6-(4-methyl-1H-benzo[d]imidazol-6-yl)-4-(2-(tetrahydro-2H-pyran-4-yl)ethyl)-3,4-

TABLE C-continued dihydropyrazino[2,3-b]pyrazin-2(1H)-one;
6-(4-(2-hydroxypropan-2-yl)phenyl)-4-(2-(tetrahydro-2H-pyran-4-yl)ethyl)-3,4-dihydropyrazino[2,3-b]pyrazin-2(1H)-one; and
6-(4-(1H-1,2,4-triazol-5-yl)phenyl)-4-(2-(tetrahydro-2H-pyran-4-yl)ethyl)-3,4-dihydropyrazino[2,3-b]pyrazin-2(1H)-one,
and pharmaceutically acceptable salts, clathrates, solvates, stereoisomers, tautomers, and prodrugs thereof.

In one embodiment, the TOR kinase inhibitors include compounds having the following formula (IV):

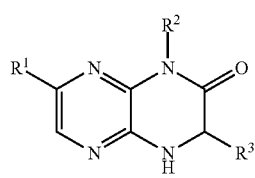

(IV)

and pharmaceutically acceptable salts, clathrates, solvates, stereoisomers, tautomers, and prodrugs thereof, wherein:

$R^1$ is substituted or unsubstituted $C_{1-8}$ alkyl, substituted or unsubstituted aryl, substituted or unsubstituted cycloalkyl, substituted or unsubstituted heterocyclyl, or substituted or unsubstituted heterocyclylalkyl;

$R^2$ is H, substituted or unsubstituted $C_{1-8}$ alkyl, substituted or unsubstituted cycloalkyl, substituted or unsubstituted heterocyclyl, substituted or unsubstituted heterocyclylalkyl, substituted or unsubstituted aralkyl, or substituted or unsubstituted cycloalkylalkyl;

$R^3$ is H, or a substituted or unsubstituted $C_{1-8}$ alkyl, wherein in certain embodiments, the TOR kinase inhibitors do not include 7-(4-hydroxyphenyl)-1-(3-methoxybenzyl)-3,4-dihydropyrazino[2,3-b]pyrazin-2(1H)-one, depicted below:

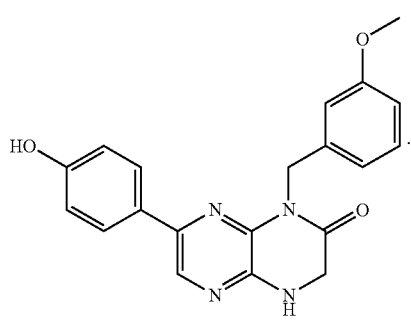 [SMILES: COc1cccc(CN2C(=O)CNc3ncc(-c4ccc(O)cc4)nc32)c1]

In some embodiments of compounds of formula (IV), $R^1$ is substituted or unsubstituted aryl or substituted or unsubstituted heteroaryl. For example, $R^1$ is phenyl, pyridyl, pyrimidyl, benzimidazolyl, 1H-pyrrolo[2,3-b]pyridyl, indazolyl, indolyl, 1H-imidazo[4,5-b]pyridyl, 1H-imidazo[4,5-b]pyridin-2(3H)-onyl, 3H-imidazo[4,5-b]pyridyl, or pyrazolyl, each optionally substituted. In some embodiments, $R^1$ is phenyl substituted with one or more substituents independently selected from the group consisting of substituted or unsubstituted $C_{1-8}$ alkyl (for example, methyl), substituted or unsubstituted heterocyclyl (for example, a substituted or unsubstituted triazolyl or pyrazolyl), aminocarbonyl, halogen (for example, fluorine), cyano, hydroxyalkyl and hydroxy. In other embodiments, $R^1$ is pyridyl substituted with one or more substituents independently selected from the group consisting of substituted or unsubstituted $C_{1-8}$ alkyl (for example, methyl), substituted or unsubstituted heterocyclyl (for example, a substituted or unsubstituted triazolyl), halogen, aminocarbonyl, cyano, hydroxyalkyl (for example, hydroxypropyl), —OR, and —$NR_2$, wherein each R is independently H, or a substituted or unsubstituted $C_{1-4}$ alkyl. In some embodiments, $R^1$ is 1H-pyrrolo[2,3-b]pyridyl or benzimidazolyl, optionally substituted with one or more substituents independently selected from the group consisting of substituted or unsubstituted $C_{1-8}$ alkyl, and —$NR_2$, wherein R is independently H, or a substituted or unsubstituted $C_{1-4}$ alkyl.

In some embodiments, $R^1$ is

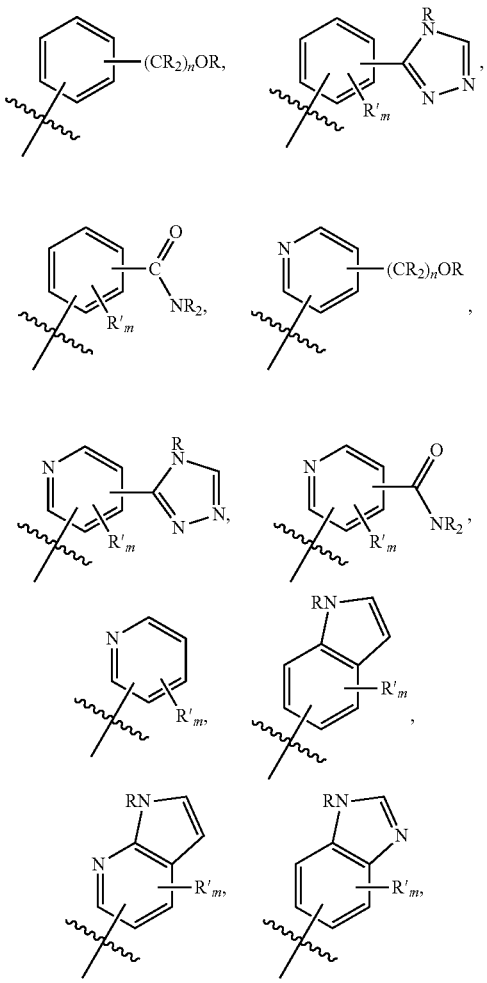

-continued

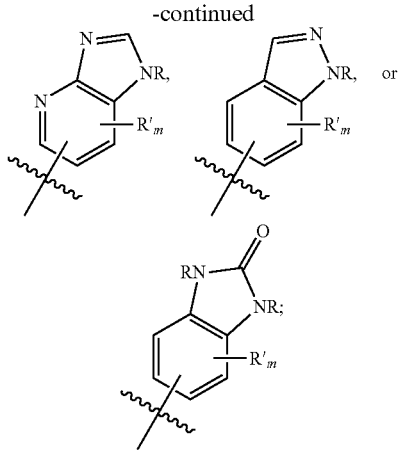

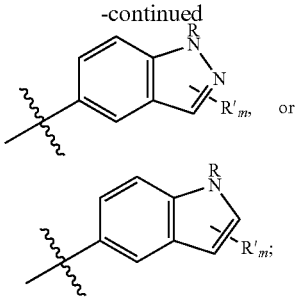

wherein R is at each occurrence independently H, or a substituted or unsubstituted $C_{1-4}$ alkyl (for example, methyl); R' is at each occurrence independently a substituted or unsubstituted $C_{1-4}$ alkyl (for example, methyl), halogen (for example, fluoro), cyano, —OR, or —NR$_2$; m is 0-3; and n is 0-3. It will be understood by those skilled in the art that any of the substituents R' may be attached to any suitable atom of any of the rings in the fused ring systems.

In some embodiments of compounds of formula (IV), $R^1$ is

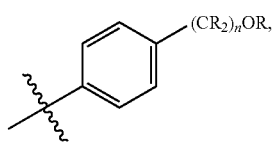

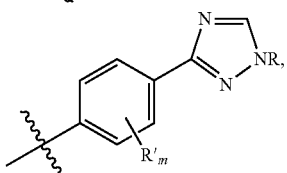

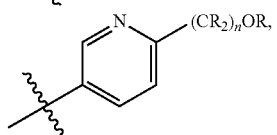

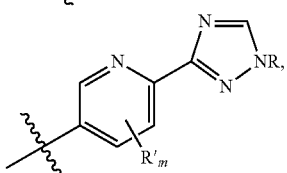

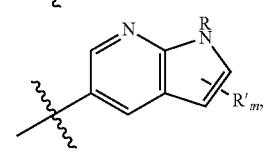

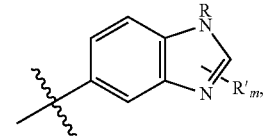

wherein R is at each occurrence independently H, or a substituted or unsubstituted $C_{1-4}$ alkyl; R' is at each occurrence independently a substituted or unsubstituted $C_{1-4}$ alkyl, halogen, cyano, —OR or —NR$_2$; m is 0-3; and n is 0-3.

In some embodiments of compounds of formula (IV), $R^2$ is H, substituted or unsubstituted $C_{1-8}$ alkyl, substituted or unsubstituted cycloalkyl, substituted or unsubstituted heterocyclyl, substituted or unsubstituted $C_{1-4}$ alkyl-heterocyclyl, substituted or unsubstituted $C_{1-4}$ alkyl-aryl, or substituted or unsubstituted $C_{1-4}$ alkyl-cycloalkyl. For example, $R^2$ is H, methyl, ethyl, n-propyl, isopropyl, n-butyl, sec-butyl, isobutyl, tert-butyl, n-pentyl, isopentyl, cyclopentyl, cyclohexyl, tetrahydrofuranyl, tetrahydropyranyl, ($C_{1-4}$ alkyl)-phenyl, ($C_{1-4}$ alkyl)-cyclopropyl, ($C_{1-4}$ alkyl)-cyclobutyl, ($C_{1-4}$ alkyl)-cyclopentyl, ($C_{1-4}$ alkyl)-cyclohexyl, ($C_{1-4}$ alkyl)-pyrrolidyl, ($C_{1-4}$ alkyl)-piperidyl, ($C_{1-4}$ alkyl)-piperazinyl, ($C_{1-4}$ alkyl)-morpholinyl, ($C_{1-4}$ alkyl)-tetrahydrofuranyl, or ($C_{1-4}$ alkyl)-tetrahydropyranyl, each optionally substituted.

In other embodiments, $R^2$ is H, $C_{1-4}$ alkyl, ($C_{1-4}$alkyl)(OR),

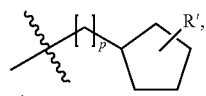

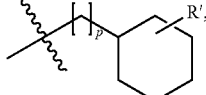

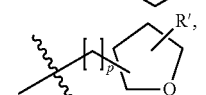

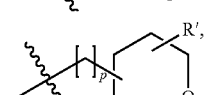

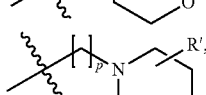

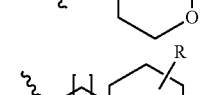

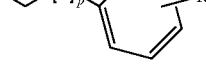

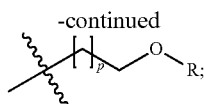

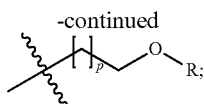

wherein R is at each occurrence independently H, or a substituted or unsubstituted $C_{1-4}$ alkyl (for example, methyl); R' is at each occurrence independently H, —OR, cyano, or a substituted or unsubstituted $C_{1-4}$ alkyl (for example, methyl); and p is 0-3.

In other embodiments of compounds of formula (IV), $R^2$ is H, $C_{1-4}$ alkyl, ($C_{1-4}$alkyl)(OR), wherein R is at each occurrence independently H, or a substituted or unsubstituted $C_{1-2}$ alkyl; R' is at each occurrence independently H, —OR, cyano, or a substituted or unsubstituted $C_{1-2}$ alkyl; and p is 0-1.

In other embodiments of compounds of formula (IV), $R^3$ is H.

In some such embodiments described herein, $R^1$ is substituted or unsubstituted aryl, or substituted or unsubstituted heteroaryl. For example, $R^1$ is phenyl, pyridyl, pyrimidyl, benzimidazolyl, 1H-pyrrolo[2,3-b]pyridyl, indazolyl, indolyl, 1H-imidazo[4,5-b]pyridine, pyridyl, 1H-imidazo[4,5-b]pyridin-2(3H)-onyl, 3H-imidazo[4,5-b]pyridyl, or pyrazolyl, each optionally substituted. In some embodiments, $R^1$ is phenyl substituted with one or more substituents independently selected from the group consisting of substituted or unsubstituted $C_{1-8}$ alkyl, substituted or unsubstituted heterocyclyl, aminocarbonyl, halogen, cyano, hydroxyalkyl and hydroxy. In others, $R^1$ is pyridyl substituted with one or more substituents independently selected from the group consisting of $C_{1-8}$ alkyl, substituted or unsubstituted heterocyclyl, halogen, aminocarbonyl, cyano, hydroxyalkyl, —OR, and —$NR_2$, wherein each R is independently H, or a substituted or unsubstituted $C_{1-4}$ alkyl. In still others, $R^1$ is 1H-pyrrolo[2,3-b]pyridyl or benzimidazolyl, optionally substituted with one or more substituents independently selected from the group consisting of substituted or unsubstituted $C_{1-8}$ alkyl, and —$NR_2$, wherein R is independently H, or a substituted or unsubstituted $C_{1-4}$ alkyl.

In certain embodiments, the compounds of formula (IV) have an $R^1$ group set forth herein and an $R^2$ group set forth herein.

In some embodiments of compounds of formula (IV), the compound at a concentration of 10 μM inhibits mTOR, DNA-PK, PI3K, or a combination thereof by at least about 50%. Compounds of formula (IV) may be shown to be inhibitors of the kinases above in any suitable assay system.

Representative TOR kinase inhibitors of formula (IV) include compounds from Table D.

TABLE D 7-(5-fluoro-2-methyl-4-(1H-1,2,4-triazol-3-yl)phenyl)-1-((trans-4-methoxycyclohexyl)methyl)-3,4-dihydropyrazino[2,3-b]pyrazin-2(1H)-one;
7-(6-(1H-1,2,4-triazol-3-yl)pyridin-3-yl)-1-(cis-4-methoxycyclohexyl)-3,4-dihydropyrazino[2,3-b]pyrazin-2(1H)-one;
7-(1H-pyrrolo[2,3-b]pyridin-3-yl)-1-(2-(tetrahydro-2H-pyran-4-yl)ethyl)-3,4-dihydropyrazino[2,3-b]pyrazin-2(1H)-one;
7-(5-fluoro-2-methyl-4-(1H-1,2,4-triazol-3-yl)phenyl)-1-((cis-4-methoxycyclohexyl)methyl)-3,4-dihydropyrazino[2,3-b]pyrazin-2(1H)-one;
1-ethyl-7-(1H-pyrrolo[3,2-b]pyridin-5-yl)-3,4-dihydropyrazino[2,3-b]pyrazin-2(1H)-one;
7-(6-(1H-1,2,4-triazol-3-yl)pyridin-3-yl)-1-((cis-4-methoxycyclohexyl)methyl)-3,4-dihydropyrazino[2,3-b]pyrazin-2(1H)-one;
7-(1H-benzo[d]imidazol-4-yl)-1-(2-(tetrahydro-2H-pyran-4-yl)ethyl)-3,4-dihydropyrazino[2,3-b]pyrazin-2(1H)-one;
7-(1H-pyrrolo[2,3-b]pyridin-4-yl)-1-(2-(tetrahydro-2H-pyran-4-yl)ethyl)-3,4-dihydropyrazino[2,3-b]pyrazin-2(1H)-one;
7-(6-(1H-1,2,4-triazol-3-yl)pyridin-3-yl)-1-((trans-4-methoxycyclohexyl)methyl)-3,4-dihydropyrazino[2,3-b]pyrazin-2(1H)-one;
7-(6-(1H-1,2,4-triazol-3-yl)pyridin-3-yl)-1-((trans-4-hydroxycyclohexyl)methyl)-3,4-dihydropyrazino[2,3-b]pyrazin-2(1H)-one;
7-(6-(1H-1,2,4-triazol-3-yl)pyridin-3-yl)-1-(cis-4-hydroxycyclohexyl)-3,4-dihydropyrazino[2,3-b]pyrazin-2(1H)-one;
7-(5-fluoro-2-methyl-4-(1H-1,2,4-triazol-3-yl)phenyl)-1-(cis-4-hydroxycyclohexyl)-3,4-dihydropyrazino[2,3-b]pyrazin-2(1H)-one;
7-(6-(1H-1,2,4-triazol-3-yl)pyridin-3-yl)-1-(tetrahydro-2H-pyran-4-yl)-3,4-dihydropyrazino[2,3-b]pyrazin-2(1H)-one;

TABLE D-continued 7-(6-(1H-1,2,4-triazol-3-yl)pyridin-3-yl)-1-(2-methoxyethyl)-3,4-dihydropyrazino[2,3-b]pyrazin-2(1H)-one;
7-(6-(1H-1,2,4-triazol-3-yl)pyridin-3-yl)-1-ethyl-3,4-dihydropyrazino[2,3-b]pyrazin-2(1H)-one;
7-(5-fluoro-2-methyl-4-(1H-1,2,4-triazol-3-yl)phenyl)-1-((cis-4-hydroxycyclohexyl)methyl)-3,4-dihydropyrazino[2,3-b]pyrazin-2(1H)-one;
7-(5-fluoro-2-methyl-4-(1H-1,2,4-triazol-3-yl)phenyl)-1-(tetrahydro-2H-pyran-4-yl)-3,4-dihydropyrazino[2,3-b]pyrazin-2(1H)-one;
7-(1H-indol-4-yl)-1-(2-(tetrahydro-2H-pyran-4-yl)ethyl)-3,4-dihydropyrazino[2,3-b]pyrazin-2(1H)-one;
7-(5-fluoro-2-methyl-4-(1H-1,2,4-triazol-3-yl)phenyl)-1-((trans-4-hydroxycyclohexyl)methyl)-3,4-dihydropyrazino[2,3-b]pyrazin-2(1H)-one;
7-(6-(1H-1,2,4-triazol-3-yl)pyridin-3-yl)-1-((cis-4-hydroxycyclohexyl)methyl)-3,4-dihydropyrazino[2,3-b]pyrazin-2(1H)-one;
7-(6-(1H-1,2,4-triazol-3-yl)pyridin-3-yl)-1-(trans-4-hydroxycyclohexyl)-3,4-dihydropyrazino[2,3-b]pyrazin-2(1H)-one;
7-(6-(1H-1,2,4-triazol-3-yl)pyridin-3-yl)-1-(trans-4-methoxycyclohexyl)-3,4-dihydropyrazino[2,3-b]pyrazin-2(1H)-one;
7-(6-(1H-1,2,4-triazol-3-yl)pyridin-3-yl)-1-isopropyl-3,4-dihydropyrazino[2,3-b]pyrazin-2(1H)-one;
7-(5-fluoro-2-methyl-4-(1H-1,2,4-triazol-3-yl)phenyl)-1-(trans-4-methoxycyclohexyl)-3,4-dihydropyrazino[2,3-b]pyrazin-2(1H)-one;
7-(5-fluoro-2-methyl-4-(1H-1,2,4-triazol-3-yl)phenyl)-1-(trans-4-hydroxycyclohexyl)-3,4-dihydropyrazino[2,3-b]pyrazin-2(1H)-one;
7-(5-fluoro-2-methyl-4-(1H-1,2,4-triazol-3-yl)phenyl)-1-(2-methoxyethyl)-3,4-dihydropyrazino[2,3-b]pyrazin-2(1H)-one;
7-(5-fluoro-2-methyl-4-(1H-1,2,4-triazol-3-yl)phenyl)-1-isopropyl-3,4-dihydropyrazino[2,3-b]pyrazin-2(1H)-one;
1-ethyl-7-(5-fluoro-2-methyl-4-(1H-1,2,4-triazol-3-yl)phenyl)-3,4-dihydropyrazino[2,3-b]pyrazin-2(1H)-one;
7-(2-hydroxypyridin-4-yl)-1-(2-(tetrahydro-2H-pyran-4-yl)ethyl)-3,4-dihydropyrazino[2,3-b]pyrazin-2(1H)-one;
1-isopropyl-7-(4-methyl-6-(1H-1,2,4-triazol-3-yl)pyridin-3-yl)-3,4-dihydropyrazino[2,3-b]pyrazin-2(1H)-one;
5-(8-isopropyl-7-oxo-5,6,7,8-tetrahydropyrazino[2,3-b]pyrazin-2-yl)-4-methylpicolinamide;
7-(1H-indazol-4-yl)-1-(2-(tetrahydro-2H-pyran-4-yl)ethyl)-3,4-dihydropyrazino[2,3-b]pyrazin-2(1H)-one;
7-(2-aminopyrimidin-5-yl)-1-(2-(tetrahydro-2H-pyran-4-yl)ethyl)-3,4-dihydropyrazino[2,3-b]pyrazin-2(1H)-one;
7-(2-aminopyridin-4-yl)-1-(2-(tetrahydro-2H-pyran-4-yl)ethyl)-3,4-dihydropyrazino[2,3-b]pyrazin-2(1H)-one;
7-(6-(methylamino)pyridin-3-yl)-1-(2-(tetrahydro-2H-pyran-4-yl)ethyl)-3,4-dihydropyrazino[2,3-b]pyrazin-2(1H)-one;
7-(6-hydroxypyridin-3-yl)-1-(2-(tetrahydro-2H-pyran-4-yl)ethyl)-3,4-dihydropyrazino[2,3-b]pyrazin-2(1H)-one;
7-(4-(1H-pyrazol-3-yl)phenyl)-1-(2-methoxyethyl)-3,4-dihydropyrazino[2,3-b]pyrazin-2(1H)-one;
7-(pyridin-3-yl)-1-(2-(tetrahydro-2H-pyran-4-yl)ethyl)-3,4-dihydropyrazino[2,3-b]pyrazin-2(1H)-one;
7-(1H-indazol-4-yl)-1-(2-methoxyethyl)-3,4-dihydropyrazino[2,3-b]pyrazin-2(1H)-one;
7-(1H-indazol-6-yl)-1-(2-methoxyethyl)-3,4-dihydropyrazino[2,3-b]pyrazin-2(1H)-one;
7-(pyrimidin-5-yl)-1-(2-(tetrahydro-2H-pyran-4-yl)ethyl)-3,4-dihydropyrazino[2,3-b]pyrazin-2(1H)-one;
7-(6-methoxypyridin-3-yl)-1-(2-(tetrahydro-2H-pyran-4-yl)ethyl)-3,4-dihydropyrazino[2,3-b]pyrazin-2(1H)-one;
1-(2-methoxyethyl)-7-(1H-pyrrolo[2,3-b]pyridin-5-yl)-3,4-dihydropyrazino[2,3-b]pyrazin-2(1H)-one;
1-ethyl-7-(1H-pyrrolo[2,3-b]pyridin-5-yl)-3,4-dihydropyrazino[2,3-b]pyrazin-2(1H)-one;
1-ethyl-7-(1H-indazol-4-yl)-3,4-dihydropyrazino[2,3-b]pyrazin-2(1H)-one;
7-(pyridin-4-yl)-1-(2-(tetrahydro-2H-pyran-4-yl)ethyl)-3,4-dihydropyrazino[2,3-b]pyrazin-2(1H)-one;
7-(6-aminopyridin-3-yl)-1-(2-(tetrahydro-2H-pyran-4-yl)ethyl)-3,4-dihydropyrazino[2,3-b]pyrazin-2(1H)-one;
1-methyl-7-(2-methyl-6-(4H-1,2,4-triazol-3-yl)pyridin-3-yl)-3,4-dihydropyrazino[2,3-b]pyrazin-2(1H)-one;
2-(2-hydroxypropan-2-yl)-5-(8-(trans-4-methoxycyclohexyl)-7-oxo-5,6,7,8-tetrahydropyrazino[2,3-b]pyrazin-2-yl)pyridine 1-oxide;
4-methyl-5-(7-oxo-8-((tetrahydro-2H-pyran-4-yl)methyl)-5,6,7,8-tetrahydropyrazino[2,3-b]pyrazin-2-yl)picolinamide;
5-(8-((cis-4-methoxycyclohexyl)methyl)-7-oxo-5,6,7,8-tetrahydropyrazino[2,3-b]pyrazin-2-yl)-4-methylpicolinamide;
7-(1H-pyrazol-4-yl)-1-(2-(tetrahydro-2H-pyran-4-yl)ethyl)-3,4-dihydropyrazino[2,3-b]pyrazin-2(1H)-one;
1-(trans-4-methoxycyclohexyl)-7-(4-methyl-6-(1H-1,2,4-triazol-3-yl)pyridin-3-yl)-3,4-dihydropyrazino[2,3-b]pyrazin-2(1H)-one;
3-((7-(2-methyl-6-(4H-1,2,4-triazol-3-yl)pyridin-3-yl)-2-oxo-3,4-dihydropyrazino[2,3-b]pyrazin-1(2H)-yl)methyl)benzonitrile;
1-((trans-4-methoxycyclohexyl)methyl)-7-(4-methyl-6-(1H-1,2,4-triazol-3-yl)pyridin-3-yl)-3,4-dihydropyrazino[2,3-b]pyrazin-2(1H)-one;
3-(7-oxo-8-(2-(tetrahydro-2H-pyran-4-yl)ethyl)-5,6,7,8-tetrahydropyrazino[2,3-b]pyrazin-2-yl)benzamide;

TABLE D-continued 5-(8-((trans-4-methoxycyclohexyl)methyl)-7-oxo-5,6,7,8-tetrahydropyrazino[2,3-b]pyrazin-2-yl)-4-methylpicolinamide;
3-((7-(6-(2-hydroxypropan-2-yl)pyridin-3-yl)-2-oxo-3,4-dihydropyrazino[2,3-b]pyrazin-1(2H)-yl)methyl)benzonitrile;
7-(6-(2-hydroxypropan-2-yl)pyridin-3-yl)-1-((1R,3R)-3-methoxycyclopentyl)-3,4-dihydropyrazino[2,3-b]pyrazin-2(1H)-one;
7-(6-(2-hydroxypropan-2-yl)pyridin-3-yl)-1-((1S,3R)-3-methoxycyclopentyl)-3,4-dihydropyrazino[2,3-b]pyrazin-2(1H)-one;
7-(6-(2-hydroxypropan-2-yl)pyridin-3-yl)-1-((1S,3S)-3-methoxycyclopentyl)-3,4-dihydropyrazino[2,3-b]pyrazin-2(1H)-one;
7-(6-(2-hydroxypropan-2-yl)pyridin-3-yl)-1-((1R,3S)-3-methoxycyclopentyl)-3,4-dihydropyrazino[2,3-b]pyrazin-2(1H)-one;
7-(1H-indazol-6-yl)-1-(2-(tetrahydro-2H-pyran-4-yl)ethyl)-3,4-dihydropyrazino[2,3-b]pyrazin-2(1H)-one;
7-(2-methyl-6-(4H-1,2,4-triazol-3-yl)pyridin-3-yl)-1-(2-morpholinoethyl)-3,4-dihydropyrazino[2,3-b]pyrazin-2(1H)-one;
1-(trans-4-hydroxycyclohexyl)-7-(2-methyl-6-(4H-1,2,4-triazol-3-yl)pyridin-3-yl)-3,4-dihydropyrazino[2,3-b]pyrazin-2(1H)-one;
1-(cis-4-hydroxycyclohexyl)-7-(2-methyl-6-(4H-1,2,4-triazol-3-yl)pyridin-3-yl)-3,4-dihydropyrazino[2,3-b]pyrazin-2(1H)-one;
7-(6-(2-hydroxypropan-2-yl)pyridin-3-yl)-1-(2-morpholinoethyl)-3,4-dihydropyrazino[2,3-b]pyrazin-2(1H)-one;
1-isopropyl-7-(2-methyl-6-(4H-1,2,4-triazol-3-yl)pyridin-3-yl)-3,4-dihydropyrazino[2,3-b]pyrazin-2(1H)-one;
7-(1H-imidazo[4,5-b]pyridin-6-yl)-1-(2-(tetrahydro-2H-pyran-4-yl)ethyl)-3,4-dihydropyrazino[2,3-b]pyrazin-2(1H)-one;
1-((cis-4-methoxycyclohexyl)methyl)-7-(2-methyl-6-(1H-1,2,4-triazol-3-yl)pyridin-3-yl)-3,4-dihydropyrazino[2,3-b]pyrazin-2(1H)-one;
1-(trans-4-hydroxycyclohexyl)-7-(6-(2-hydroxypropan-2-yl)pyridin-3-yl)-3,4-dihydropyrazino[2,3-b]pyrazin-2(1H)-one;
1-cis-4-hydroxycyclohexyl)-7-(6-(2-hydroxypropan-2-yl)pyridin-3-yl)-3,4-dihydropyrazino[2,3-b]pyrazin-2(1H)-one;
4-(7-oxo-8-(2-(tetrahydro-2H-pyran-4-yl)ethyl)-5,6,7,8-tetrahydropyrazino[2,3-b]pyrazin-2-yl)benzamide;
7-(1H-indazol-5-yl)-1-(2-(tetrahydro-2H-pyran-4-yl)ethyl)-3,4-dihydropyrazino[2,3-b]pyrazin-2(1H)-one;
7-(1H-pyrrolo[2,3-b]pyridin-5-yl)-1-(2-(tetrahydro-2H-pyran-4-yl)ethyl)-3,4-dihydropyrazino[2,3-b]pyrazin-2(1H)-one;
7-(2-methyl-6-(4H-1,2,4-triazol-3-yl)pyridin-3-yl)-1-(tetrahydro-2H-pyran-4-yl)-3,4-dihydropyrazino[2,3-b]pyrazin-2(1H)-one;
1-((1S,3R)-3-methoxycyclopentyl)-7-(2-methyl-6-(4H-1,2,4-triazol-3-yl)pyridin-3-yl)-3,4-dihydropyrazino[2,3-b]pyrazin-2(1H)-one;
1-((1R,3R)-3-methoxycyclopentyl)-7-(2-methyl-6-(4H-1,2,4-triazol-3-yl)pyridin-3-yl)-3,4-dihydropyrazino[2,3-b]pyrazin-2(1H)-one;
1-((1R,3S)-3-methoxycyclopentyl)-7-(2-methyl-6-(4H-1,2,4-triazol-3-yl)pyridin-3-yl)-3,4-dihydropyrazino[2,3-b]pyrazin-2(1H)-one;
1-((1S,3S)-3-methoxycyclopentyl)-7-(2-methyl-6-(4H-1,2,4-triazol-3-yl)pyridin-3-yl)-3,4-dihydropyrazino[2,3-b]pyrazin-2(1H)-one;
7-(1H-indol-5-yl)-1-(2-(tetrahydro-2H-pyran-4-yl)ethyl)-3,4-dihydropyrazino[2,3-b]pyrazin-2(1H)-one;
1-ethyl-7-(2-methyl-6-(4H-1,2,4-triazol-3-yl)pyridin-3-yl)-3,4-dihydropyrazino[2,3-b]pyrazin-2(1H)-one;
7-(1H-indol-6-yl)-1-(2-(tetrahydro-2H-pyran-4-yl)ethyl)-3,4-dihydropyrazino[2,3-b]pyrazin-2(1H)-one;
7-(4-(2-hydroxypropan-2-yl)phenyl)-1-(trans-4-methoxycyclohexyl)-3,4-dihydropyrazino[2,3-b]pyrazin-2(1H)-one;
7-(6-(2-hydroxypropan-2-yl)pyridin-3-yl)-1-(tetrahydro-2H-pyran-4-yl)-3,4-dihydropyrazino[2,3-b]pyrazin-2(1H)-one;
1-((trans-4-methoxycyclohexyl)methyl)-7-(2-methyl-6-(1H-1,2,4-triazol-3-yl)pyridin-3-yl)-3,4-dihydropyrazino[2,3-b]pyrazin-2(1H)-one;
7-(6-(2-hydroxypropan-2-yl)pyridin-3-yl)-1-((cis-4-methoxycyclohexyl)methyl)-3,4-dihydropyrazino[2,3-b]pyrazin-2(1H)-one;
1-(2-methoxyethyl)-7-(4-methyl-2-(methylamino)-1H-benzo[d]imidazol-6-yl)-3,4-dihydropyrazino[2,3-b]pyrazin-2(1H)-one;
7-(7-methyl-2-oxo-2,3-dihydro-1H-benzo[d]imidazol-5-yl)-1-((tetrahydro-2H-pyran-4-yl)methyl)-3,4-dihydropyrazino[2,3-b]pyrazin-2(1H)-one;
7-(2-methyl-4-(4H-1,2,4-triazol-3-yl)phenyl)-3,4-dihydropyrazino[2,3-b]pyrazin-2(1H)-one;
1-(2-methoxyethyl)-7-(4-methyl-6-(1H-1,2,4-triazol-3-yl)pyridin-3-yl)-3,4-dihydropyrazino[2,3-b]pyrazin-2(1H)-one;
1-benzyl-7-(2-methyl-4-(4H-1,2,4-triazol-3-yl)phenyl)-3,4-dihydropyrazino[2,3-b]pyrazin-2(1H)-one;
7-(3-fluoro-4-(4H-1,2,4-triazol-3-yl)phenyl)-1-(2-methoxyethyl)-3,4-dihydropyrazino[2,3-b]pyrazin-2(1H)-one;
7-(3-fluoro-4-(4H-1,2,4-triazol-3-yl)phenyl)-1-(2-(tetrahydro-2H-pyran-4-yl)ethyl)-3,4-dihydropyrazino[2,3-b]pyrazin-2(1H)-one;
7-(3-fluoro-2-methyl-4-(1H-1,2,4-triazol-3-yl)phenyl)-1-(2-methoxyethyl)-3,4-dihydropyrazino[2,3-b]pyrazin-2(1H)-one;
1-(trans-4-methoxycyclohexyl)-7-(2-methyl-6-(4H-1,2,4-triazol-3-yl)pyridin-3-yl)-3,4-dihydropyrazino[2,3-b]pyrazin-2(1H)-one;

TABLE D-continued 7-(6-(2-hydroxypropan-2-yl)pyridin-3-yl)-1-(trans-4-methoxycyclohexyl)-3,4-dihydropyrazino[2,3-b]pyrazin-2(1H)-one;
7-(5-fluoro-2-methyl-4-(4H-1,2,4-triazol-3-yl)phenyl)-1-(2-(tetrahydro-2H-pyran-4-yl)ethyl)-3,4-dihydropyrazino[2,3-b]pyrazin-2(1H)-one;
7-(3-fluoro-2-methyl-4-(1H-1,2,4-triazol-3-yl)phenyl)-1-(2-(tetrahydro-2H-pyran-4-yl)ethyl)-3,4-dihydropyrazino[2,3-b]pyrazin-2(1H)-one;
1-(2-methoxyethyl)-7-(2-methyl-6-(4H-1,2,4-triazol-3-yl)pyridin-3-yl)-3,4-dihydropyrazino[2,3-b]pyrazin-2(1H)-one;
7-(6-(2-hydroxypropan-2-yl)pyridin-3-yl)-1-((trans-4-methoxycyclohexyl)methyl)-3,4-dihydropyrazino[2,3-b]pyrazin-2(1H)-one;
1-(cyclopentylmethyl)-7-(6-(2-hydroxypropan-2-yl)pyridin-3-yl)-3,4-dihydropyrazino[2,3-b]pyrazin-2(1H)-one;
7-(4-(2-hydroxypropan-2-yl)phenyl)-1-(2-methoxyethyl)-3,4-dihydropyrazino[2,3-b]pyrazin-2(1H)-one;
(S)-7-(6-(1-hydroxyethyl)pyridin-3-yl)-1-(2-(tetrahydro-2H-pyran-4-yl)ethyl)-3,4-dihydropyrazino[2,3-b]pyrazin-2(1H)-one;
(R)-7-(6-(1-hydroxyethyl)pyridin-3-yl)-1-(2-(tetrahydro-2H-pyran-4-yl)ethyl)-3,4-dihydropyrazino[2,3-b]pyrazin-2(1H)-one;
7-(2-methyl-6-(4H-1,2,4-triazol-3-yl)pyridin-3-yl)-1-((tetrahydro-2H-pyran-4-yl)methyl)-3,4-dihydropyrazino[2,3-b]pyrazin-2(1H)-one;
7-(4-(2-hydroxypropan-2-yl)phenyl)-1-(2-(tetrahydro-2H-pyran-4-yl)ethyl)-3,4-dihydropyrazino[2,3-b]pyrazin-2(1H)-one;
7-(6-(2-hydroxypropan-2-yl)pyridin-3-yl)-1-(4-(trifluoromethyl)benzyl)-3,4-dihydropyrazino[2,3-b]pyrazin-2(1H)-one;
7-(6-(2-hydroxypropan-2-yl)pyridin-3-yl)-1-(3-(trifluoromethyl)benzyl)-3,4-dihydropyrazino[2,3-b]pyrazin-2(1H)-one;
7-(6-(2-hydroxypropan-2-yl)pyridin-3-yl)-1-(3-methoxypropyl)-3,4-dihydropyrazino[2,3-b]pyrazin-2(1H)-one;
7-(4-methyl-6-(1H-1,2,4-triazol-3-yl)pyridin-3-yl)-1-(2-(tetrahydro-2H-pyran-4-yl)ethyl)-3,4-dihydropyrazino[2,3-b]pyrazin-2(1H)-one;
7-(6-(2-hydroxypropan-2-yl)pyridin-3-yl)-1-(2-methoxyethyl)-3,4-dihydropyrazino[2,3-b]pyrazin-2(1H)-one;
7-(6-(2-hydroxypropan-2-yl)pyridin-3-yl)-1-((tetrahydro-2H-pyran-4-yl)methyl)-3,4-dihydropyrazino[2,3-b]pyrazin-2(1H)-one;
7-(4-methyl-2-(methylamino)-1H-benzo[d]imidazol-6-yl)-1-((tetrahydro-2H-pyran-4-yl)methyl)-3,4-dihydropyrazino[2,3-b]pyrazin-2(1H)-one;
7-(2-amino-4-methyl-1H-benzo[d]imidazol-6-yl)-1-((tetrahydro-2H-pyran-4-yl)methyl)-3,4-dihydropyrazino[2,3-b]pyrazin-2(1H)-one;
7-(2-methyl-6-(4H-1,2,4-triazol-3-yl)pyridin-3-yl)-1-(2-(tetrahydro-2H-pyran-4-yl)ethyl)-3,4-dihydropyrazino[2,3-b]pyrazin-2(1H)-one;
(R)-7-(6-(2-hydroxypropan-2-yl)pyridin-3-yl)-3-methyl-1-(2-(tetrahydro-2H-pyran-4-yl)ethyl)-3,4-dihydropyrazino[2,3-b]pyrazin-2(1H)-one;
(S)-7-(6-(2-hydroxypropan-2-yl)pyridin-3-yl)-3-methyl-1-(2-(tetrahydro-2H-pyran-4-yl)ethyl)-3,4-dihydropyrazino[2,3-b]pyrazin-2(1H)-one;
7-(6-(2-hydroxypropan-2-yl)pyridin-3-yl)-3,3-dimethyl-1-(2-(tetrahydro-2H-pyran-4-yl)ethyl)-3,4-dihydropyrazino[2,3-b]pyrazin-2(1H)-one;
7-(2-amino-4-methyl-1H-benzo[d]imidazol-6-yl)-1-(2-(tetrahydro-2H-pyran-4-yl)ethyl)-3,4-dihydropyrazino[2,3-b]pyrazin-2(1H)-one;
7-(6-(2-hydroxypropan-2-yl)pyridin-3-yl)-1-(2-(tetrahydro-2H-pyran-4-yl)ethyl)-3,4-dihydropyrazino[2,3-b]pyrazin-2(1H)-one;
7-(2-methyl-4-(1H-1,2,4-triazol-3-yl)phenyl)-1-(2-(tetrahydro-2H-pyran-4-yl)ethyl)-3,4-dihydropyrazino[2,3-b]pyrazin-2(1H)-one;
7-(4-(1H-1,2,4-triazol-5-yl)phenyl)-1-(2-(tetrahydro-2H-pyran-4-yl)ethyl)-3,4-dihydropyrazino[2,3-b]pyrazin-2(1H)-one;
1-(1-hydroxypropan-2-yl)-7-(2-methyl-6-(1H-1,2,4-triazol-3-yl)pyridin-3-yl)-3,4-dihydropyrazino[2,3-b]pyrazin-2(1H)-one; and
1-(2-hydroxyethyl)-7-(2-methyl-6-(1H-1,2,4-triazol-3-yl)pyridin-3-yl)-3,4-dihydropyrazino[2,3-b]pyrazin-2(1H)-one,
and pharmaceutically acceptable salts, clathrates, solvates, stereoisomers, tautomers, and prodrugs thereof.

5.3 Methods for Making TOR Kinase Inhibitors

The TOR kinase inhibitors can be obtained via standard, well-known synthetic methodology, see e.g., March, J. Advanced Organic Chemistry; Reactions Mechanisms, and Structure, 4th ed., 1992. Starting materials useful for preparing compounds of formula (III) and intermediates therefore, are commercially available or can be prepared from commercially available materials using known synthetic methods and reagents.

Particular methods for preparing compounds of formula (I) are disclosed in U.S. Pat. No. 7,981,893, issued Jul. 19, 2011, incorporated by reference herein in its entirety. Particular methods for preparing compounds of formula (II) are disclosed in U.S. Pat. No. 7,968,556, issued Jun. 28, 2011, incorporated by reference herein in its entirety. Particular methods for preparing compounds of formula (III) and (IV) are disclosed in U.S. Publication No. 2010/0216781, filed Oct. 26, 2009, and U.S. Publication No. 2011/0137028, filed Oct. 25, 2010, incorporated by reference herein in its entirety.

5.4 Methods of Use

Provided herein are methods for detecting or measuring the inhibition of TOR kinase activity in a patient, comprising measuring the amount of phosphorylated PRAS40, GSK3β and/or p70S6K1 in a biological sample from said patient, for example a peripheral blood sample, prior to and after the administration of the TOR kinase inhibitor to said patient. In one embodiment, the amount of PRAS40, GSK3β and/or p70S6K1 is measured using flow cytometry, ELISA, immunohistochemistry (IHC) using phosphorylation-specific antibodies, Meso Scale Discovery (MSD®) assays, western blotting, immunofluorescence, or Luminex® technologies. The methods provided herein are believed to have utility in following the inhibition of TOR kinase in a patient. In certain embodiments, the patient is treated for a disease or disorder provided herein.

Further provided herein are methods for determining a dose-response relationship for the administration of a TOR kinase inhibitor to a patient, wherein said patient is administered varying doses of said TOR kinase inhibitor and the amount of TOR kinase activity inhibition in said patient resulting from each dose of said TOR kinase inhibitor is determined by measuring the amount of phosphorylated PRAS40, GSK3β and/or p70S6K1 in a biological sample from said patient, for example a peripheral blood sample, prior to and after the administration of each dose of the TOR kinase inhibitor to said patient. In certain embodiments, the patient is treated for a disease or disorder provided herein.

In one embodiment, provided herein are methods for inhibiting phosphorylation of PRAS40, GSK3β and/or p70S6K1 in a patient having cancer (for example, prostate cancer, lung cancer, colon cancer, glioma or breast cancer), comprising administering an effective amount of a TOR kinase inhibitor to said patient. In some such embodiments, the inhibition of phosphorylation is assessed in a biological sample of the patient, such as in circulating blood and/or tumor cells, skin biopsies and/or tumor biopsies or aspirate. In such embodiments, the amount of inhibition of phosphorylation is assessed by comparison of the amount of phospho-PRAS40, GSK3β and/or p70S6K1 before and after administration of the TOR kinase inhibitor. In certain embodiments, the patient is treated for a disease or disorder provided herein.

In certain embodiments, provided herein are methods for measuring inhibition of phosphorylation of PRAS40, GSK3β and/or p70S6K1 in a patient having cancer (for example, prostate cancer, lung cancer, colon cancer, glioma or breast cancer), comprising administering an effective amount of a TOR kinase inhibitor to said patient, measuring the amount of phosphorylated PRAS40, GSK3β and/or p70S6K1 in said patient, and comparing said amount of phosphorylated PRAS40, GSK3β and/or p70S6K1 to that of said patient prior to administration of an effective amount of a TOR kinase inhibitor. In certain embodiments, the patient is treated for a disease or disorder provided herein.

In certain embodiments, provided herein are methods for measuring inhibition of phosphorylation of PRAS40, GSK3β and/or p70S6K1 in a biological sample of a patient having cancer (for example, prostate cancer, lung cancer, colon cancer, glioma or breast cancer), comprising administering an effective amount of a TOR kinase inhibitor to said patient and comparing the amount of phosphorylated PRAS40, GSK3β and/or p70S6K1 in a biological sample of said patient obtained prior to and after administration of said TOR kinase inhibitor, wherein less phosphorylated PRAS40, GSK3β and/or p70S6K1 in said biological sample obtained after administration of said TOR kinase inhibitor relative to the amount of phosphorylated PRAS40, GSK3β and/or p70S6K1 in said biological sample obtained prior to administration of said TOR kinase inhibitor indicates inhibition. In certain embodiments, the patient is treated for a disease or disorder provided herein.

Provided herein are methods for treating a cancer treatable by inhibition of phosphorylation of PRAS40, GSK3β and/or p70S6K1, comprising administering an effective amount of a TOR kinase inhibitor to a patient having a cancer treatable by inhibition of phosphorylation of PRAS40, GSK3β and/or p70S6K1. In certain such embodiments, the cancer is prostate cancer, lung cancer, colon cancer, glioma or breast cancer.

Also provided herein are methods for treating a cancer treatable by inhibition of phosphorylation of PRAS40, GSK3β and/or p70S6K1 comprising screening an individual for the presence of a cancer expressing PRAS40, GSK3β and/or p70S6K1 and administering an effective amount of a TOR kinase inhibitor to a patient having a cancer treatable by inhibition of phosphorylation of PRAS40, GSK3β and/or p70S6K1. In certain such embodiments, the cancer is prostate cancer, lung cancer, colon cancer, glioma or breast cancer.

Also provided herein are methods for inhibiting the in vivo phosphorylation of PRAS40, GSK3β and/or p70S6K1, comprising administering an effective amount of a TOR kinase inhibitor to a patient having a cancer treatable by inhibition of phosphorylation of PRAS40, GSK3β and/or p70S6K1. In certain such embodiments, the cancer is prostate cancer, lung cancer, colon cancer, glioma or breast cancer.

Also provided herein are methods for predicting the likelihood of a cancer of a patient being responsive to TOR kinase inhibitor therapy, comprising: screening a biological sample of said patient for the presence of PRAS40, GSK3β and/or p70S6K1, the phosphorylation of which is inhibited by a TOR kinase inhibitor; wherein the presence of PRAS40, GSK3β and/or p70S6K1, the phosphorylation of which is inhibited by a TOR kinase inhibitor, indicates an increased likelihood that a cancer of said patient will be responsive to TOR kinase inhibitor therapy. In certain embodiments, the methods provided herein further comprising the treatment of a patient predicted to have an increased likelihood of being responsive to TOR kinase inhibitor therapy, comprising administering an effective amount of a TOR kinase inhibitor to said patient. In certain embodiments, the patient has cancer. In certain such embodiments, the cancer is prostate cancer, lung cancer, colon cancer, glioma or breast cancer.

Inhibition of phosphorylation of PRAS40, GSK3β and/or p70S6K1 can be measured in blood, skin, tumor, and/or circulating tumor cells (CTCs) in blood by various methodology including flow cytometry, ELISA, immunohistochemistry (IHC) using phosphorylation-specific antibodies, Meso Scale Discovery assays, western blotting, immunofluorescence, and Luminex® technologies. In certain embodiments, the methods provided herein comprise measuring the inhibition of phosphorylation of PRAS40, GSK3β and/or p70S6K1 using one or more of these methods.

In certain embodiments, the method further comprises predicting the therapeutic efficacy of treatment of a patient with a TOR kinase inhibitor, comprising administering a TOR kinase inhibitor to said patient; obtaining a biological sample from said patient; measuring the level of phosphorylation of PRAS40, GSK3β and/or p70S6K1 in said biological sample; and comparing said measurement with a control measurement from the patient prior to treatment with said TOR kinase inhibitor; wherein a decrease in phosphorylation of PRAS40, GSK3β and/or p70S6K1 in said biological sample relative to the control measurement indicates an increase in therapeutic efficacy of treatment of said patient with a TOR kinase inhibitor. In certain embodiments, the patient is treated for a disease or disorder provided herein, and the efficacy of said treatment is predicted and/or determined using said methods.

Further provided herein are methods for determining whether a patient is sensitive to a TOR kinase inhibitor, comprising administering said patient said TOR kinase inhibitor and determining whether or not TOR kinase activity is inhibited in said patient by measuring the amount of phosphorylated PRAS40, GSK3β and/or p70S6K1 in a biological sample from said patient, for example a peripheral blood sample, prior to and after the administration of the TOR kinase inhibitor to said patient. In certain embodiments, the methods provided herein further comprising the treatment of a patient determined to be sensitive to a TOR kinase inhibitor, comprising administering an effective amount of a TOR kinase inhibitor to said patient. In certain embodiments, the patient has cancer. In certain such embodiments, the cancer is prostate cancer, lung cancer, colon cancer, glioma or breast cancer.

Further provided herein are methods for determining the effective amount of a TOR kinase inhibitor for the treatment of a cancer treatable by inhibition of phosphorylation of PRAS40, GSK3β and/or p70S6K1 in a patient, comprising administering said patient varying doses of said TOR kinase inhibitor and determining the amount of TOR kinase activity inhibition in said patient resulting from each dose of said TOR kinase inhibitor by measuring the amount of phosphorylated PRAS40, GSK3β and/or p70S6K1 in a biological sample from said patient, for example a peripheral blood sample, prior to and after the administration of each dose of TOR kinase inhibitor to said patient. In certain embodiments, the methods provided herein further comprising the treatment of a patient, comprising administering said effective amount of a TOR kinase inhibitor to said patient. In certain embodiments, the patient has cancer. In certain such embodiments, the cancer is prostate cancer, lung cancer, colon cancer, glioma or breast cancer.

In certain embodiments, the methods provided herein are based on comparison of the level of phosphorylated PRAS40, GSK3β and/or p70S6K1 in a biological sample from a patient having cancer to a reference level of phosphorylated PRAS40, GSK3β and/or p70S6K1 or the level of phosphorylated PRAS40, GSK3β and/or p70S6K1 in a control sample. The phosphorylated PRAS40, GSK3β and/or p70S6K1 level is used to determine or to predict, for example, the likelihood of the responsiveness of the patient treatment with a TOR kinase inhibitor.

Also provided herein is a kit for detecting inhibition of phosphorylation of PRAS40, GSK3β and/or p70S6K1 by a TOR kinase inhibitor, comprising reagents for measuring phosphorylation of PRAS40, GSK3β and/or p70S6K1 and one or more TOR kinase inhibitors.

In some embodiments, the TOR kinase inhibitor is a compound as described herein. In one embodiment, the TOR kinase inhibitor is Compound 1 (a TOR kinase inhibitor set forth herein having molecular formula $C_{21}H_{27}N_5O_3$). In one embodiment, Compound 1 is 7-(6-(2-hydroxypropan-2-yl) pyridin-3-yl)-1-((1r,4r)-4-methoxycyclohexyl)-3,4-dihydropyrazino-[2,3-b]pyrazin-2(1H)-one.

A TOR kinase inhibitor can be combined with other pharmacologically active compounds ("second active agents") in methods and compositions described herein. It is believed that certain combinations may work in the treatment of particular types of diseases or disorders, and conditions and symptoms associated with such diseases or disorders. A TOR kinase inhibitor can also work to alleviate adverse effects associated with certain second active agents, and vice versa.

One or more second active ingredients or agents can be used in the methods and compositions described herein. Second active agents can be large molecules (e.g., proteins) or small molecules (e.g., synthetic inorganic, organometallic, or organic molecules).

Administration of a TOR kinase inhibitor and one or more second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. A preferred route of administration for a TOR kinase inhibitor is oral. Preferred routes of administration for the second active agents or ingredients of the invention are known to those of ordinary skill in the art. See, e.g., *Physicians' Desk Reference*, 1755-1760 (56th ed., 2002).

In one embodiment, a second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount(s) of a TOR kinase inhibitor and any optional additional active agents concurrently administered to the patient.

Further provided herein are methods of reducing, treating and/or preventing adverse or undesired effects associated with conventional therapy including, but not limited to, surgery, chemotherapy, radiation therapy, hormonal therapy, biological therapy and immunotherapy. TOR kinase inhibitors and other active ingredients can be administered to a patient prior to, during, or after the occurrence of the adverse effect associated with conventional therapy.

5.5 Pharmaceutical Compositions and Routes of Administration

Provided herein are compositions comprising an effective amount of a TOR kinase inhibitor and compositions comprising an effective amount of a TOR kinase inhibitor and a pharmaceutically acceptable carrier or vehicle. In some embodiments, the pharmaceutical composition described herein are suitable for oral, parenteral, mucosal, transdermal or topical administration.

The TOR kinase inhibitors can be administered to a patient orally or parenterally in the conventional form of preparations, such as capsules, microcapsules, tablets, granules, powder, troches, pills, suppositories, injections, suspensions and syrups. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g, sodium benzoate, sodium bisulfite, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and base wax (e.g., cocoa butter, white petrolatum or polyethylene glycol). The effective amount of the TOR kinase inhibitor in the pharmaceutical composition may be at a level that will exercise the desired effect; for example, about 0.005 mg/kg of a patient's body weight to about 10 mg/kg of a patient's body weight in unit dosage for both oral and parenteral administration.

The dose of a TOR kinase inhibitor to be administered to a patient is rather widely variable and can be patient to the judgment of a health-care practitioner. In general, the TOR kinase inhibitors can be administered one to four times a day in a dose of about 0.005 mg/kg of a patient's body weight to about 10 mg/kg of a patient's body weight in a patient, but the above dosage may be properly varied depending on the age, body weight and medical condition of the patient and the type of administration. In one embodiment, the dose is about 0.01 mg/kg of a patient's body weight to about 5 mg/kg of a patient's body weight, about 0.05 mg/kg of a patient's body weight to about 1 mg/kg of a patient's body weight, about 0.1 mg/kg of a patient's body weight to about 0.75 mg/kg of a patient's body weight or about 0.25 mg/kg of a patient's body weight to about 0.5 mg/kg of a patient's body weight. In one embodiment, one dose is given per day In another embodiment, two doses are given per day. In any given case, the amount of the TOR kinase inhibitor administered will depend on such factors as the solubility of the active component, the formulation used and the route of administration.

In another embodiment, provided herein are methods for the treatment or prevention of a disease or disorder comprising the administration of about 0.375 mg/day to about 750 mg/day, about 0.75 mg/day to about 375 mg/day, about 3.75 mg/day to about 75 mg/day, about 7.5 mg/day to about 55 mg/day or about 18 mg/day to about 37 mg/day of a TOR kinase inhibitor to a patient in need thereof. In a particular embodiment, the methods disclosed herein comprise the administration of 15 mg/day, 30 mg/day, 45 mg/day or 60 mg/day of a TOR kinase inhibitor to a patient in need thereof. In another, the methods disclosed herein comprise administration of 0.5 mg/day, 1 mg/day, 2 mg/day, 4 mg/day, 8 mg/day, 16 mg/day, 20 mg/day, 25 mg/day, 30 mg/day or 40 mg/day of a TOR kinase inhibitor to a patient in need thereof.

In another embodiment, provided herein are methods for the treatment or prevention of a disease or disorder comprising the administration of about 0.1 mg/day to about 1200 mg/day, about 1 mg/day to about 100 mg/day, about 10 mg/day to about 1200 mg/day, about 10 mg/day to about 100 mg/day, about 100 mg/day to about 1200 mg/day, about 400 mg/day to about 1200 mg/day, about 600 mg/day to about 1200 mg/day, about 400 mg/day to about 800 mg/day or about 600 mg/day to about 800 mg/day of a TOR kinase inhibitor to a patient in need thereof. In a particular embodiment, the methods disclosed herein comprise the administration of 0.1 mg/day, 0.5 mg/day, 1 mg/day, 10 mg/day, 15 mg/day, 20 mg/day, 30 mg/day, 40 mg/day, 45 mg/day, 50 mg/day, 60 mg/day, 75 mg/day, 100 mg/day, 125 mg/day, 150 mg/day, 200 mg/day, 250 mg/day, 300 mg/day, 400 mg/day, 600 mg/day or 800 mg/day of a TOR kinase inhibitor to a patient in need thereof.

In another embodiment, provided herein are unit dosage formulations that comprise between about 0.1 mg and about 2000 mg, about 1 mg and 200 mg, about 35 mg and about 1400 mg, about 125 mg and about 1000 mg, about 250 mg and about 1000 mg, or about 500 mg and about 1000 mg of a TOR kinase inhibitor.

In a particular embodiment, provided herein are unit dosage formulation comprising about 0.1 mg, 0.25 mg, 0.5 mg, 1 mg, 5 mg, 10 mg, 15 mg, 20 mg, 30 mg, 45 mg, 50 mg, 60 mg, 75 mg, 100 mg, 125 mg, 150 mg, 200 mg, 250 mg, 300 mg, 400 mg, 600 mg or 800 mg of a TOR kinase inhibitor.

In another embodiment, provided herein are unit dosage formulations that comprise 0.1 mg, 0.25 mg, 0.5 mg, 1 mg, 2.5 mg, 5 mg, 10 mg, 15 mg, 20 mg, 30 mg, 35 mg, 50 mg, 70 mg, 100 mg, 125 mg, 140 mg, 175 mg, 200 mg, 250 mg, 280 mg, 350 mg, 500 mg, 560 mg, 700 mg, 750 mg, 1000 mg or 1400 mg of a TOR kinase inhibitor. In a particular embodiment, provided herein are unit dosage formulations that comprise 10 mg, 15 mg, 20 mg, 30 mg, 45 mg or 60 mg of a TOR kinase inhibitor.

A TOR kinase inhibitor can be administered once, twice, three, four or more times daily.

A TOR kinase inhibitor can be administered orally for reasons of convenience. In one embodiment, when administered orally, a TOR kinase inhibitor is administered with a meal and water. In another embodiment, the TOR kinase inhibitor is dispersed in water or juice (e.g., apple juice or orange juice) and administered orally as a suspension. In another embodiment, when administered orally, a TOR kinase inhibitor is administered in a fasted state.

The TOR kinase inhibitor can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

In one embodiment, provided herein are capsules containing a TOR kinase inhibitor without an additional carrier, excipient or vehicle.

In another embodiment, provided herein are compositions comprising an effective amount of a TOR kinase inhibitor and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts, such as the hydrochloride salt. In general, all of the compositions are prepared according to known methods in pharmaceutical chemistry. Capsules can be prepared by mixing a TOR kinase inhibitor with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. In one embodiment, the pharmaceutical composition is lactose-free. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the die. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer a TOR kinase inhibitor as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the TOR kinase inhibitor can be delayed or prolonged by proper formulation. For example, a slowly soluble pellet of the TOR kinase inhibitor can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending the TOR kinase inhibitor in oily or emulsified vehicles that allow it to disperse slowly in the serum.

Kits

Provided herein are kits comprising a TOR kinase inhibitor and means for measuring the amount of inhibition of phosphorylation of PRAS40, GSK3β and/or p70S6K1 in a patient. In certain embodiments, the kits comprise means for measuring inhibition of phosphorylation of PRAS40, GSK3β and/or p70S6K1 in circulating blood or tumor cells and/or skin biopsies or tumor biopsies/aspirates of a patient. In certain embodiments, provided herein are kits comprising a TOR kinase inhibitor and means for measuring the amount of inhibition of phosphorylation as assessed by comparison of the amount of phospho-PRAS40, GSK3β and/or p70S6K1 before, during and/or after administration of the TOR kinase inhibitor. In certain embodiments, the patient has a cancer, for example, prostate cancer, lung cancer, colon cancer, glioma or breast cancer.

Inhibition of phosphorylation of PRAS40, GSK3β and/or p70S6K1 can be measured in blood, skin, tumor, and/or circulating tumor cells (CTCs) in blood by various methodology including flow cytometry, ELISA, immunohistochemistry (IHC) using phosphorylation-specific antibodies.

In certain embodiments, the kits provided herein comprise an amount of a TOR kinase inhibitor effective for treating or preventing a cancer, for example, prostate cancer, lung cancer, colon cancer, glioma or breast cancer. In certain embodiments, the kits provided herein comprise a TOR kinase inhibitor having the molecular formula $C_{16}H_{16}N_8O$. In certain embodiments, the kits provided herein comprise Compound 1.

In certain embodiments, the kits provided herein further comprise instructions for use, such as for administering a TOR kinase inhibitor and/or monitoring patient response to administration of a TOR kinase inhibitor.

EXAMPLES

Biological Examples

Biochemical Assays

Determination of Phospho-p70S6K (T389) in Cell Lysates.

MSD® biomarker detection assays provide a rapid and convenient method for measuring the total and phosphorylated levels of protein targets within a single small-volume sample. In the assay, an antibody for a specific protein target is coated on one electrode (or spot) per well. The samples (cell lysates) are added to the well with a solution containing the detection antibody labeled with an electrochemiluminescent (ECL) compound, MSD SULFOTAG™ label, over the course of one or more incubation periods. The total protein present in the sample binds to the capture antibodies immobilized on the working electrode surface; recruitment of the labeled detection antibody by bound phospho-p70S6K completes the sandwich. MSD Read Buffer that provides the appropriate chemical environment for ECL is added and the plate is read using an MSD SECTOR™ Imager. Inside the SECTOR Imager, a voltage is applied to the plate electrodes which cause the labels bound to the electrode surface to emit light. The instrument measures intensity of the emitted light to afford a quantitative measure of the amount of phosphorylated protein present in the sample.

Cell Treatment.

Cells were plated in 96-well flat bottom plates at the required density determined for each cell line and the cells were allowed to equilibrate at 37° C., 5% $CO_2$ overnight. The following day, the cells were treated with Compound 1 over a range of concentrations for one hour in 5% $CO_2$ at 37° C. After the incubation period, the culture medium was removed carefully with an aspirator. The plate was placed on ice and 50 μL of 1× Tris Lysis Buffer were added to each well. The plate was placed on a shaker at 4° C. for one hour to lyse the cells. At that point, the plate was either frozen at −80° C. for later analysis or immediately assayed for phosphoproteins as described below. To monitor interassay variability, Compound 1 was compared among all plates as a reference standard.

Assay Protocol.

The assay plate was incubated with 150 μL of MSD Blocking Buffer for one hour with shaking at room temperature. The plates were washed 3 times with Tris Wash Buffer. Then 35 μL of cell lysate was added to the wells and incubated for one hour with shaking at room temperature. The solution was removed from the wells and the plate was washed 3 times with wash buffer. Twenty-five microliters of the appropriate antibody solution was then incubated for one hour with shaking at room temperature. The solution was removed from the wells and the plate was washed 3 times with wash buffer. Then 150 µL of 1×MSD Read Buffer T was added to each well. The plate was read on the SECTOR Imager plate reader.

Determination of Phospho-GSK3β(S9), Phospho-PRAS40(T246) and Phospho-4E-BP1(T46) and the Effect of Compound 1 or Rapamycin.

The multiplex Luminex assay format differs from conventional enzyme-linked immunosorbent assay (ELISA) in that the multiplex capture antibody is attached to a polystyrene bead whereas the ELISA capture antibody is attached to the microplate well. The use of the suspension bead-based technology enables the multiplexing capabilities of the Luminex assays. The xMAP® technology uses 5.6 micron polystyrene microspheres, which are internally dyed with red and infrared fluorophores of differing intensities. Each bead is given a unique number, or bead region, allowing differentiation of one bead from another. Beads covalently bound to different specific antibodies can be mixed in the same assay, utilizing a 96-well microplate format. At the completion of the sandwich immunoassay, beads can be read, using the Luminex 100™ or Luminex 200 detection system, in single-file by dual lasers for classification and quantification of each analyte. The Akt-Pathway Phospho 5-plex kit used was custom made and includes the ability to simultaneously measure p-GSK3β (S9), p-PRAS40(T246), and p-4E-BP1(T46).

Cell Treatment and Assay Protocol.

Cells were plated at the required density. The cells were treated with either Compound 1 or rapamycin over a range of concentrations for 1 hour in 5% $CO_2$ at 37° C. Compound 1 and rapamycin were used at the same concentrations as for the proliferation assay. As for the cell proliferation assay, a reference standard was included in the assay for PC3 cells and the coefficient of variation for assay of p-GSK3β(S9) was 37.8% (n=30), p-PRAS40(T246) was 27.8% (n=30) and for p4E-BP1(T46) was 13.5% (n=4). For three cell lines (HCT-116, MDA-MB-231 and HT29) in the assay for phosphorylation of GSK3β, PRAS40 and 4E-BP1, IGF-I stimulation (500 ng/mL, recombinant human IGF-I) for the last 10 min of incubation was used. The media was aspirated from the wells and the plate was placed on ice. Then 35 µL of Lysis Buffer was added to each well and incubated on ice for at least 30 minutes. During the incubation, the standard curve for each phosphoprotein was prepared. The standards provided were reconstituted and serial dilutions were prepared according to the manufacturer's instructions. At the end of the cell lysis step, 36 µL of the lysate was transferred to a V-bottom plate and spun at 4° C. at 2000 rpm for 5 minutes. Both the 1× Luminex bead and 1× detector antibody solutions were prepared during this time. The 1× bead solution was vortexed and 25 µL was added into each well of a black round bottom plate. Then 50 µL of the 1× detector antibody was added to each well. Fifty microliters (50 µL) of the prepared standards were added to the designated wells. Then 25 µL of the assay diluent was added to each well designated for the compound-treated cell lysates. At the end of the spin, 25 µL of cell lysate was added to the corresponding wells of the black assay plate. The assay plate was covered with the white plate lid and incubated for 3 hours at room temperature on an orbital shaker.

Approximately 10-15 minutes prior to the end of the first incubation, the secondary antibody solution was prepared according to the vendor's protocol. Goat anti-rabbit R-phycoerythrin red fluorescent protein (RPE) supplied as a 10× concentrate was diluted to generate a 1× goat anti-rabbit RPE stock. The 96-well filter plate was pre-wet with 200 µL of 1× Working wash solution. At the end of the 3 hour incubation, a multichannel pipette was used to transfer the entire contents from each assay well into the wells of the filter plate. The liquid from the wells was removed by aspiration with the vacuum manifold. Then 200 µL of 1× Working wash solution was added into each well. The wash solution was aspirated using the vacuum manifold after 15-30 seconds. This wash step was repeated one time. The bottom of the plate was blotted on clean paper towels to remove residual liquid. One hundred microliters (100 µL) of diluted anti-rabbit RPE was added to each well and incubated for 30 minutes at room temperature on an orbital shaker. The liquid was then aspirated with the vacuum manifold. Then 200 µL of 1× Working wash solution was added into each well. The plates were washed three times with the wash solution. The plate was blotted on clean paper towels to remove residual liquid. Then 100 µL of 1× Working wash solution was added to each well to re-suspend the beads. The plates were then read on the Luminex 200 detection system. The Excel data was transferred to Activity Base and the $IC_{50}$ values were calculated.

Compound 1 Inhibition of Molecular Phospho-Biomarkers for the mTOR Pathway and the Complexes TORC1 and TORC2; Comparison with Rapamycin.

The activity of the TORC1 complex can be followed from the phosphorylation status of 4E-BP1(T46), a direct substrate of mTOR kinase and S6RP(S235/S236), a downstream substrate from mTOR. The activity of the TORC2 complex can be followed directly from the phosphorylation status of Akt(S473) and indirectly from the phosphorylation status of AKT substrates, GSK3β(S9) and PRAS40(T246). The potencies for Compound 1 inhibition of molecular phospho-biomarkers of the mTOR pathway are shown for 7 cell lines analyzed at the molecular level in Table 3. The potency for Compound 1 inhibition of the particular biomarkers 4E-BP1(T46), S6RP(S235/S236), and Akt(S473) for the mTOR pathway have been compared with rapamycin. Rapamycin demonstrated a remarkable potency in the picomolar range for the inhibition of the indirect substrate, S6RP(S235/S236), a substrate of the p70S6 kinase which is directly activated by the TORC1 complex. The $IC_{50}$ values for rapamycin were 19 and 29 pM for inhibition of S6RP (S235/S236) phosphorylation in PC3 and HCT116 cell lines, respectively. However, one of the direct TORC1 substrates 4E-BP1(T46) was not inhibited by rapamycin up to concentrations tested of 10 µM. Compound 1 inhibited phosphorylation of both the direct substrate and downstream substrate at sub-micromolar concentrations. As expected, rapamycin did not inhibit the phosphorylation of Akt(S473) (data not shown), a direct substrate of the TORC2 complex, for which rapamycin is known not to affect. As shown in Table 1, Compound 1 was able to produce sub-micromolar $IC_{50}$ values for the inhibition of both TORC1 and TORC2 direct and indirect substrates for those cell lines exhibiting sub-micromolar $IC_{50}$ values for growth inhibition. The indirect readouts of TORC2 inhibition, GSK3β(S9) and PRAS40(T246) were less potently inhibited consequent to Compound 1 treatment compared with the effect on Akt (S473). Full activation of Akt requires an additional phosphorylation on T308 that is done by PDK1 and is speculated to be co-dependent with the TORC2 phosphorylation of the Akt(S473). An indication of this is suggested by the data except possibly for HCT116 cells, but further confirmation is required. Comparison of the growth inhibitory potency of Compound 1 with the inhibition of the molecular markers for TORC1 and TORC2 activity did not appear to anticipate the loss of potency for growth inhibition in the MDA-MB231, NCI-H23 or HT-29 cells, with the possible exception of GSK3β phosphorylation status.

TABLE 1

|  | PC3 | A549 | HCT116 | U-87 MG | MDA-MB-231 | NCI-H23 | HT-29 |
|---|---|---|---|---|---|---|---|
| p-4E-BP1(T46) | 0.41 (n = 2) | 0.33 (n = 1) | 0.39 (n = 7) | 1.34 (n = 4) | 0.12 (n = 2) | 0.12 (n = 2) | 0.07 (n = 2) |
| p-S6RP(S235/S236) | 0.02 (n = 3) | 0.04 (n = 1) | 0.08 (n = 2) | 0.19 (n = 7) | 0.03 (n = 2) | 0.07 (n = 2) | 0.01 (n = 4) |
| p-Akt (S473) | 0.01 (n = 2) | 0.12 (n = 2) | 0.10 (n = 6) | 0.15 (n = 4) | 0.04 (n = 2) | 0.10 (n = 2) | 0.25 (n = 2) |
| p-GSK3β (S9) | 0.23 (n = 3) | ND | 0.22 (n = 4) | 0.28 (n = 2) | ND | >2 (n = 1) | >2 (n = 1) |
| p-PRAS40 (T246) | 0.14 (n = 4) | 0.75 (n = 1) | 0.43 (n = 6) | 0.36 (n = 2) | 0.28 (n = 1) | 0.19 (n = 2) | 0.35 (n = 2) |
| p-Akt(T308) | 0.13 (n = 2) | 0.64 (n = 1) | 1.95 (n = 1) | 0.26 (n = 1) | BLD | BLD | 0.24 (n = 1) |
| Compound 1 Growth Inhibition IC$_{50}$ | 0.11 | 0.32 | 0.37 | 0.79 | 1.77 | 3.71 | >20 |

Results

Table 2 shows the inhibition of both TORC1 and TORC2 direct and indirect substrates in the U87MG cell line (IC$_{50}$ in μM).

TABLE 2

| Cmpd No. A- | Compound Name | MSD p70S6K | Luminex p70S6K | MSD GSK-3β | Luminex GSK-3β | Luminex PRAS40 |
|---|---|---|---|---|---|---|
| 1 | 6-(6-(2-hydroxypropan-2-yl)pyridin-3-yl)-4-((tetrahydro-2H-pyran-4-yl)methyl)-3,4-dihydropyrazino[2,3-b]pyrazin-2(1H)-one | | 0.526 | | 1.22 | 1.66 |
| 2 | 1-ethyl-6-(2-methyl-6-(4H-1,2,4-triazol-3-yl)pyridin-3-yl)-1H-imidazo[4,5-b]pyrazin-2(3H)-one | | 0.433 | | | |
| 3 | 6-(6-(2-hydroxypropan-2-yl)pyridin-3-yl)-4-((1r,4r)-4-methoxycyclohexyl)-3,4-dihydropyrazino[2,3-b]pyrazin-2(1H)-one | | 0.435 | | 1.47 | 1.16 |
| 4 | 7-(2-methyl-6-(4H-1,2,4-triazol-3-yl)pyridin-3-yl)-1-(2-(tetrahydro-2H-pyran-4-yl)ethyl)-3,4-dihydropyrazino[2,3-b]pyrazin-2(1H)-one | | 0.0278 | | 0.071 | 0.098 |
| 5 | 4-(2-methoxyethyl)-6-(2-methyl-6-(4H-1,2,4-triazol-3-yl)pyridin-3-yl)-3,4-dihydropyrazino[2,3-b]pyrazin-2(1H)-one | | 0.104 | | 2.16 | 1.09 |
| 6 | 6-(4-(2-hydroxypropan-2-yl)phenyl)-4-((tetrahydro-2H-pyran-4-yl)methyl)-3,4-dihydropyrazino[2,3-b]pyrazin-2(1H)-one | | 0.162 | | 2.47 | 3.24 |
| 7 | 1-ethyl-6-(3-fluoro-2-methyl-4-(1H-1,2,4-triazol-3-yl)phenyl)-1H-imidazo[4,5-b]pyrazin-2(3H)-one | | 0.145 | | >5 | 2.85 |
| 8 | (R)-7-(6-(1-hydroxyethyl)pyridin-3-yl)-1-(2-(tetrahydro-2H-pyran-4-yl)ethyl)-3,4-dihydropyrazino[2,3-b]pyrazin-2(1H)-one | | 0.0355 | | 0.402 | 0.255 |
| 9 | 1-(2-methoxyethyl)-7-(2-methyl-6-(4H-1,2,4-triazol-3-yl)pyridin-3-yl)-3,4-dihydropyrazino[2,3-b]pyrazin-2(1H)-one | 0.268 | 0.0377 | >2 | | |
| 10 | 7-(6-(2-hydroxypropan-2-yl)pyridin-3-yl)-1-((1r,4r)-4-methoxycyclohexyl)-3,4-dihydropyrazino[2,3-b]pyrazin-2(1H)-one | | 0.103 | | 0.281 | 0.362 |
| 11 | 1-((1r,4r)-4-methoxycyclohexyl)-7-(2-methyl-6-(4H-1,2,4-triazol-3-yl)pyridin-3-yl)-3,4-dihydropyrazino[2,3-b]pyrazin-2(1H)-one | 0.0931 | | 0.479 | | |

TABLE 2-continued

| Cmpd No. A- | Compound Name | MSD p70S6K | Luminex p70S6K | MSD GSK-3β | Luminex GSK-3β | Luminex PRAS40 |
|---|---|---|---|---|---|---|
| 12 | 1-ethyl-7-(2-methyl-6-(4H-1,2,4-triazol-3-yl)pyridin-3-yl)-3,4-dihydropyrazino[2,3-b]pyrazin-2(1H)-one | 0.252 | | >2 | | |
| 13 | 1-isopropyl-7-(2-methyl-6-(4H-1,2,4-triazol-3-yl)pyridin-3-yl)-3,4-dihydropyrazino[2,3-b]pyrazin-2(1H)-one | 0.351 | | >2 | | |

Table 3 shows the values for the inhibition of both TORC1 and TORC2 direct and indirect substrates in the HCT116 cell line (IC$_{50}$ in μM).

TABLE 3

| Cmpd No. B- | Cmpd Name | MSD p70S6K (IGF) | Luminex p70S6K (IGF) | MSD GSK-3β (IGF) | Luminex GSK-3β (IGF) | Luminex PRAS40 (IGF) |
|---|---|---|---|---|---|---|
| 1 | 6-(6-(2-hydroxypropan-2-yl)pyridin-3-yl)-4-((tetrahydro-2H-pyran-4-yl)methyl)-3,4-dihydropyrazino[2,3-b]pyrazin-2(1H)-one | | 2.12 | | 1.74 | 2.61 |
| 2 | 1-ethyl-6-(2-methyl-6-(4H-1,2,4-triazol-3-yl)pyridin-3-yl)-1H-imidazo[4,5-b]pyrazin-2(3H)-one | | 1.24 | | | |
| 3 | 6-(6-(2-hydroxypropan-2-yl)pyridin-3-yl)-4-((1r,4r)-4-methoxycyclohexyl)-3,4-dihydropyrazino[2,3-b]pyrazin-2(1H)-one | | 1.82 | | 1.29 | 1.37 |
| 4 | 7-(2-methyl-6-(4H-1,2,4-triazol-3-yl)pyridin-3-yl)-1-(2-(tetrahydro-2H-pyran-4-yl)ethyl)-3,4-dihydropyrazino[2,3-b]pyrazin-2(1H)-one | | 0.0966 | | 0.0962 | 0.12 |
| 5 | 4-(2-methoxyethyl)-6-(2-methyl-6-(4H-1,2,4-triazol-3-yl)pyridin-3-yl)-3,4-dihydropyrazino[2,3-b]pyrazin-2(1H)-one | | 0.514 | | | 0.762 |
| 6 | 6-(4-(2-hydroxypropan-2-yl)phenyl)-4-((tetrahydro-2H-pyran-4-yl)methyl)-3,4-dihydropyrazino[2,3-b]pyrazin-2(1H)-one | | 0.654 | | | 0.492 |
| 7 | 1-ethyl-6-(3-fluoro-2-methyl-4-(1H-1,2,4-triazol-3-1,2,4-1H-imidazo[4,5-b]pyrazin-2(3H)-one | | 0.47 | | | 1.02 |
| 8 | (R)-7-(6-(1-hydroxyethyl)pyridin-3-yl)-1-(2-(tetrahydro-2H-pyran-4-yl)ethyl)-3,4-dihydropyrazino[2,3-b]pyrazin-2(1H)-one | | 0.091 | | | 0.16 |
| 9 | 1-(2-methoxyethyl)-7-(2-methyl-6-(4H-1,2,4-triazol-3-yl)pyridin-3-yl)-3,4-dihydropyrazino[2,3-b]pyrazin-2(1H)-one | 0.846 | 0.103 | >2 | | |
| 10 | 7-(6-(2-hydroxypropan-2-yl)pyridin-3-yl)-1-((1r,4r)-4-methoxycyclohexyl)-3,4-dihydropyrazino[2,3-b]pyrazin-2(1H)-one | | 0.191 | | 0.359 | 0.43 |
| 11 | 1-((1r,4r)-4-methoxycyclohexyl)-7-(2-methyl-6-(4H-1,2,4-triazol-3-yl)pyridin-3-yl)-3,4-dihydropyrazino[2,3-b]pyrazin-2(1H)-one | 0.157 | | 0.202 | | |
| 12 | 1-ethyl-7-(2-methyl-6-(4H-1,2,4-triazol-3-yl)pyridin-3-yl)-3,4-dihydropyrazino[2,3-b]pyrazin-2(1H)-one | 0.846 | | >2 | | |

TABLE 3-continued

| Cmpd No. B- | Cmpd Name | MSD p70S6K (IGF) | Luminex p70S6K (IGF) | MSD GSK-3β (IGF) | Luminex GSK-3β (IGF) | Luminex PRAS40 (IGF) |
|---|---|---|---|---|---|---|
| 13 | 1-isopropyl-7-(2-methyl-6-(4H-1,2,4-triazol-3-yl)pyridin-3-yl)-3,4-dihydropyrazino[2,3-b]pyrazin-2(1H)-one | 0.941 | | >2 | | |

Table 4 shows the values for the inhibition of both TORC1 and TORC2 direct and indirect substrates in the PC3 cell line ($IC_{50}$ in μM).

TABLE 4

| Cmpd No. C- | Chemical name | MSD p70S6K | Luminex p70S6K | MSD GSK-3β | Luminex GSK-3β | Luminex PRAS40 |
|---|---|---|---|---|---|---|
| 1 | 1-(cyclohexylmethyl)-6-(4-(2-hydroxypropan-2-yl)phenyl)-1H-imidazo[4,5-b]pyrazin-2(3H)-one | | 0.557 | | >1.5 | >1.5 |
| 2 | 6-(4-(1H-1,2,4-triazol-3-yl)phenyl)-1-(2-(tetrahydro-2H-pyran-4-yl)ethyl)-1H-imidazo[4,5-b]pyrazin-2(3H)-one | 0.046 | 0.030 | >1.5 | 0.255 | 0.180 |
| 3 | 6-(6-(2-hydroxypropan-2-yl)pyridin-3-yl)-1-(2-(tetrahydro-2H-pyran-4-ypethyl)-1H-imidazo[4,5-b]pyrazin-2(3H)-one | | 0.247 | | 2.594 | 1.305 |
| 4 | 6-(6-(2-hydroxypropan-2-yl)pyridin-3-yl)-4-(2-(tetrahydro-2H-pyran-4-yl)ethyl)-3,4-dihydropyrazino[2,3-b]pyrazin-2(1H)-one | | 0.134 | | 1.114 | 0.678 |
| 5 | 6-(6-(2-hydroxypropan-2-yl)pyridin-3-yl)-4-((tetrahydro-2H-pyran-4-yl)methyl)-3,4-dihydropyrazino[2,3-b]pyrazin-2(1H)-one | | 0.156 | | 0.964 | 1.751 |
| 6 | 1-ethyl-6-(2-methyl-6-(4H-1,2,4-triazol-3-yl)pyridin-3-yl)-1H-imidazo[4,5-b]pyrazin-2(3H)-one | | | | | |
| 7 | 7-(6-(2-hydroxypropan-2-yl)pyridin-3-yl)-1-(2-(tetrahydro-2H-pyran-4-yl)ethyl)-3,4-dihydropyrazino[2,3-b]pyrazin-2(1H)-one | | 0.034 | | 0.179 | 0.140 |
| 8 | 6-(6-(2-hydroxypropan-2-yl)pyridin-3-yl)-4-((1r,4r)-4-methoxycyclohexyl)-3,4-dihydropyrazino[2,3-b]pyrazin-2(1H)-one | | 0.116 | | 0.627 | 0.688 |
| 9 | 7-(2-methyl-6-(4H-1,2,4-triazol-3-yl)pyridin-3-yl)-1-(2-(tetrahydro-2H-pyran-4-yl)ethyl)-3,4-dihydropyrazino[2,3-b]pyrazin-2(1H)-one | 0.004 | 0.008 | 0.213 | 0.043 | 0.037 |
| 10 | 4-(2-methoxyethyl)-6-(2-methyl-6-(4H-1,2,4-triazol-3-yl)pyridin-3-yl)-3,4-dihydropyrazino[2,3-b]pyrazin-2(1H)-one | | 0.066 | | 1.431 | 0.624 |
| 11 | 6-(4-(2-hydroxypropan-2-yl)phenyl)-4-((tetrahydro-2H-pyran-4-yl)methyl)-3,4-dihydropyrazino[2,3-b]pyrazin-2(1H)-one | | 0.201 | | 1.166 | 0.754 |

TABLE 4-continued

| Cmpd No. C- | Chemical name | MSD p70S6K | Luminex p70S6K | MSD GSK-3β | Luminex GSK-3β | Luminex PRAS40 |
|---|---|---|---|---|---|---|
| 12 | 1-ethyl-6-(3-fluoro-2-methyl-4-(1H-1,2,4-triazol-3-yl)phenyl)-1H-imidazo[4,5-b]pyrazin-2(3H)-one | 0.436 | 0.079 | >5 | 0.936 | 1.117 |
| 13 | (R)-7-(6-(1-hydroxyethyl)pyridin-3-yl)-1-(2-(tetrahydro-2H-pyran-4-yl)ethyl)-3,4-dihydropyrazino[2,3-b]pyrazin-2(1H)-one | | | | | |
| 14 | 1-(2-methoxyethyl)-7-(2-methyl-6-(4H-1,2,4-triazol-3-yl)pyridin-3-yl)-3,4-dihydropyrazino[2,3-b]pyrazin-2(1H)-one | 0.031 | 0.010 | 0.366 | 0.366 | 0.061 |
| 15 | 7-(6-(2-hydroxypropan-2-yl)pyridin-3-yl)-1-((1r,4r)-4-methoxycyclohexyl)-3,4-dihydropyrazino[2,3-b]pyrazin-2(1H)-one | 0.082 | 0.032 | >0.5 | 0.240 | 0.096 |
| 16 | 1-((1r,4r)-4-methoxycyclohexyl)-7-(2-methyl-6-(4H-1,2,4-triazol-3-yl)pyridin-3-yl)-3,4-dihydropyrazino[2,3-b]pyrazin-2(1H)-one | 0.013 | 0.003 | 0.152 | 0.141 | 0.043 |
| 17 | 4-(cyclopropylmethyl)-6-(6-(2-hydroxypropan-2-yl)pyridin-3-yl)-3,4-dihydropyrazino[2,3-b]pyrazin-2(1H)-one | | 0.549 | | >5 | 2.899 |
| 18 | 6-(3-fluoro-4-(4H-1,2,4-triazol-3-yl)phenyl)-4-(2-(tetrahydro-2H-pyran-4-yl)ethyl)-3,4-dihydropyrazino[2,3-b]pyrazin-2(1H)-one | | 0.004 | | 0.037 | 0.027 |
| 19 | 7-(3-fluoro-2-methyl-4-(1H-1,2,4-triazol-3-yl)phenyl)-1-(2-methoxyethyl)-3,4-dihydropyrazino[2,3-b]pyrazin-2(1H)-one | | 0.006 | | 0.156 | 0.053 |
| 20 | 7-(3-fluoro-4-(4H-1,2,4-triazol-3-yl)phenyl)-1-(2-(tetrahydro-2H-pyran-4-yl)ethyl)-3,4-dihydropyrazino[2,3-b]pyrazin-2(1H)-one | | 0.006 | | >0.05 | >0.05 |
| 21 | 6-(6-(2-hydroxypropan-2-yl)pyridin-3-yl)-4-(((1S,3R)-3-methoxycyclopentyl)methyl)-3,4-dihydropyrazino[2,3-b]pyrazin-2(1H)-one | | 0.105 | | 1.684 | 0.795 |
| 22 | 6-(6-(2-hydroxypropan-2-yl)pyridin-3-yl)-4-(((1R,3S)-3-methoxycyclopentyl)methyl)-3,4-dihydropyrazino[2,3-b]pyrazin-2(1H)-one | | 0.086 | | 2.982 | 1.141 |
| 23 | 6-(6-(2-hydroxypropan-2-yl)pyridin-3-yl)-4-((1R,3R)-3-methoxycyclopentyl)-3,4-dihydropyrazino[2,3-b]pyrazin-2(1H)-one | | 0.207 | | 1.769 | 1.445 |
| 24 | 6-(6-(2-hydroxypropan-2-yl)pyridin-3-yl)-4-((1S,3S)-3-methoxycyclopentyl)-3,4-dihydropyrazino[2,3-b]pyrazin-2(1H)-one | | 0.843 | | >5 | 3.655 |
| 25 | 6-(6-(2-hydroxypropan-2-yl)pyridin-3-yl)-4-(((1R,3R)-3-methoxycyclopentyl)methyl)-3,4-dihydropyrazino[2,3-b]pyrazin-2(1H)-one | | 0.094 | | 1.777 | 0.705 |

TABLE 4-continued

| Cmpd No. C- | Chemical name | MSD p70S6K | Luminex p70S6K | MSD GSK-3β | Luminex GSK-3β | Luminex PRAS40 |
|---|---|---|---|---|---|---|
| 26 | 6-(6-(2-hydroxypropan-2-yl)pyridin-3-yl)-4-(((1S,3S)-3-methoxycyclopentyl)methyl)-3,4-dihydropyrazino[2,3-b]pyrazin-2(1H)-one | | 0.104 | | 1.431 | 0.498 |
| 27 | 7-(3-fluoro-4-(4H-1,2,4-triazol-3-yl)phenyl)-1-(2-methoxyethyl)-3,4-dihydropyrazino[2,3-b]pyrazin-2(1H)-one | | 0.008 | | 0.032 | 0.027 |
| 28 | 6-(6-(2-hydroxypropan-2-yl)pyridin-3-yl)-4-((1S,3R)-3-methoxycyclopentyl)-3,4-dihydropyrazino[2,3-b]pyrazin-2(1H)-one | | 0.452 | | >5 | 2.361 |
| 29 | 6-(6-(2-hydroxypropan-2-yl)pyridin-3-yl)-4-(((1R,3S)-3-methoxycyclopentyl)-3,4-dihydropyrazino[2,3-b]pyrazin-2(1H)-one | | 0.235 | | >5 | 2.134 |
| 30 | 3,3-dimethyl-6-(4-methyl-6-(4H-1,2,4-triazol-3-yl)pyridin-3-yl)-4-((tetrahydro-2H-pyran-4-yl)methyl)-3,4-dihydropyrazino[2,3-b]pyrazin-2(1H)-one | | 0.001 | | 0.021 | 0.005 |
| 31 | 1-benzyl-7-(2-methyl-4-(4H-1,2,4-triazol-3-yl)phenyl)-3,4-dihydropyrazino[2,3-b]pyrazin-2(1H)-one | | 0.002 | | >5 | 0.014 |
| 32 | 6-(3-fluoro-2-methyl-4-(4H-1,2,4-triazol-3-yl)phenyl)-4-(2-methoxyethyl)-3,4-dihydropyrazino[2,3-b]pyrazin-2(1H)-one | | 0.012 | | 0.169 | 0.059 |
| 33 | 1-(2-methoxyethyl)-7-(4-methyl-6-(1H-1,2,4-triazol-3-yl)pyridin-3-yl)-3,4-dihydropyrazino[2,3-b]pyrazin-2(1H)-one | | 0.001 | | 0.081 | |
| 34 | 6-(3-fluoro-2-methyl-4-(4H-1,2,4-triazol-3-yl)phenyl)-4-(2-(tetrahydro-2H-pyran-4-yl)ethyl)-3,4-dihydropyrazino[2,3-b]pyrazin-2(1H)-one | | 0.021 | | >5 | 1.519 |
| 35 | 7-(2-methyl-4-(4H-1,2,4-triazol-3-yl)phenyl)-3,4-dihydropyrazino[2,3-b]pyrazin-2(1H)-one | | 0.815 | | | |
| 36 | 4-(((1S,3R)-3-methoxycyclopentyl)methyl)-6-(2-methyl-6-(4H-1,2,4-triazol-3-yl)pyridin-3-yl)-3,4-dihydropyrazino[2,3-b]pyrazin-2(1H)-one | | 0.016 | | | |
| 37 | 4-(((1R,3S)-3-methoxycyclopentyl)methyl)-6-(2-methyl-6-(4H-1,2,4-triazol-3-yl)pyridin-3-yl)-3,4-dihydropyrazino[2,3-b]pyrazin-2(1H)-one | | 0.024 | | | |
| 38 | 7-(7-methyl-2-oxo-2,3-dihydro-1H-benzo[d]imidazol-5-yl)-1-((tetrahydro-2H-pyran-4-yl)methyl)-3,4-dihydropyrazino[2,3-b]pyrazin-2(1H)-one | | 4.999 | | >5 | 3.250 |
| 39 | 1-(2-methoxyethyl)-7-(4-methyl-2-(methylamino)-1H-benzo[d]imidazol-6-yl)-3,4-dihydropyrazino[2,3-b]pyrazin-2(1H)-one | | 0.283 | | >5 | 1.405 |

TABLE 4-continued

| Cmpd No. C- | Chemical name | MSD p70S6K | Luminex p70S6K | MSD GSK-3β | Luminex GSK-3β | Luminex PRAS40 |
|---|---|---|---|---|---|---|
| 40 | 6-(1H-indol-5-yl)-4-(2-(tetrahydro-2H-pyran-4-yl)ethyl)-3,4-dihydropyrazino[2,3-b]pyrazin-2(1H)-one | | 1.522 | | >5 | >5 |
| 41 | 6-(1H-indol-6-yl)-4-(2-(tetrahydro-2H-pyran-4-yl)ethyl)-3,4-dihydropyrazino[2,3-b]pyrazin-2(1H)-one | | 0.746 | | 3.184 | 4.996 |
| 42 | 7-(6-(2-hydroxypropan-2-yl)pyridin-3-yl)-1-(((1s,4s)-4-methoxycyclohexyl)methyl)-3,4-dihydropyrazino[2,3-b]pyrazin-2(1H)-one | | 0.016 | | 0.268 | 0.044 |
| 43 | 1-(2-methoxyethyl)-6-(1H-pyrrolo[2,3-b]pyridin-5-yl)-1H-imidazo[4,5-b]pyrazin-2(3H)-one | | 0.201 | | 0.214 | 0.524 |
| 44 | 6-(1H-pyrrolo[2,3-b]pyridin-5-yl)-4-(2-(tetrahydro-2H-pyran-4-yl)ethyl)-3,4-dihydropyrazino[2,3-b]pyrazin-2(1H)-one | | 0.017 | | 0.313 | 0.098 |
| 45 | 4-ethyl-6-(2-methyl-6-(4H-1,2,4-triazol-3-yl)pyridin-3-yl)-3,4-dihydropyrazino[2,3-b]pyrazin-2(1H)-one | | 0.053 | | 0.738 | 1.093 |
| 46 | 1-(((1r,4r)-4-methoxycyclohexyl)methyl)-7-(2-methyl-6-(1H-1,2,4-triazol-3-yl)pyridin-3-yl)-3,4-dihydropyrazino[2,3-b]pyrazin-2(1H)-one | | 0.027 | | 0.218 | 0.144 |
| 47 | 7-(6-(2-hydroxypropan-2-yl)pyridin-3-yl)-1-(tetrahydro-2H-pyran-4-yl)-3,4-dihydropyrazino[2,3-b]pyrazin-2(1H)-one | | 0.497 | | 3.110 | 1.466 |
| 48 | 7-(4-(2-hydroxypropan-2-yl)phenyl)-1-((1r,4r)-4-methoxycyclohexyl)-3,4-dihydropyrazino[2,3-b]pyrazin-2(1H)-one | | 0.080 | | 0.502 | 0.415 |
| 49 | 7-(1H-indol-6-yl)-1-(2-(tetrahydro-2H-pyran-4-yl)ethyl)-3,4-dihydropyrazino[2,3-b]pyrazin-2(1H)-one | | 0.468 | | 3.844 | 1.992 |
| 50 | 4-((1S,3S)-3-methoxycyclopentyl)-6-(2-methyl-6-(4H-1,2,4-triazol-3-yl)pyridin-3-yl)-3,4-dihydropyrazino[2,3-b]pyrazin-2(1H)-one | | 0.048 | | >0.5 | >0.5 |
| 51 | 4-((1R,3R)-3-methoxycyclopentyl)-6-(2-methyl-6-(4H-1,2,4-triazol-3-yl)pyridin-3-yl)-3,4-dihydropyrazino[2,3-b]pyrazin-2(1H)-one | | 0.046 | | 0.859 | 0.816 |
| 52 | 4-((1S,3R)-3-methoxycyclopentyl)-6-(2-methyl-6-(4H-1,2,4-triazol-3-yl)pyridin-3-yl)-3,4-dihydropyrazino[2,3-b]pyrazin-2(1H)-one | | 0.088 | | 1.103 | 0.960 |
| 53 | 4-((1R,3S)-3-methoxycyclopentyl)-6-(2-methyl-6-(4H-1,2,4-triazol-3-yl)pyridin-3-yl)-3,4-dihydropyrazino[2,3-b]pyrazin-2(1H)-one | | 0.232 | | 1.139 | 1.158 |

TABLE 4-continued

| Cmpd No. C- | Chemical name | MSD p70S6K | Luminex p70S6K | MSD GSK-3β | Luminex GSK-3β | Luminex PRAS40 |
|---|---|---|---|---|---|---|
| 54 | 1-ethyl-7-(2-methyl-6-(4H-1,2,4-triazol-3-yl)pyridin-3-yl)-3,4-dihydropyrazino[2,3-b]pyrazin-2(1H)-one | 0.031 | 0.013 | 0.181 | 0.370 | 0.039 |
| 55 | 7-(1H-indol-5-yl)-1-(2-(tetrahydro-2H-pyran-4-yl)ethyl)-3,4-dihydropyrazino[2,3-b]pyrazin-2(1H)-one | | 0.025 | | 0.341 | 0.228 |
| 56 | 1-((1S,3S)-3-methoxycyclopentyl)-7-(2-methyl-6-(4H-1,2,4-triazol-3-yl)pyridin-3-yl)-3,4-dihydropyrazino[2,3-b]pyrazin-2(1H)-one | | 0.045 | | 0.269 | 0.113 |
| 57 | 1-((1R,3S)-3-methoxycyclopentyl)-7-(2-methyl-6-(4H-1,2,4-triazol-3-yl)pyridin-3-yl)-3,4-dihydropyrazino[2,3-b]pyrazin-2(1H)-one | | 0.006 | | 0.170 | 0.123 |
| 58 | 1-((1R,3R)-3-methoxycyclopentyl)-7-(2-methyl-6-(4H-1,2,4-triazol-3-yl)pyridin-3-yl)-3,4-dihydropyrazino[2,3-b]pyrazin-2(1H)-one | | 0.048 | | 0.507 | 0.209 |
| 59 | 1-((1S,3R)-3-methoxycyclopentyl)-7-(2-methyl-6-(4H-1,2,4-triazol-3-yl)pyridin-3-yl)-3,4-dihydropyrazino[2,3-b]pyrazin-2(1H)-one | | 0.028 | | 0.126 | 0.099 |
| 60 | 7-(2-methyl-6-(4H-1,2,4-triazol-3-yl)pyridin-3-yl)-1-(tetrahydro-2H-pyran-4-yl)-3,4-dihydropyrazino[2,3-b]pyrazin-2(1H)-one | | 0.010 | | 0.058 | 0.055 |
| 61 | 7-(1H-pyrrolo[2,3-b]pyridin-5-yl)-1-(2-(tetrahydro-2H-pyran-4-yl)ethyl)-3,4-dihydropyrazino[2,3-b]pyrazin-2(1H)-one | | 0.003 | | 0.033 | 0.021 |
| 62 | 7-(1H-indazol-5-yl)-1-(2-(tetrahydro-2H-pyran-4-yl)ethyl)-3,4-dihydropyrazino[2,3-b]pyrazin-2(1H)-one | | 0.033 | | 0.568 | 0.349 |
| 63 | 4-(7-oxo-8-(2-(tetrahydro-2H-pyran-4-yl)ethyl)-5,6,7,8-tetrahydropyrazino[2,3-b]pyrazin-2-yl)benzamide | | 0.216 | | 0.927 | 0.842 |
| 64 | 1-((1s,4s)-4-hydroxycyclohexyl)-7-(6-(2-hydroxypropan-2-yl)pyridin-3-yl)-3,4-dihydropyrazino[2,3-b]pyrazin-2(1H)-one | | 0.061 | | 0.299 | 0.349 |
| 65 | 1-((1r,4r)-4-hydroxycyclohexyl)-7-(6-(2-hydroxypropan-2-yl)pyridin-3-yl)-3,4-dihydropyrazino[2,3-b]pyrazin-2(1H)-one | | 0.040 | | 0.266 | 0.207 |
| 66 | 1-(((1s,4s)-4-methoxycyclohexyl)methyl)-7-(2-methyl-6-(1H-1,2,4-triazol-3-yl)pyridin-3-yl)-3,4-dihydropyrazino[2,3-b]pyrazin-2(1H)-one | | 0.004 | | 0.015 | 0.012 |
| 67 | 7-(1H-imidazo[4,5-b]pyridin-6-yl)-1-(2-(tetrahydro-2H-pyran-4-yl)ethyl)-3,4-dihydropyrazino[2,3-b]pyrazin-2(1H)-one | | >1.5 | | >1.5 | >1.5 |

TABLE 4-continued

| Cmpd No. C- | Chemical name | MSD p70S6K | Luminex p70S6K | MSD GSK-3β | Luminex GSK-3β | Luminex PRAS40 |
|---|---|---|---|---|---|---|
| 68 | 6-(1H-indazol-6-yl)-4-(2-(tetrahydro-2H-pyran-4-yl)ethyl)-3,4-dihydropyrazino[2,3-b]pyrazin-2(1H)-one | | 0.752 | | >1.5 | >1.5 |
| 69 | 1-isopropyl-7-(2-methyl-6-(4H-1,2,4-triazol-3-yl)pyridin-3-yl)-3,4-dihydropyrazino[2,3-b]pyrazin-2(1H)-one | 0.080 | 0.031 | 0.394 | 0.342 | 0.285 |
| 70 | 7-(6-(2-hydroxypropan-2-yl)pyridin-3-yl)-1-(2-morpholinoethyl)-3,4-dihydropyrazino[2,3-b]pyrazin-2(1H)-one | | 0.540 | | 0.700 | >1.5 |
| 71 | 1-((1s,4s)-4-hydroxycyclohexyl)-7-(2-methyl-6-(4H-1,2,4-triazol-3-yl)pyridin-3-yl)-3,4-dihydropyrazino[2,3-b]pyrazin-2(1H)-one | | 0.006 | | 0.040 | 0.037 |
| 72 | 1-((1r,4r)-4-hydroxycyclohexyl)-7-(2-methyl-6-(4H-1,2,4-triazol-3-yl)pyridin-3-yl)-3,4-dihydropyrazino[2,3-b]pyrazin-2(1H)-one | | 0.012 | | 0.310 | 0.105 |
| 73 | 7-(2-methyl-6-(4H-1,2,4-triazol-3-yl)pyridin-3-yl)-1-(2-morpholinoethyl)-3,4-dihydropyrazino[2,3-b]pyrazin-2(1H)-one | | 0.054 | | 0.671 | 0.261 |
| 74 | 6-(1H-imidazo[4,5-b]pyridin-6-yl)-4-(2-(tetrahydro-2H-pyran-4-yl)ethyl)-3,4-dihydropyrazino[2,3-b]pyrazin-2(1H)-one | | >1.5 | | >1.5 | >1.5 |
| 75 | 7-(1H-indazol-6-yl)-1-(2-(tetrahydro-2H-pyran-4-yl)ethyl)-3,4-dihydropyrazino[2,3-b]pyrazin-2(1H)-one | | 0.173 | | >1.5 | >1.5 |
| 76 | 6-(6-(3-hydroxyoxetan-3-yl)pyridin-3-yl)-1-(2-(tetrahydro-2H-pyran-4-ypethyl)-1H-imidazo[4,5-b]pyrazin-2(3H)-one | | >1.5 | | >1.5 | >1.5 |
| 77 | 6-(5-(3-hydroxyoxetan-3-yl)pyridin-2-yl)-1-(2-(tetrahydro-2H-pyran-4-ypethyl)-1H-imidazo[4,5-b]pyrazin-2(3H)-one | | >1.5 | | >1.5 | >1.5 |
| 78 | 7-(6-(2-hydroxypropan-2-yl)pyridin-3-yl)-1-((1R,3S)-3-methoxycyclopentyl)-3,4-dihydropyrazino[2,3-b]pyrazin-2(1H)-one | | 1.287 | | >1.5 | >1.5 |
| 79 | 7-(6-(2-hydroxypropan-2-yl)pyridin-3-yl)-1-((1S,3S)-3-methoxycyclopentyl)-3,4-dihydropyrazino[2,3-b]pyrazin-2(1H)-one | | 0.981 | | >1.5 | >1.5 |
| 80 | 7-(6-(2-hydroxypropan-2-yl)pyridin-3-yl)-1-((1S,3R)-3-methoxycyclopentyl)-3,4-dihydropyrazino[2,3-b]pyrazin-2(1H)-one | | 0.133 | | 0.841 | 0.724 |
| 81 | 7-(6-(2-hydroxypropan-2-yl)pyridin-3-yl)-1-((1R,3R)-3-methoxycyclopentyl)-3,4-dihydropyrazino[2,3-b]pyrazin-2(1H)-one | | 0.134 | | >1.5 | 0.847 |

TABLE 4-continued

| Cmpd No. C- | Chemical name | MSD p70S6K | Luminex p70S6K | MSD GSK-3β | Luminex GSK-3β | Luminex PRAS40 |
|---|---|---|---|---|---|---|
| 82 | 5-(8-((1r,4r)-4-methoxycyclohexyl)-6-oxo-5,6,7,8-tetrahydropyrazino[2,3-b]pyrazin-2-yl)-4-methylpicolinamide | | 0.467 | | >1.5 | >1.5 |
| 83 | 3-(6-oxo-8-(2-(tetrahydro-2H-pyran-4-yl)ethyl)-5,6,7,8-tetrahydropyrazino[2,3-b]pyrazin-2-yl)benzonitrile | | >1.5 | | >1.5 | >1.5 |
| 84 | 3-(6-oxo-8-(2-(tetrahydro-2H-pyran-4-yl)ethyl)-5,6,7,8-tetrahydropyrazino[2,3-b]pyrazin-2-yl)benzamide | | >1.5 | | >1.5 | >1.5 |
| 85 | 3-((7-(6-(2-hydroxypropan-2-yl)pyridin-3-yl)-2-oxo-3,4-dihydropyrazino[2,3-b]pyrazin-1(2H)-yl)methyl)benzonitrile | | 0.027 | | 0.030 | 0.139 |
| 86 | 5-(8-(2-methoxyethyl)-6-oxo-5,6,7,8-tetrahydropyrazino[2,3-b]pyrazin-2-yl)-4-methylpicolinamide | | 0.310 | | 0.939 | >1.5 |
| 87 | 6-(3-(1H-1,2,4-triazol-5-yl)phenyl)-4-(2-(tetrahydro-2H-pyran-4-yl)ethyl)-3,4-dihydropyrazino[2,3-b]pyrazin-2(1H)-one | | 0.910 | | >1.5 | >1.5 |
| 88 | 4-(2-methoxyethyl)-6-(4-methyl-6-(1H-1,2,4-triazol-3-yl)pyridin-3-yl)-3,4-dihydropyrazino[2,3-b]pyrazin-2(1H)-one | | 0.003 | | 0.008 | 0.023 |
| 89 | 5-(8-(((1r,4r)-4-methoxycyclohexyl)methyl)-7-oxo-5,6,7,8-tetrahydropyrazino[2,3-b]pyrazin-2-yl)-4-methylpicolinamide | | 0.102 | | 0.860 | 1.013 |
| 90 | 3-(7-oxo-8-(2-(tetrahydro-2H-pyran-4-yl)ethyl)-5,6,7,8-tetrahydropyrazino[2,3-b]pyrazin-2-yl)benzamide | | 1.328 | | >1.5 | >1.5 |
| 91 | 1-(((1r,4r)-4-methoxycyclohexyl)methyl)-7-(4-methyl-6-(1H-1,2,4-triazol-3-yl)pyridin-3-yl)-3,4-dihydropyrazino[2,3-b]pyrazin-2(1H)-one | | 0.002 | | 0.004 | 0.007 |
| 92 | 3-((7-(2-methyl-6-(4H-1,2,4-triazol-3-yl)pyridin-3-yl)-2-oxo-3,4-dihydropyrazino[2,3-b]pyrazin-1(2H)-yl)methyl)benzonitrile | | 0.001 | | 0.008 | 0.009 |
| 93 | 1-((1r,4r)-4-methoxycyclohexyl)-7-(4-methyl-6-(1H-1,2,4-triazol-3-yl)pyridin-3-yl)-3,4-dihydropyrazino[2,3-b]pyrazin-2(1H)-one | 0.001 | 0.000 | >0.0015 | 0.002 | 0.000 |
| 94 | 7-(1H-pyrazol-4-yl)-1-(2-(tetrahydro-2H-pyran-4-yl)ethyl)-3,4-dihydropyrazino[2,3-b]pyrazin-2(1H)-one | | 0.209 | | >1.5 | >1.5 |
| 95 | 5-(8-(((1s,4s)-4-methoxycyclohexyl)methyl)-7-oxo-5,6,7,8-tetrahydropyrazino[2,3-b]pyrazin-2-yl)-4-methylpicolinamide | | 0.029 | | 0.234 | 0.308 |

TABLE 4-continued

| Cmpd No. C- | Chemical name | MSD p70S6K | Luminex p70S6K | MSD GSK-3β | Luminex GSK-3β | Luminex PRAS40 |
|---|---|---|---|---|---|---|
| 96 | 4-methyl-5-(7-oxo-8-((tetrahydro-2H-pyran-4-yl)methyl)-5,6,7,8-tetrahydropyrazino[2,3-b]pyrazin-2-yl)picolinamide | | 0.129 | | 0.721 | 0.919 |
| 97 | 1-ethyl-7-(1H-indazol-6-yl)-3,4-dihydropyrazino[2,3-b]pyrazin-2(1H)-one | | >1.5 | | >1.5 | >1.5 |
| 98 | 2-(2-hydroxypropan-2-yl)-5-(8-((1r,4r)-4-methoxycyclohexyl)-7-oxo-5,6,7,8-tetrahydropyrazino[2,3-b]pyrazin-2-yl)pyridine 1-oxide | | 0.825 | | >1.5 | >1.5 |
| 99 | 1-methyl-7-(2-methyl-6-(4H-1,2,4-triazol-3-yl)pyridin-3-yl)-3,4-dihydropyrazino[2,3-b]pyrazin-2(1H)-one | | 0.011 | | 0.348 | 0.274 |
| 100 | 7-(6-aminopyridin-3-yl)-1-(2-(tetrahydro-2H-pyran-4-yl)ethyl)-3,4-dihydropyrazino[2,3-b]pyrazin-2(1H)-one | | 0.015 | | 0.608 | 0.564 |
| 101 | 7-(pyridin-4-yl)-1-(2-(tetrahydro-2H-pyran-4-yl)ethyl)-3,4-dihydropyrazino[2,3-b]pyrazin-2(1H)-one | | 0.469 | | >1.5 | >1.5 |
| 102 | 1-ethyl-7-(1H-indazol-4-yl)-3,4-dihydropyrazino[2,3-b]pyrazin-2(1H)-one | | >1.5 | | >1.5 | >1.5 |
| 103 | 1-ethyl-7-(1H-pyrrolo[2,3-b]pyridin-5-yl)-3,4-dihydropyrazino[2,3-b]pyrazin-2(1H)-one | >0.5 | 0.150 | >0.5 | 0.153 | 0.696 |
| 104 | 1-(2-methoxyethyl)-7-(1H-pyrrolo[2,3-b]pyridin-5-yl)-3,4-dihydropyrazino[2,3-b]pyrazin-2(1H)-one | | <0.0015 | | 0.168 | 0.106 |
| 105 | 7-(6-methoxypyridin-3-yl)-1-(2-(tetrahydro-2H-pyran-4-yl)ethyl)-3,4-dihydropyrazino[2,3-b]pyrazin-2(1H)-one | | 0.252 | | >1.5 | >1.5 |
| 106 | 7-(pyrimidin-5-yl)-1-(2-(tetrahydro-2H-pyran-4-yl)ethyl)-3,4-dihydropyrazino[2,3-b]pyrazin-2(1H)-one | | >1.5 | | >1.5 | >1.5 |
| 107 | 7-(1H-indazol-6-yl)-1-(2-methoxyethyl)-3,4-dihydropyrazino[2,3-b]pyrazin-2(1H)-one | | 0.143 | | >1.5 | >1.5 |
| 108 | 6-(3-fluoro-2-methyl-4-(1H-1,2,4-triazol-3-yl)phenyl)-4-((1r,4r)-4-methoxycyclohexyl)-3,4-dihydropyrazino[2,3-b]pyrazin-2(1H)-one | | 0.005 | | 0.037 | 0.031 |
| 109 | 7-(1H-indazol-4-yl)-1-(2-methoxyethyl)-3,4-dihydropyrazino[2,3-b]pyrazin-2(1H)-one | | 0.367 | | >1.5 | >1.5 |
| 110 | 6-(3-fluoro-2-methyl-4-(1H-1,2,4-triazol-3-yl)phenyl)-4-((1s,4s)-4-methoxycyclohexyl)-3,4-dihydropyrazino[2,3-b]pyrazin-2(1H)-one | 0.022 | | >0.15 | | |
| 111 | 6-(3-fluoro-2-methyl-4-(1H-1,2,4-triazol-3-yl)phenyl)-4-(tetrahydro-2H-pyran-4-yl)-3,4-dihydropyrazino[2,3-b]pyrazin-2(1H)-one | 0.058 | | >0.15 | | |

TABLE 4-continued

| Cmpd No. C- | Chemical name | MSD p70S6K | Luminex p70S6K | MSD GSK-3β | Luminex GSK-3β | Luminex PRAS40 |
|---|---|---|---|---|---|---|
| 112 | 7-(4-(1H-pyrazol-3-yl)phenyl)-1-(2-methoxyethyl)-3,4-dihydropyrazino[2,3-b]pyrazin-2(1H)-one | 0.036 | | >0.5 | | |
| 113 | 7-(6-hydroxypyridin-3-yl)-1-(2-(tetrahydro-2H-pyran-4-yl)ethyl)-3,4-dihydropyrazino[2,3-b]pyrazin-2(1H)-one | >0.5 | | >0.5 | | |
| 114 | 7-(6-(methylamino)pyridin-3-yl)-1-(2-(tetrahydro-2H-pyran-4-yl)ethyl)-3,4-dihydropyrazino[2,3-b]pyrazin-2(1H)-one | 0.184 | | 2.026 | | |
| 115 | 7-(2-aminopyridin-4-yl)-1-(2-(tetrahydro-2H-pyran-4-yl)ethyl)-3,4-dihydropyrazino[2,3-b]pyrazin-2(1H)-one | >0.5 | | >0.5 | | |
| 116 | 7-(2-aminopyrimidin-5-yl)-1-(2-(tetrahydro-2H-pyran-4-yl)ethyl)-3,4-dihydropyrazino[2,3-b]pyrazin-2(1H)-one | 0.303 | | 3.990 | | |
| 117 | 7-(1H-indazol-4-yl)-1-(2-(tetrahydro-2H-pyran-4-yl)ethyl)-3,4-dihydropyrazino[2,3-b]pyrazin-2(1H)-one | >5 | | >5 | | |
| 118 | 5-(8-isopropyl-7-oxo-5,6,7,8-tetrahydropyrazino[2,3-b]pyrazin-2-yl)-4-methylpicolinamide | 0.170 | | 3.930 | | |
| 119 | 4-ethyl-6-(5-fluoro-2-methyl-4-(1H-1,2,4-triazol-3-yl)phenyl)-3,4-dihydropyrazino[2,3-b]pyrazin-2(1H)-one | 0.010 | | 0.323 | | |
| 120 | 6-(5-fluoro-2-methyl-4-(1H-1,2,4-triazol-3-yl)phenyl)-4-isopropyl-3,4-dihydropyrazino[2,3-b]pyrazin-2(1H)-one | 0.012 | | 0.099 | | |
| 121 | 1-isopropyl-7-(4-methyl-6-(1H-1,2,4-triazol-3-yl)pyridin-3-yl)-3,4-dihydropyrazino[2,3-b]pyrazin-2(1H)-one | 0.000 | | 0.015 | | |
| 122 | 6-(5-fluoro-2-methyl-4-(1H-1,2,4-triazol-3-yl)phenyl)-4-(tetrahydro-2H-pyran-4-yl)-3,4-dihydropyrazino[2,3-b]pyrazin-2(1H)-one | 0.006 | | 0.323 | | |
| 123 | 6-(5-fluoro-2-methyl-4-(1H-1,2,4-triazol-3-yl)phenyl)-4-((1r,4r)-4-hydroxycyclohexyl)-3,4-dihydropyrazino[2,3-b]pyrazin-2(1H)-one | 0.013 | | >0.5 | | |
| 124 | 6-(6-(1H-1,2,4-triazol-3-yl)pyridin-3-yl)-4-ethyl-3,4-dihydropyrazino[2,3-b]pyrazin-2(1H)-one | 0.289 | | >0.5 | | |
| 125 | 6-(6-(1H-1,2,4-triazol-3-yl)pyridin-3-yl)-4-(tetrahydro-2H-pyran-4-yl)-3,4-dihydropyrazino[2,3-b]pyrazin-2(1H)-one | 0.073 | | >0.5 | | |
| 126 | 7-(2-hydroxypyridin-4-yl)-1-(2-(tetrahydro-2H-pyran-4-yl)ethyl)-3,4-dihydropyrazino[2,3-b]pyrazin-2(1H)-one | 0.480 | | 1.141 | | |
| 127 | 1-ethyl-7-(5-fluoro-2-methyl-4-(1H-1,2,4-triazol-3- | 0.004 | | 0.033 | | |

TABLE 4-continued

| Cmpd No. C- | Chemical name | MSD p70S6K | Luminex p70S6K | MSD GSK-3β | Luminex GSK-3β | Luminex PRAS40 |
|---|---|---|---|---|---|---|
| | yl)phenyl)-3,4-dihydropyrazino[2,3-b]pyrazin-2(1H)-one | | | | | |
| 128 | 7-(5-fluoro-2-methyl-4-(1H-1,2,4-triazol-3-yl)phenyl)-1-isopropyl-3,4-dihydropyrazino[2,3-b]pyrazin-2(1H)-one | 0.021 | | 0.001 | | |
| 129 | 7-(5-fluoro-2-methyl-4-(1H-1,2,4-triazol-3-yl)phenyl)-1-(2-methoxyethyl)-3,4-dihydropyrazino[2,3-b]pyrazin-2(1H)-one | 0.001 | | >0.5 | | |
| 130 | 7-(5-fluoro-2-methyl-4-(1H-1,2,4-triazol-3-yl)phenyl)-1-((1r,4r)-4-hydroxycyclohexyl)-3,4-dihydropyrazino[2,3-b]pyrazin-2(1H)-one | <0.000835 | | 0.012 | | |
| 131 | 6-(5-fluoro-2-methyl-4-(1H-1,2,4-triazol-3-yl)phenyl)-4-(2-methoxyethyl)-3,4-dihydropyrazino[2,3-b]pyrazin-2(1H)-one | 0.118 | | >0.5 | | |
| 132 | 6-(5-fluoro-2-methyl-4-(1H-1,2,4-triazol-3-yl)phenyl)-4-((1s,4s)-4-methoxycyclohexyl)-3,4-dihydropyrazino[2,3-b]pyrazin-2(1H)-one | 0.222 | | >0.5 | | |
| 133 | 6-(5-fluoro-2-methyl-4-(1H-1,2,4-triazol-3-yl)phenyl)-4-((1s,4s)-4-hydroxycyclohexyl)-3,4-dihydropyrazino[2,3-b]pyrazin-2(1H)-one | 0.061 | | >0.5 | | |
| 134 | 6-(6-(1H-1,2,4-triazol-3-yl)pyridin-3-yl)-4-isopropyl-3,4-dihydropyrazino[2,3-b]pyrazin-2(1H)-one | 0.172 | | >0.5 | | |
| 135 | 6-(6-(1H-1,2,4-triazol-3-yl)pyridin-3-yl)-4-(2-methoxyethyl)-3,4-dihydropyrazino[2,3-b]pyrazin-2(1H)-one | >1.5 | | >1.5 | | |
| 136 | 6-(6-(1H-1,2,4-triazol-3-yl)pyridin-3-yl)-4-((1s,4s)-4-methoxycyclohexyl)-3,4-dihydropyrazino[2,3-b]pyrazin-2(1H)-one | 0.082 | | >0.5 | | |
| 137 | 7-(5-fluoro-2-methyl-4-(1H-1,2,4-triazol-3-yl)phenyl)-1-((1r,4r)-4-methoxycyclohexyl)-3,4-dihydropyrazino[2,3-b]pyrazin-2(1H)-one | 0.052 | | 0.394 | | |
| 138 | 7-(6-(1H-1,2,4-triazol-3-yl)pyridin-3-yl)-1-isopropyl-3,4-dihydropyrazino[2,3-b]pyrazin-2(1H)-one | 0.040 | | 0.181 | | |
| 139 | 7-(6-(1H-1,2,4-triazol-3-yl)pyridin-3-yl)-1-((1r,4r)-4-methoxycyclohexyl)-3,4-dihydropyrazino[2,3-b]pyrazin-2(1H)-one | 0.040 | | >0.5 | | |
| 140 | 7-(6-(1H-1,2,4-triazol-3-yl)pyridin-3-yl)-1-((1r,4r)-4-hydroxycyclohexyl)-3,4-dihydropyrazino[2,3-b]pyrazin-2(1H)-one | 0.070 | | >0.5 | | |
| 141 | 7-(6-(1H-1,2,4-triazol-3-yl)pyridin-3-yl)-1-(((1s,4s)-4-hydroxycyclohexyl)methyl)-3,4-dihydropyrazino[2,3-b]pyrazin-2(1H)-one | 0.042 | | | | |

TABLE 4-continued

| Cmpd No. C- | Chemical name | MSD p70S6K | Luminex p70S6K | MSD GSK-3β | Luminex GSK-3β | Luminex PRAS40 |
|---|---|---|---|---|---|---|
| 142 | 7-(5-fluoro-2-methyl-4-(1H-1,2,4-triazol-3-yl)phenyl)-1-(((1r,4r)-4-hydroxycyclohexyl)methyl)-3,4-dihydropyrazino[2,3-b]pyrazin-2(1H)-one | 0.018 | | >0.5 | | |
| 143 | 6-(5-fluoro-2-methyl-4-(1H-1,2,4-triazol-3-yl)phenyl)-4-(((1s,4s)-4-hydroxycyclohexyl)methyl)-3,4-dihydropyrazino[2,3-b]pyrazin-2(1H)-one | 0.004 | | >0.5 | | |
| 144 | 6-(6-(1H-1,2,4-triazol-3-yl)pyridin-3-yl)-4-((1r,4r)-4-hydroxycyclohexyl)-3,4-dihydropyrazino[2,3-b]pyrazin-2(1H)-one | >0.5 | | >0.5 | | |
| 145 | 7-(1H-indol-4-yl)-1-(2-(tetrahydro-2H-pyran-4-yl)ethyl)-3,4-dihydropyrazino[2,3-b]pyrazin-2(1H)-one | >0.5 | | >0.5 | | |
| 146 | 6-(6-(1H-1,2,4-triazol-3-yl)pyridin-3-yl)-4-((1r,4r)-4-methoxycyclohexyl)-3,4-dihydropyrazino[2,3-b]pyrazin-2(1H)-one | 0.012 | | >0.5 | | |
| 147 | 7-(5-fluoro-2-methyl-4-(1H-1,2,4-triazol-3-yl)phenyl)-1-(((1s,4s)-4-hydroxycyclohexyl)methyl)-3,4-dihydropyrazino[2,3-b]pyrazin-2(1H)-one | <0.0015 | | >0.5 | | |
| 148 | 6-(5-fluoro-2-methyl-4-(1H-1,2,4-triazol-3-yl)phenyl)-4-((1r,4r)-4-methoxycyclohexyl)-3,4-dihydropyrazino[2,3-b]pyrazin-2(1H)-one | <0.0015 | | 0.065 | | |
| 149 | 6-(6-(1H-1,2,4-triazol-3-yl)pyridin-3-yl)-4-(((1s,4s)-4-hydroxycyclohexyl)methyl)-3,4-dihydropyrazino[2,3-b]pyrazin-2(1H)-one | 0.173 | | >5 | | |
| 150 | 7-(6-(1H-1,2,4-triazol-3-yl)pyridin-3-yl)-1-ethyl-3,4-dihydropyrazino[2,3-b]pyrazin-2(1H)-one | 0.038 | | >0.5 | | |
| 151 | 7-(6-(1H-1,2,4-triazol-3-yl)pyridin-3-yl)-1-(2-methoxyethyl)-3,4-dihydropyrazino[2,3-b]pyrazin-2(1H)-one | 0.120 | | >0.5 | | |
| 152 | 7-(6-(1H-1,2,4-triazol-3-yl)pyridin-3-yl)-1-(tetrahydro-2H-pyran-4-yl)-3,4-dihydropyrazino[2,3-b]pyrazin-2(1H)-one | 0.020 | | >0.5 | | |
| 153 | 6-(6-(1H-1,2,4-triazol-3-yl)pyridin-3-yl)-4-((1s,4s)-4-hydroxycyclohexyl)-3,4-dihydropyrazino[2,3-b]pyrazin-2(1H)-one | >0.5 | | >0.5 | | |
| 154 | 6-(6-(1H-1,2,4-triazol-3-yl)pyridin-3-yl)-4-(((1r,4r)-4-hydroxycyclohexyl)methyl)-3,4-dihydropyrazino[2,3-b]pyrazin-2(1H)-one | 1.515 | | >5 | | |
| 155 | 7-(5-fluoro-2-methyl-4-(1H-1,2,4-triazol-3-yl)phenyl)-1-(((1s,4s)-4-hydroxycyclohexyl)methyl)-3,4-dihydropyrazino[2,3-b]pyrazin-2(1H)-one | 0.040 | | 0.240 | | |

TABLE 4-continued

| Cmpd No. C- | Chemical name | MSD p70S6K | Luminex p70S6K | MSD GSK-3β | Luminex GSK-3β | Luminex PRAS40 |
|---|---|---|---|---|---|---|
| 156 | 6-(6-(1H-1,2,4-triazol-3-yl)pyridin-3-yl)-4-(((1s,4s)-4-methoxycyclohexyl)methyl)-3,4-dihydropyrazino[2,3-b]pyrazin-2(1H)-one | 0.010 | | | | |
| 157 | 6-(5-fluoro-2-methyl-4-(1H-1,2,4-triazol-3-yl)phenyl)-4-(((1r,4r)-4-hydroxycyclohexyl)methyl)-3,4-dihydropyrazino[2,3-b]pyrazin-2(1H)-one | 0.037 | | | | |
| 158 | 6-(6-(1H-1,2,4-triazol-3-yl)pyridin-3-yl)-4-(((1r,4r)-4-methoxycyclohexyl)methyl)-3,4-dihydropyrazino[2,3-b]pyrazin-2(1H)-one | 0.036 | | | | |
| 159 | 7-(6-(1H-1,2,4-triazol-3-yl)pyridin-3-yl)-1-(((1r,4r)-4-methoxycyclohexyl)methyl)-3,4-dihydropyrazino[2,3-b]pyrazin-2(1H)-one | 0.006 | | >0.5 | | |
| 160 | 6-(5-fluoro-2-methyl-4-(1H-1,2,4-triazol-3-yl)phenyl)-4-(((1s,4s)-4-methoxycyclohexyl)methyl)-3,4-dihydropyrazino[2,3-b]pyrazin-2(1H)-one | <0.0015 | | >0.5 | | |
| 161 | 7-(1H-pyrrolo[2,3-b]pyridin-4-yl)-1-(2-(tetrahydro-2H-pyran-4-yl)ethyl)-3,4-dihydropyrazino[2,3-b]pyrazin-2(1H)-one | 0.385 | | 2.790 | | |
| 162 | 7-(1H-benzo[d]imidazol-4-yl)-1-(2-(tetrahydro-2H-pyran-4-yl)ethyl)-3,4-dihydropyrazino[2,3-b]pyrazin-2(1H)-one | 4.752 | | >5 | | |
| 163 | 6-(5-fluoro-2-methyl-4-(1H-1,2,4-triazol-3-yl)phenyl)-4-(((1r,4r)-4-methoxycyclohexyl)methyl)-3,4-dihydropyrazino[2,3-b]pyrazin-2(1H)-one | >0.5 | | >0.5 | | |
| 164 | 6-(4-methyl-6-(1H-1,2,4-triazol-3-yl)pyridin-3-yl)-4-((tetrahydro-2H-pyran-4-yl)methyl)-3,4-dihydropyrazino[2,3-b]pyrazin-2(1H)-one | 0.001 | | 0.275 | | |
| 165 | 7-(6-(1H-1,2,4-triazol-3-yl)pyridin-3-yl)-1-(((1s,4s)-4-methoxycyclohexyl)methyl)-3,4-dihydropyrazino[2,3-b]pyrazin-2(1H)-one | 0.000 | | 0.003 | | |
| 166 | 1-ethyl-7-(1H-pyrrolo[3,2-b]pyridin-5-yl)-3,4-dihydropyrazino[2,3-b]pyrazin-2(1H)-one | >0.5 | | >0.5 | | |
| 167 | 7-(5-fluoro-2-methyl-4-(1H-1,2,4-triazol-3-yl)phenyl)-1-(((1s,4s)-4-methoxycyclohexyl)methyl)-3,4-dihydropyrazino[2,3-b]pyrazin-2(1H)-one | <0.0015 | | <0.0015 | | |
| 168 | 7-(5-fluoro-2-methyl-4-(1H-1,2,4-triazol-3-yl)phenyl)-1-(((1r,4r)-4-methoxycyclohexyl)methyl)-3,4-dihydropyrazino[2,3-b]pyrazin-2(1H)-one | 0.000 | | | | |

TABLE 4-continued

| Cmpd No. C- | Chemical name | MSD p70S6K | Luminex p70S6K | MSD GSK-3β | Luminex GSK-3β | Luminex PRAS40 |
|---|---|---|---|---|---|---|
| 169 | 6-(1H-pyrrolo[2,3-b]pyridin-3-yl)-4-(2-(tetrahydro-2H-pyran-4-yl)ethyl)-3,4-dihydropyrazino[2,3-b]pyrazin-2(1H)-one | 0.419 | | 2.815 | | |

As can be seen in Tables 2-4, compounds of formulas I, III and IV are able to inhibit both TORC1 and TORC2 direct and indirect substrates in several cancer cell lines, with certain compounds showing submicromolar potency for one or more substrates.

The embodiments disclosed herein are not to be limited in scope by the specific embodiments disclosed in the examples which are intended as illustrations of a few aspects of the disclosed embodiments and any embodiments that are functionally equivalent are encompassed by the present disclosure. Indeed, various modifications of the embodiments disclosed herein are in addition to those shown and described herein will become apparent to those skilled in the art and are intended to fall within the scope of the appended claims.

A number of references have been cited, the disclosures of which are incorporated herein by reference in their entirety.

What is claimed is:

1. A method for detecting or measuring the inhibition of TOR kinase activity in a patient having cancer, comprising measuring the amount of phosphorylated PRAS40, GSK3β or p70S6K1 in a biological sample from said patient, prior to and after the administration of 7-(6-(2-hydroxypropan-2-yl)pyridin-3-yl)-1-(trans-4-methoxycyclohexyl)-3,4-dihydropyrazino[2,3-b]pyrazin-2(1H)-one or a pharmaceutically acceptable salt, stereoisomer or tautomer thereof to said patient.

2. A method for determining whether a patient having cancer is sensitive to 7-(6-(2-hydroxypropan-2-yl)pyridin-3-yl)-1-(trans-4-methoxycyclohexyl)-3,4-dihydropyrazino[2,3-b]pyrazin-2(1H)-one or a pharmaceutically acceptable salt, stereoisomer or tautomer thereof, comprising administering said patient said 7-(6-(2-hydroxypropan-2-yl)pyridin-3-yl)-1-(trans-4-methoxycyclohexyl)-3,4-dihydropyrazino[2,3-b]pyrazin-2(1H)-one or a pharmaceutically acceptable salt, stereoisomer or tautomer thereof and determining whether or not TOR kinase activity is inhibited in said patient by measuring the amount of phosphorylated PRAS40, GSK3β or p70S6K1 in a biological sample from said patient, prior to and after the administration of said 7-(6-(2-hydroxypropan-2-yl)pyridin-3-yl)-1-(trans-4-methoxycyclohexyl)-3,4-dihydropyrazino[2,3-b]pyrazin-2(1H)-one or a pharmaceutically acceptable salt, stereoisomer or tautomer thereof to said patient.

3. A method for determining the effective amount of 7-(6-(2-hydroxypropan-2-yl)pyridin-3-yl)-1-(trans-4-methoxycyclohexyl)-3,4-dihydropyrazino[2,3-b]pyrazin-2(1H)-one or a pharmaceutically acceptable salt, stereoisomer or tautomer thereof for the treatment of a cancer treatable by inhibition of phosphorylation of PRAS40, GSK3β and/or p70S6K1 in a patient having cancer, comprising administering said patient varying doses of said 7-(6-(2-hydroxypropan-2-yl)pyridin-3-yl)-1-(trans-4-methoxycyclohexyl)-3,4-dihydropyrazino[2,3-b]pyrazin-2(1H)-one or a pharmaceutically acceptable salt, stereoisomer or tautomer thereof and determining the amount of TOR kinase activity inhibition in said patient resulting from each dose of said 7-(6-(2-hydroxypropan-2-yl)pyridin-3-yl)-1-(trans-4-methoxycyclohexyl)-3,4-dihydropyrazino[2,3-b]pyrazin-2(1H)-one or a pharmaceutically acceptable salt, stereoisomer or tautomer thereof by measuring the amount of phosphorylated PRAS40, GSK3β or p70S6K1 in a biological sample from said patient, prior to and after the administration of each dose of said 7-(6-(2-hydroxypropan-2-yl)pyridin-3-yl)-1-(trans-4-methoxycyclohexyl)-3,4-dihydropyrazino[2,3-b]pyrazin-2(1H)-one or a pharmaceutically acceptable salt, stereoisomer or tautomer thereof to said patient.

4. The method of claim 3, the cancer is prostate cancer, lung cancer, colon cancer, glioma or breast cancer.

* * * * *